United States Patent
Evans et al.

(10) Patent No.: US 11,376,264 B2
(45) Date of Patent: Jul. 5, 2022

(54) USE OF BROMODOMAIN-CONTAINING PROTEIN 9 ANTAGONISTS IN COMBINATION WITH VITAMIN D RECEPTOR AGONISTS IN DIABETES TREATMENT

(71) Applicant: Salk Institute for Biological Studies, La Jolla, CA (US)

(72) Inventors: Ronald M. Evans, La Jolla, CA (US); Michael Downes, San Diego, CA (US); Zong Wei, San Diego, CA (US); Annette Atkins, San Diego, CA (US); Ruth T. Yu, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 16/737,312

(22) Filed: Jan. 8, 2020

(65) Prior Publication Data
US 2020/0129532 A1 Apr. 30, 2020

Related U.S. Application Data

(63) Continuation of application No. PCT/US2018/043345, filed on Jul. 23, 2018.

(60) Provisional application No. 62/536,154, filed on Jul. 24, 2017.

(51) Int. Cl.
| | |
|---|---|
| *A61K 31/59* | (2006.01) |
| *A61P 3/10* | (2006.01) |
| *A61K 9/00* | (2006.01) |
| *A61K 31/427* | (2006.01) |
| *A61K 31/4365* | (2006.01) |
| *A61K 31/4439* | (2006.01) |
| *A61K 45/06* | (2006.01) |

(52) U.S. Cl.
CPC ............ *A61K 31/59* (2013.01); *A61K 9/0019* (2013.01); *A61K 31/427* (2013.01); *A61K 31/4365* (2013.01); *A61K 31/4439* (2013.01); *A61K 45/06* (2013.01); *A61P 3/10* (2018.01)

(58) Field of Classification Search
CPC ...................................... A61K 31/59
USPC ........................................ 514/167
See application file for complete search history.

(56) References Cited

U.S. PATENT DOCUMENTS

| | | | |
|---|---|---|---|
| 5,961,990 | A | 10/1999 | Delrieu et al. |
| 6,358,939 | B1 | 3/2002 | Hayes et al. |
| 8,318,708 | B2 | 11/2012 | Evans et al. |
| 9,872,866 | B2 | 1/2018 | Ding et al. |
| 9,895,381 | B2 | 2/2018 | Sherman et al. |
| 2005/0009793 | A1 | 1/2005 | Curd |
| 2005/0124591 | A1 | 6/2005 | Tian et al. |
| 2005/0148557 | A1 | 6/2005 | Tian et al. |
| 2006/0074109 | A1 | 4/2006 | Polvino et al. |
| 2006/0135610 | A1 | 6/2006 | Bortz et al. |
| 2006/0178351 | A1 | 8/2006 | Curd et al. |
| 2006/0240150 | A1 | 10/2006 | Delaney et al. |
| 2007/0197517 | A1 | 8/2007 | Jani et al. |
| 2007/0275934 | A1 | 11/2007 | Curd |
| 2008/0193512 | A1 | 8/2008 | Niitsu et al. |
| 2009/0209500 | A1 | 8/2009 | Evans et al. |
| 2010/0099640 | A1 | 4/2010 | Geuns et al. |
| 2011/0014126 | A1 | 1/2011 | Evans et al. |
| 2016/0106762 | A1 | 4/2016 | Ding et al. |
| 2018/0200379 | A1 | 7/2018 | Sherman et al. |

FOREIGN PATENT DOCUMENTS

| | | |
|---|---|---|
| CN | 1261800 A | 8/2000 |
| CN | 1520301 A | 8/2004 |
| CN | 102342914 A | 2/2012 |
| CN | 102869675 A | 1/2013 |
| EP | 0 682 879 A1 | 11/1995 |
| JP | 2008-050375 | 3/2008 |
| JP | 174463 | 7/2008 |
| JP | 2013-56834 A | 3/2013 |
| JP | 2014-508796 | 4/2014 |
| WO | WO 1998/056387 A1 | 12/1998 |
| WO | WO 2003/002060 A2 | 1/2003 |
| WO | WO 2005/117542 A2 | 12/2005 |
| WO | WO 2008/024485 A2 | 2/2008 |
| WO | WO 2008/057363 A2 | 5/2008 |
| WO | WO 2009/061961 A1 | 5/2009 |
| WO | WO 2010/143986 A1 | 12/2010 |
| WO | WO 2011/092575 A1 | 8/2011 |
| WO | WO 2011/143209 A1 | 11/2011 |
| WO | WO 2012/127037 A2 | 9/2012 |
| WO | WO 2016/077378 A1 | 5/2016 |
| WO | WO 2016/139361 A1 | 9/2016 |
| WO | WO 2016/149382 A2 | 9/2016 |
| WO | WO 2018/106738 A1 | 6/2018 |

OTHER PUBLICATIONS

Shi et al., Nano Lett. (2010) vol. 10(9), pp. 3223-3230.*
Sheng-Nan et al., Chin. Phys. B (2014) vol. 23(3), pp. 037503-1 to 037503-19.*
Martin et al., J. Med. Chem. (2016) vol. 59, pp. 4462-4475.*
Abramovitch et al., "Vitamin D inhibits proliferation and profibrotic marker expression in hepatic stellate cells and decreases thioacetamide-induced liver fibrosis in rats," *Gut,* 60:1728-1737, 2011.
Adorini el al., "Inhibition of Type 1 Diabetes Development by Vitamin D Receptor Agonists," *Curr Med Chem.—Anti-Inflammatory & Anti-Allergy Agents* 4:645-651, 2005.
Author unknown, "Support plug that skin injection to increase the risk of acute pancreatitis," *Adverse Drug Reactions* 11:71, 2009 (with English machine translation).

(Continued)

*Primary Examiner* — Taofiq A Solola
(74) *Attorney, Agent, or Firm* — Klarquist Sparkman, LLP

(57) ABSTRACT

Methods are provided for reducing blood glucose, which utilize an agent that increases the biological activity of a vitamin D receptor (VDR) (e.g., a VDR agonist), in combination with an antagonist of bromodomain-containing protein 9 (BRD9). IN some examples, such methods treat type II diabetes.

18 Claims, 24 Drawing Sheets

Specification includes a Sequence Listing.

(56) References Cited

OTHER PUBLICATIONS

Beer et al., "A Phase I Trial of Pulse Calcitriol in Patients with Refractory Malignancies," *Cancer* 91:2431-2439, 2001.
Cai Hongneng, "Paclitaxel combination chemotherapy film adenocarcinoma," 3 Yu Cheng Zhangwei by the Affiliated Hospital of Beijing Military Medical Sciences, Beijing 100039, China, 1997 (with English machine translation).
Cao et al., "Leptin Stimulates Tissue Inhibitor of Metalloproteinase-1 in Human Hepatic Stellate Cells," *J. Biol. Chem.*, vol. 279, pp. 4292-4304, 2004.
Cohen-Lahav et al., "The Anti-Inflammatory Activity of 1,25-Dihydroxyvitamin D3 in Macrophages," *J. Steroid. Biochem. Mol. Biol.*, vol. 103, pp. 558-562, 2007.
Dai et al., "PPAR gamma is an important transcription factor in 1 alpha, 25-dihydroxyvitaim D3-induced involucrin expression," *J. Derm. Sci*, vol. 51, No. 1, pp. 53-60, Apr. 2008.
Demetter et al., "Molecular Changes in Pancreatic Cancer: Implications for Molecular Targeting Therapy," *Acta Gastro-Enterological Belgica* 75:210-214, 2012.
Ding et al., "A vitamin D receptor/SMAD genomic circuit gates hepatic fibrotic response," *Cell*, vol. 153, No. 3, pp. 601-613, Apr. 25, 2013.
Dunlop et al., "The human peroxisome proliferator-activated receptor δ gene is a primary target of $1\alpha,25$-dihydroxy vitamin $D_3$ and it nuclear receptor," *J. Mol. Biol.*, vol. 349, No. 2, pp. 248-260, Jun. 2005.
Fearon, "The Carcinoma-Associated Fibroblast Expressing Fibroblast Activation Protein and Escape from Immune Surveillance," *Cancer Immunol Res.* 2:187-193, 2014.
Feig et al., "Targeting CXCL12 from FAP-Expressing Carcinoma-Associated Fibroblasts Synergizes with Anti-PD-L1 Immunotherapy in Pancreatic Cancer," *Proc Natl Acad Sci. USA* 110:20212-20217, 2013.
Gao et al., "Pancreatic Stellate Cells Increase the Invasion of Human Pancreatic Cancer Cells through the Stromal Cell-Derived Factor-1/CXCR4 Axis," *Pancreatedology* 10:186-193, 2010.
Gascon-Barré et al., "The Normal Liver Harbors the Vitamin D Nuclear Receptor in Nonparenchymal and Biliary Epithelial Cells," *Hepatology*, 37:1034-1042, 2003.
Johnson et al., "The Activated Mesangial Cell: A Glomerular 'Myofibroblast'?," *J. Am. Soc. Nephrol.*, vol. 2, pp. S190-S197, 1992.
Johnson et al., "The Antitumor Efficacy of Calcitriol: Preclinical Studies," *Anticancer Res.* 26:2543-2500, 2006.
Jonas et al., "Measurement of Parenchymal Function and Bile Duct Flow in Primary Sclerosing Cholangitis Using Dynamic $^{99m}$Tc-HIDA SPECT," *J. Gastroenterol. Hepatol.* vol. 21, pp. 674-681, 2006.
Klöppel et al., "Fibrosis of the pancreas: the initial tissue damage and the resulting pattern," *Virchows Arch*, vol. 445, pp. 1-8, May 2004.
Li et al., "Mannose 6-Phosphate-Modified Bovine Serum Albumin Nanoparticles for Controlled and Targeted Delivery of Sodium Ferulate for Treatment of Heptatic Fibrosis," *J Pharm Pharmacol.* 61:1155-1161, 2009.
Ma et al., "$1.25D_3$ enhances antitumor activity of gemcitabine and cisplatin in human bladder cancel models," *Cancer*, 116:3294-3303, Jul. 1, 2010.
Mahadevan & Hoff, "Tumor-stroma interactions in pancreatic ductual adenocaricinoma," *Mol Cancer Ther.* 6:1186-1197, 2007.
McCarroll et al., "Vitamin A inhibits pancreatic stellate cell activation: implications for treatment of pancreatic fibrosis," *Gut* 55:79-89, 2006.
Milczarek et al., "Vitamin D Analogs Enhance the Anticancer Activity of 5-Fluorouracil in an in vivo Mouse Colon Cancer Model," *BMC Cancer* 13:294 (2013).
Omary et al., "The Pancreatic Stellate Cell: A Star on the Rise in Pancreatic Diseases," *J. Clin. Invest.* vol. 117, pp. 50-59, 2007.

Payer et al., "Vitamin D Deficiency as One of the Causes of Bone Changes in Chronic Pancreatitis," *Vnitr Lek.* 45:281-283, 1999. (English Abstract Only).
Petta et al., "Low Vitamin D Serum Level Is Related to Severe Fibrosis and Low Responsiveness to Interferon-Based Therapy in Genotype 1 Chronic Hepatitis C," *Hepatology*, vol. 51, pp. 1158-1167, 2010.
Remillard et al., "Degradation of the BAF Complex Factor BRD9 by Heterobifunctional Ligands," *Angew Chem Int Ed Engl.* 56:5738-5743, 2017.
Samer et al., "Rat Primary and Immortalized Human Hepatocytes Express an Inducible and Functional Vitamin D Receptor," Abstract, Hepatology & Luminal Research Workshop & Clinical Update on Non-Invasive Markers of Liver Injury and Early Diagnosis of Liver Disease, 1-3, Yarra Valley, Victoria, Australia, May 2009.
Sato et al., "Resolution of Liver Cirrhosis Using Vitamin A-Coupled Liposomes to Deliver siRNA Against a Collagen-Specific Chaperone," *Nat Biotechnol.* 26:431-442, 2008.
Suda et al., "Pancreatic fibrosis in patients with chronic alcohol abuse: correlation with alcoholic pancreatitis," *Am J Gastroenterol*, 89:2060-2062, Nov. 1994.
Tan et al., "Paricalcitol Attenuates Renal Interstitial Fibrosis in Obstructive Nephropathy," *J. Am. Soc. Nephrol*, vol. 17, pp. 3382-3393, 2006.
Tan et al., "Therapeutic Role and Potential Mechanisms of Active Vitamin D in Renal Interstitial Fibrosis," *J. Steroid. Biochem. Mol. Biol.*, 103:491-496, 2007.
Theodoulou et al., "Discovery of I-BRD9, a Selective Cell Active Chemical Probe for Bromodomain Containing Protein 9 Inhibition," *J Med Chem.* 59:1425-1439, 2016.
Wehr et al., "Analysis of the Human Pancreatic Stellate Cell Secreted Proteome," *Pancreas* 40:557-566, 2011.
Whitcomb, "Genetic aspects of pancreatitis," *Annual Review of Medicine*, vol. 61, pp. 413-424, Palo Alto, 2010.
Wurm and Frey, "Linear-Dendritic Block Copolymers: The State of the Art and Exciting Perspectives," *Polymer Sci.* 36:1-52, 2011.
Zehnder et al., "Expression of 25-Hydroxyvitamin D3-1alpha-hydroxylase in the Human Kidney," *J. Am. Soc. Nephrol.*, vol. 10, pp. 2465-2473, 1999.
Zhang et al., "Interactions of Nanomaterials and Biological Systems: Implications to Personalized Nanomedicine," *Adv Drug Deliv.* 64:1363-1384, 2012.
Zhang, "Advances mechanism and antifibrotic treatment of chronic pancreatitis film gland fibrosis," *Chin J Pancreatol.* 1:56-58, 2001 (with English machine translation).
Zollner et al., "Role of Nuclear Receptors in the Adaptive Response to Bile Acids and Cholestasis: Pathogenetic and Therapeutic Considerations," *Mol. Pharm.*, vol. 3, pp. 231-251, 2006.
AU 2008323903 Office Action dated Mar. 6, 2013 (6 pages).
CA 2703994 Office Action dated Nov. 6, 2014 (6 pages).
CA 2703994 Office Action dated Nov. 4, 2015 (3 pages).
CN 201480035908.4 Office Action dated Jul. 27, 2017 (with English translation) (6 pages).
EP 08846682.6 Office Action dated Apr. 18, 2013 (6 pages).
EP 08846682.6 Office Action dated Aug. 8, 2017 (5 pages).
EP 08846682.6 Office Action dated Feb. 1, 2016 (5 pages).
EP 08846682.6 Search Report dated Nov. 9, 2010 (12 pages).
EP 14787709.6 Communication Pursuant to Rule 164(1) EPC dated Sep. 13, 2016 with Supplementary Partial European Search Report dated Aug. 19, 2016 (dated Sep. 13, 2016) (9 pages).
EP 14787709.6 Exam Report dated Dec. 5, 2018 (7 pages).
EP 14806812.5 Rule 164(1) EPC Communication dated Nov. 3, 2016 with Supplementary Partial European Search Report dated Oct. 25, 2016 (11 pages).
PCT/US2014/035235 International Search Report and Written Opinion dated Sep. 17, 2014 (18 pages).
PCT/US2014/041063 International Search Report and Written Opinion dated Sep. 5, 2014 (10 pages).
PCT/US2018/043345 International Search Report and Written Opinion dated Sep. 12, 2018 (11 pages).

* cited by examiner

FIG. 3A Human beta-like cells IL-1b stress
FIG. 3B INS-1
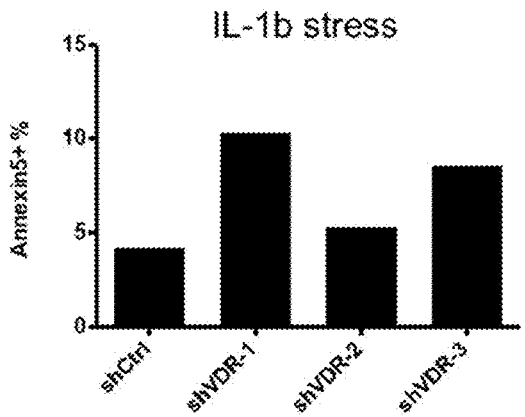
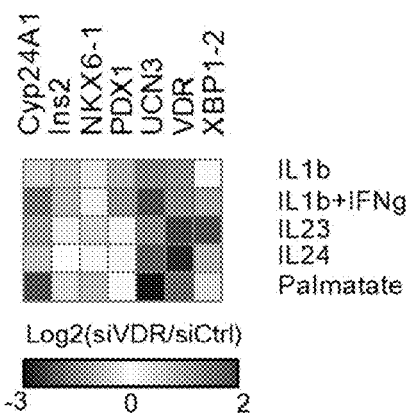
FIG. 3C Insulin
FIG. 3D Proinsulin
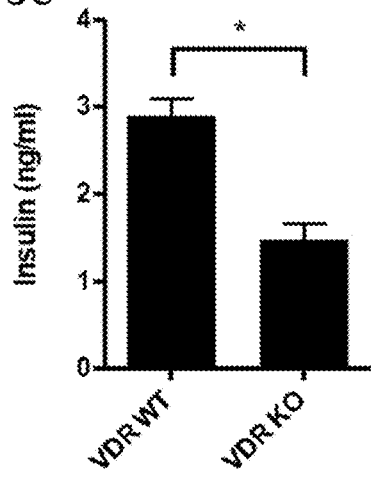
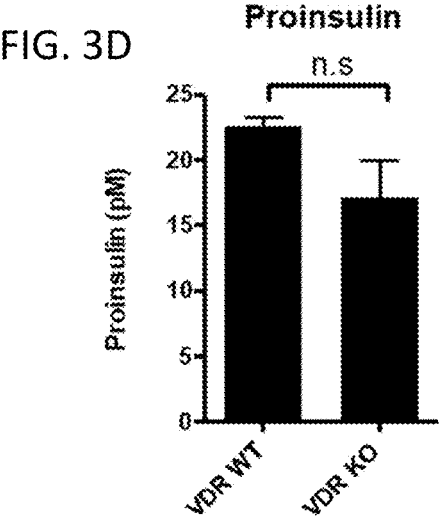
FIG. 3E
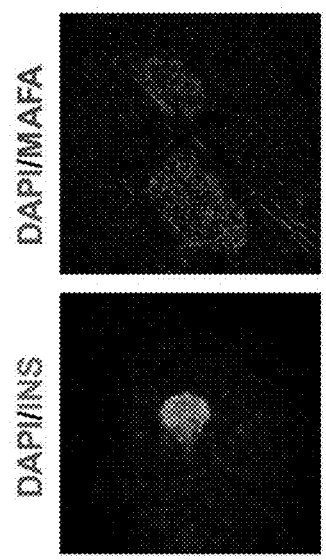
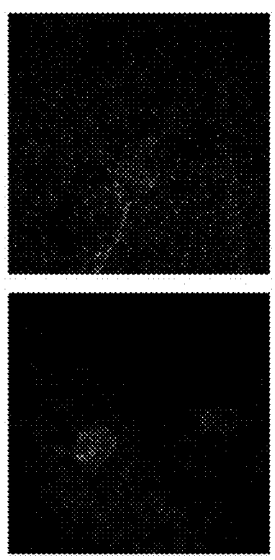
FIG. 3F Mouse Islets 48 hr / Mouse Islets 96 hr
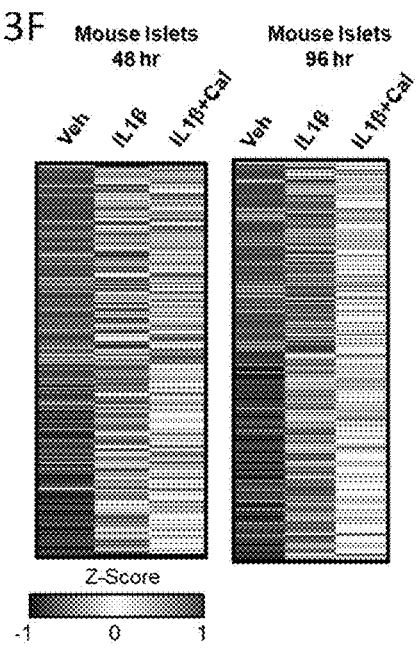

FIG. 3G
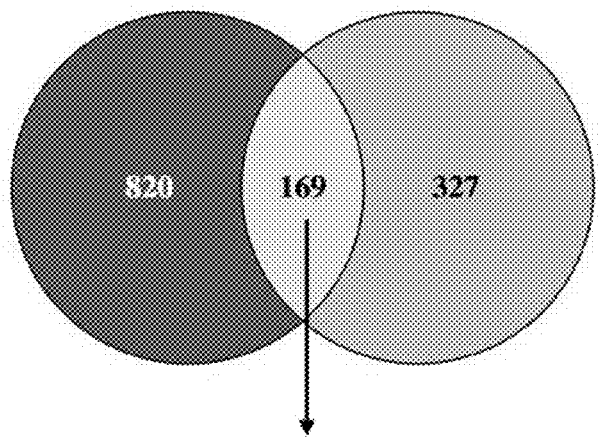
FIG. 3H
| Description | LogP |
|---|---|
| tissue morphogenesis | -6.02 |
| positive regulation of hormone secretion | -4.35 |
| cellular response to peptide hormone stimulus | -4.21 |
| Insulin secretion | -3.60 |
FIG. 3I
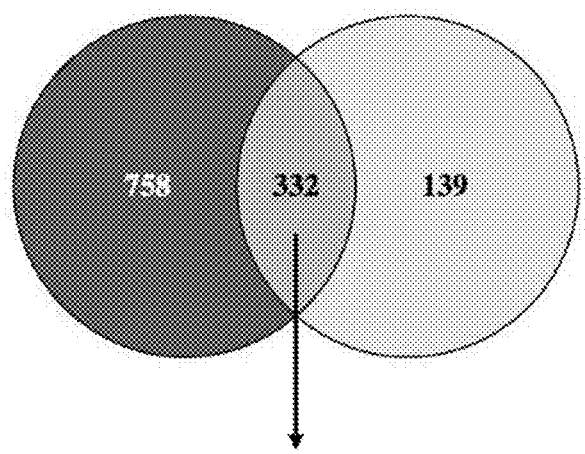
FIG. 3J
| Description | LogP |
|---|---|
| negative regulation of cell proliferation | -13.25 |
| Innate Immune System | -12.76 |
| cytokine production | -12.69 |
| apoptotic signaling pathway | -12.22 |
| inflammatory response | -11.73 |
| response to wounding | -11.09 |
| response to cytokine | -8.25 |

FIG. 4F
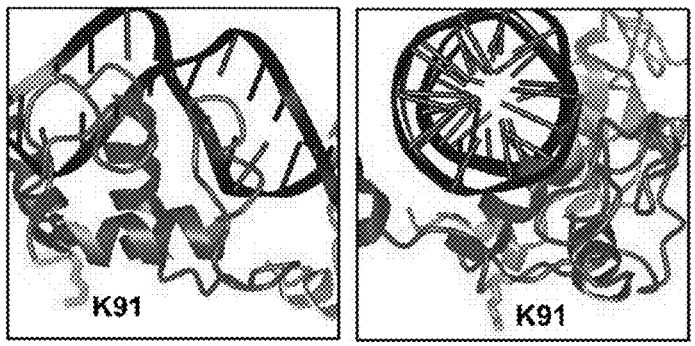
FIG. 4H
293T
VDR-HA+BRD7-FL
FIG. 4G
293T VDR(WT/K91Mut)-HA
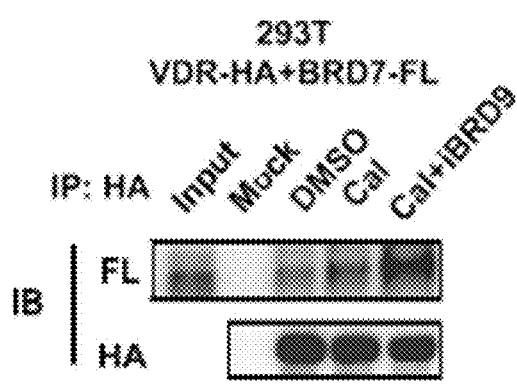
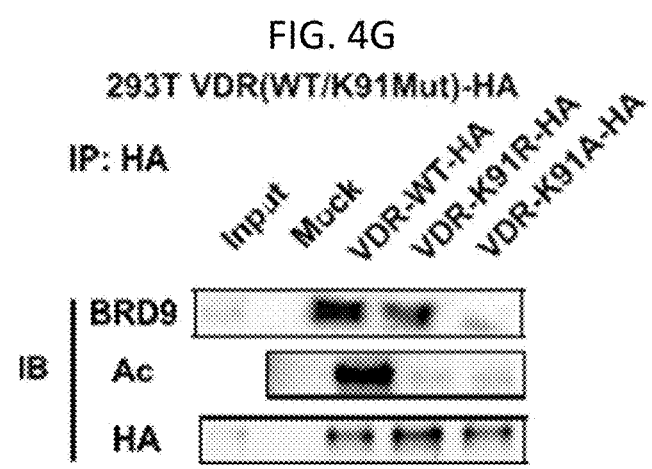
FIG. 4I
293T VDR(WT/K91Mut)-HA+BRD7-FL
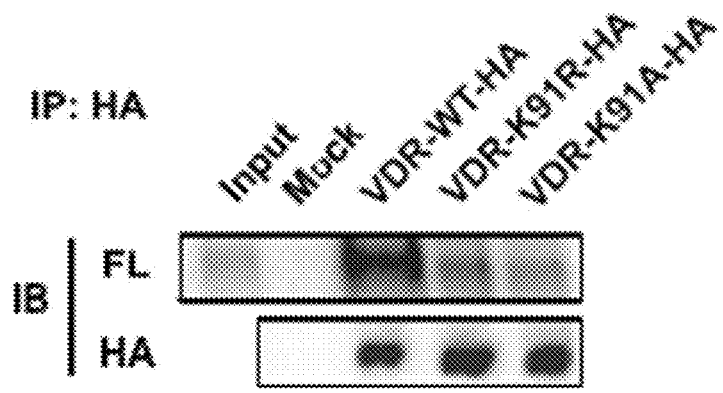

INS-1 VDR-HA

IP: HA

293T VDR-HA + PCAF IP: HA

FIG. 5G
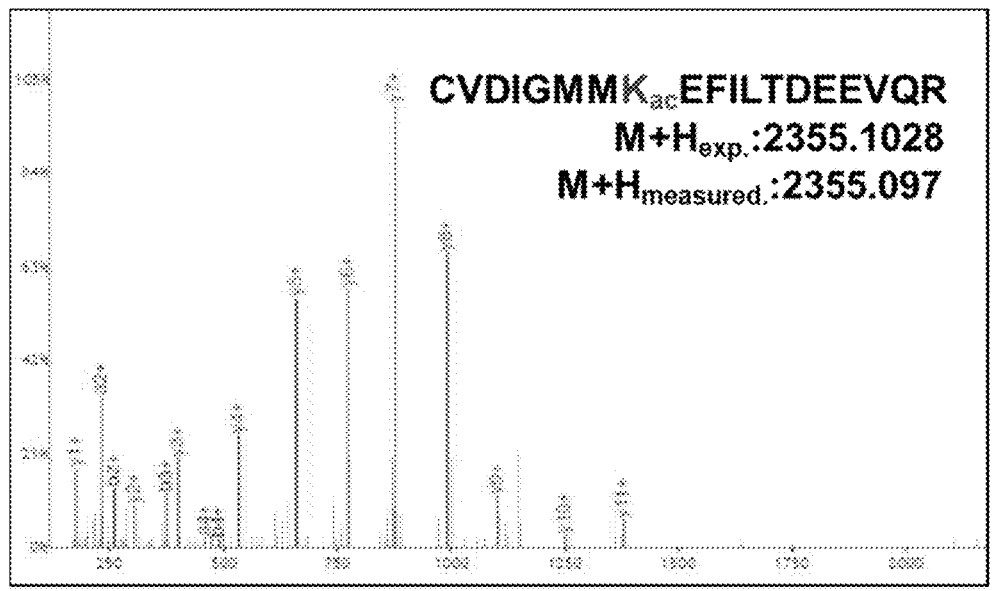
FIG. 5H
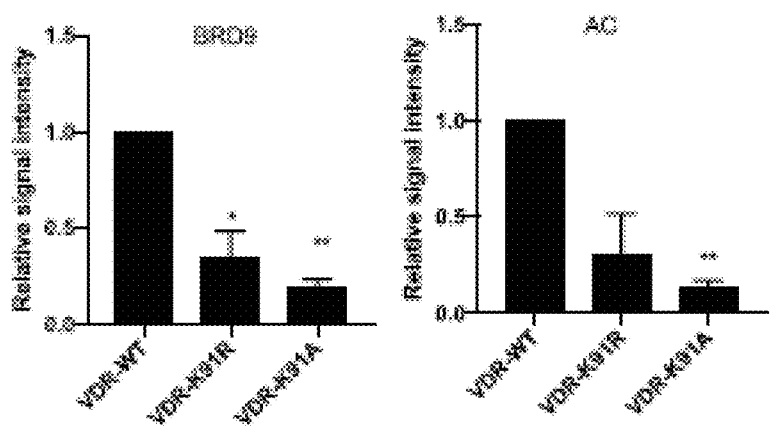
FIG. 5I
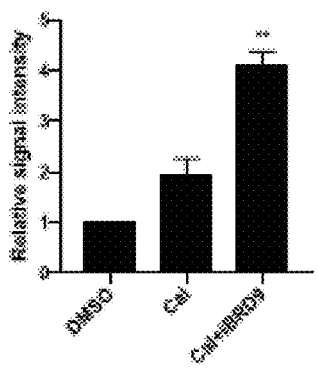
FIG. 5J

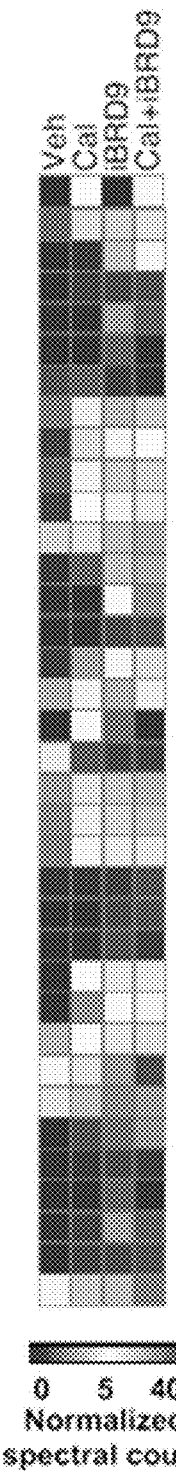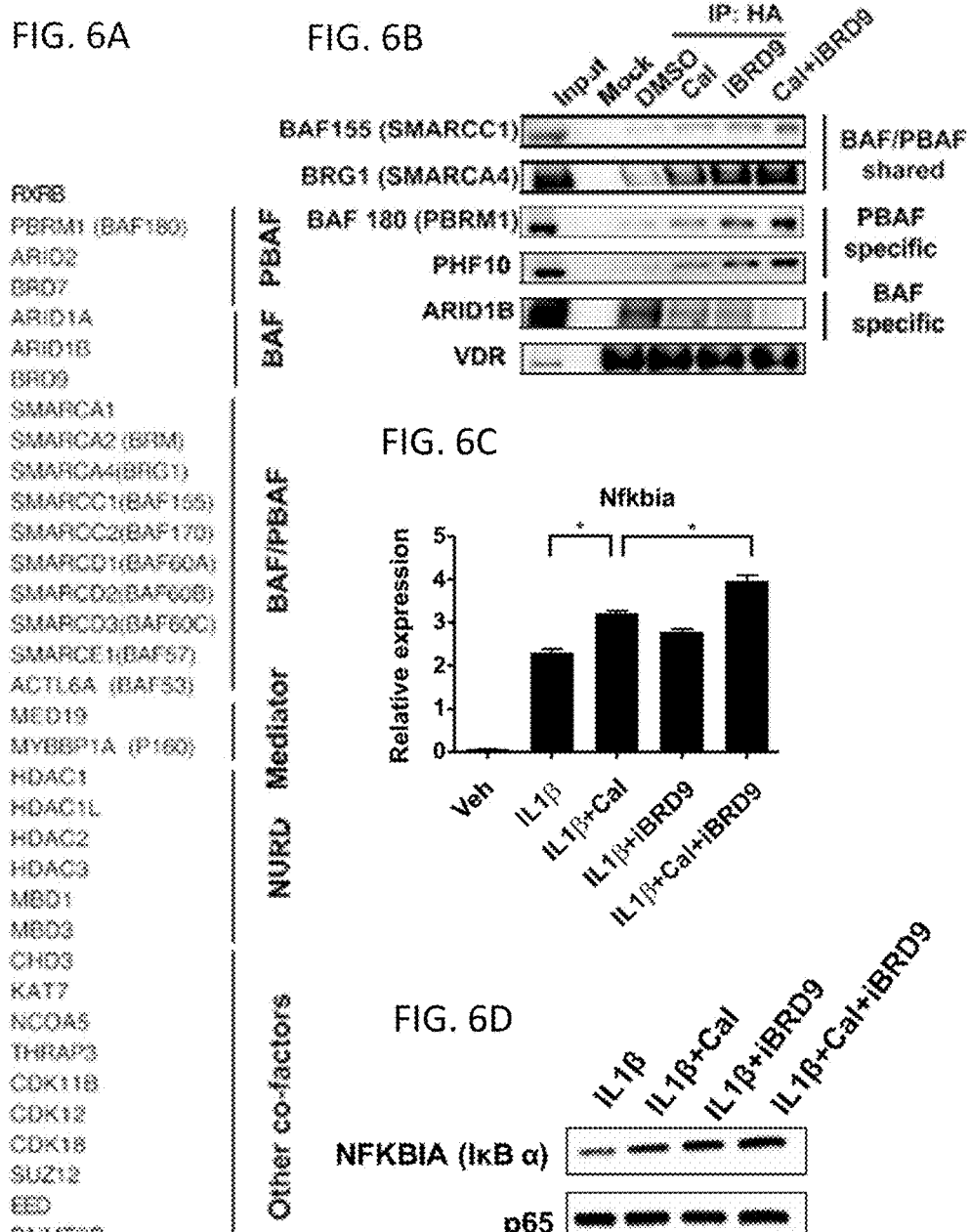

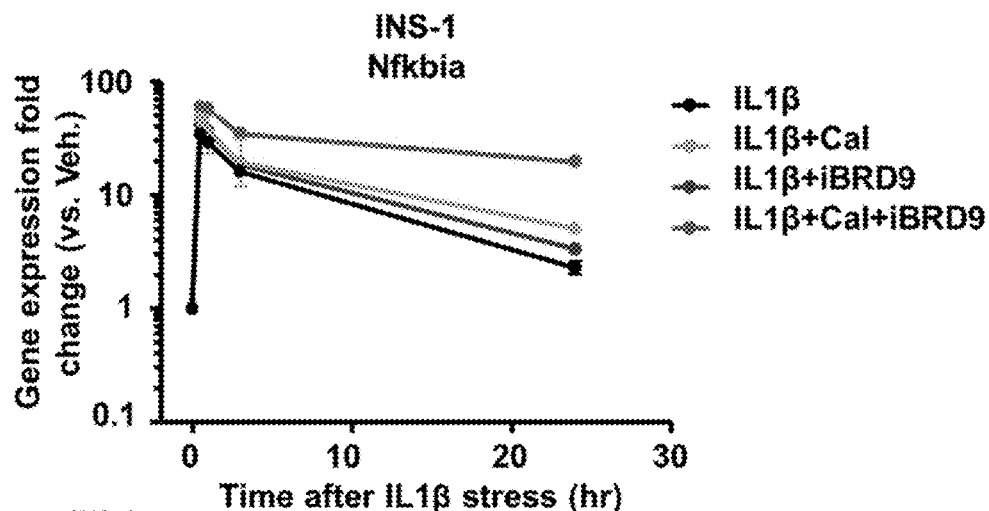
FIG. 6E
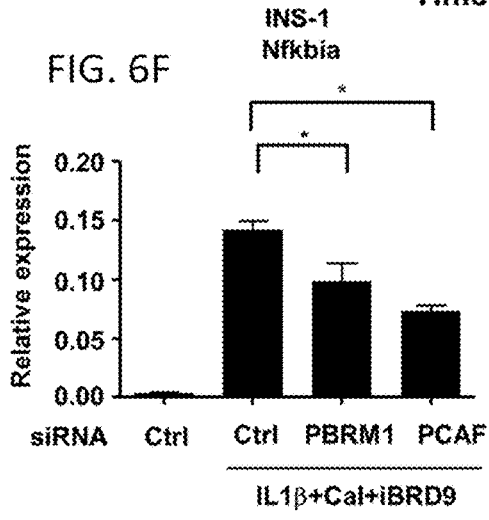
FIG. 6F
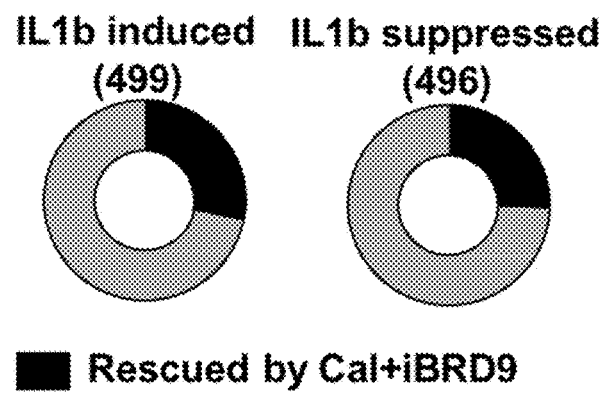
FIG. 7A
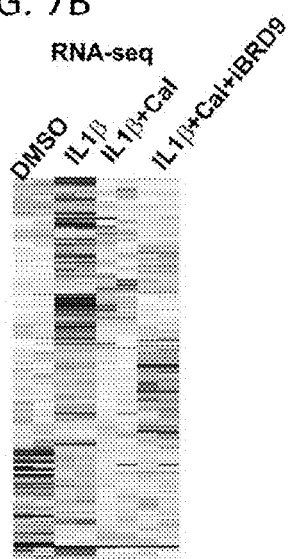
FIG. 7B
FIG. 7C
| Description | LogP |
|---|---|
| positive regulation of hormone secretion | -5.06 |
| tube development | -4.08 |
| embryonic organ development | -2.97 |
| negative regulation of response to endoplasmic reticulum stress | -3.64 |

FIG. 7D

| Description | LogP |
|---|---|
| negative regulation of cell proliferation | -6.84 |
| positive regulation of immune system process | -5.10 |
| TNF signaling pathway | -4.87 |
| MAPK cascade | -4.67 |
| I-kappaB kinase/NF-kappaB signaling | -4.14 |
| DNA damage response, signal transduction by p53 class mediator | -3.89 |
| response to interleukin-1 | -3.25 |

FIG. 7E

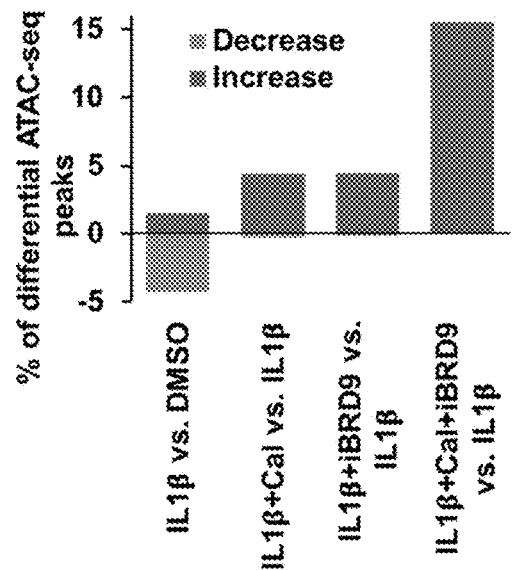

FIG. 7F ATAC-seq

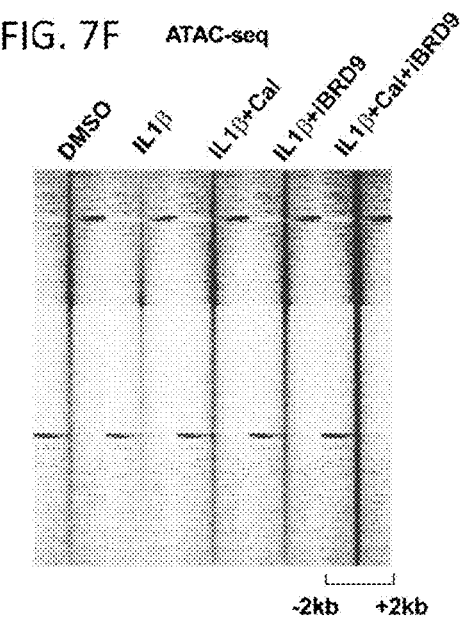

FIG. 7H

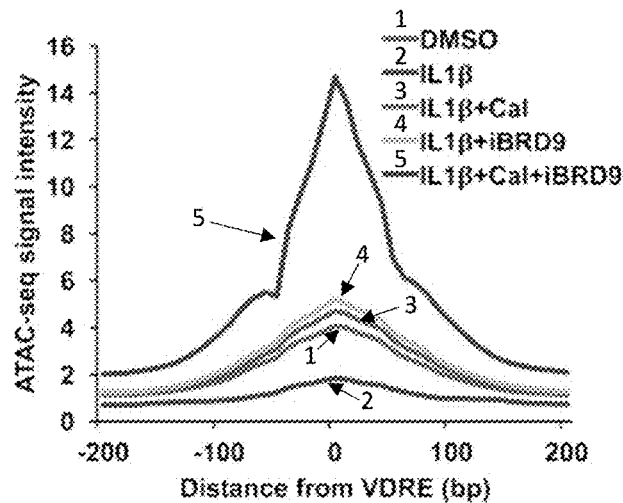

FIG. 7G

| Motif | TF | P-Value |
|---|---|---|
| CCA_CT_T | CTCF | 1e-138 |
| TCA_A_TTCA | VDR:RXRA | 1e-100 |
| CCATCT | NeuroD1 | 1e-30 |
| CT_AAACA | Foxa2 | 1e-30 |
| TAAT | NKX6-1 | 1e-24 |

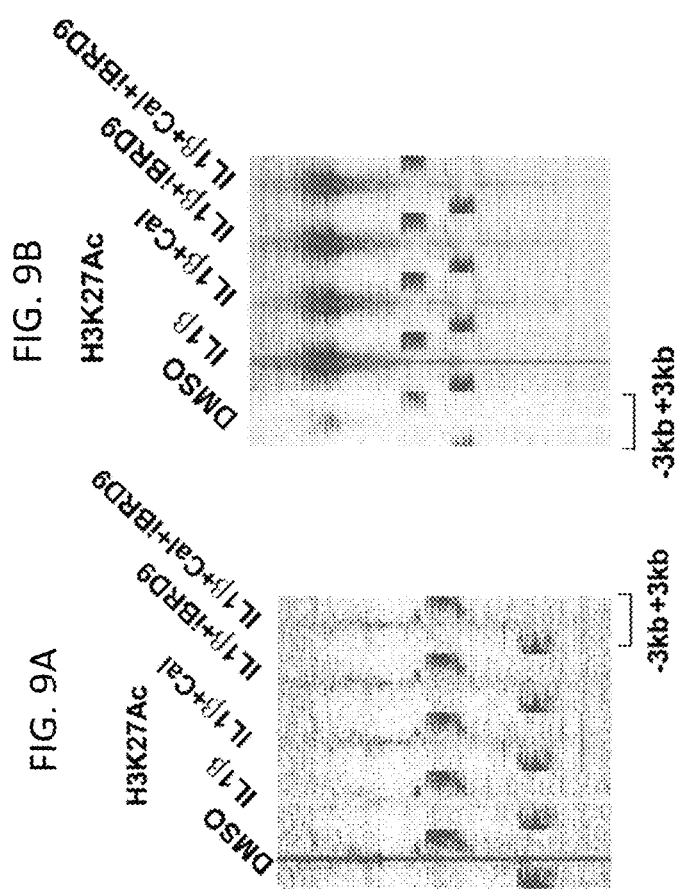
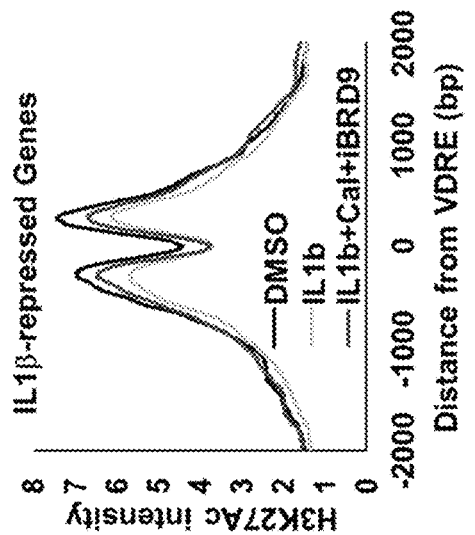
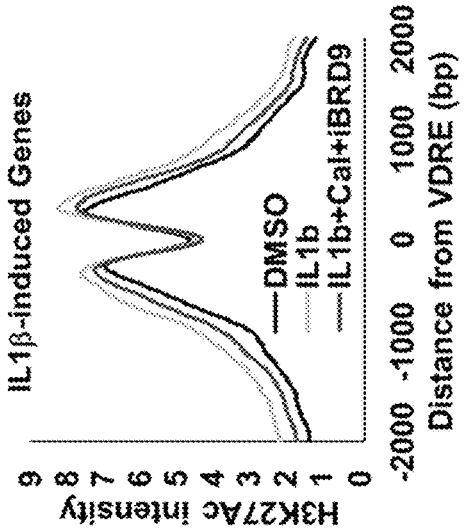

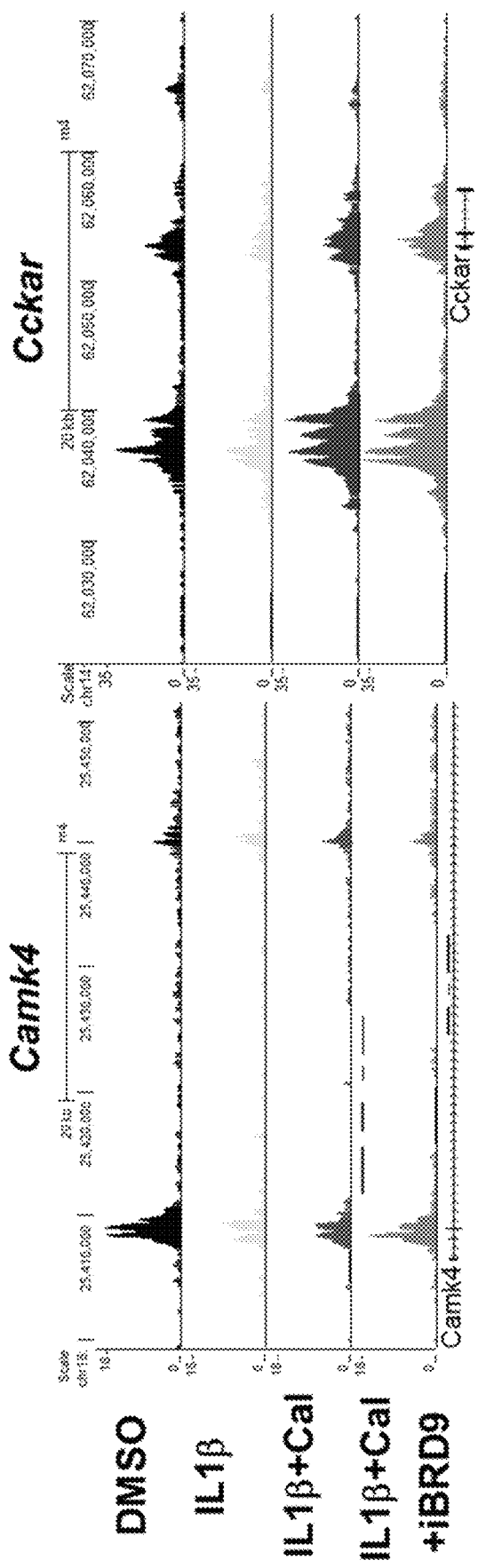
FIG. 9F
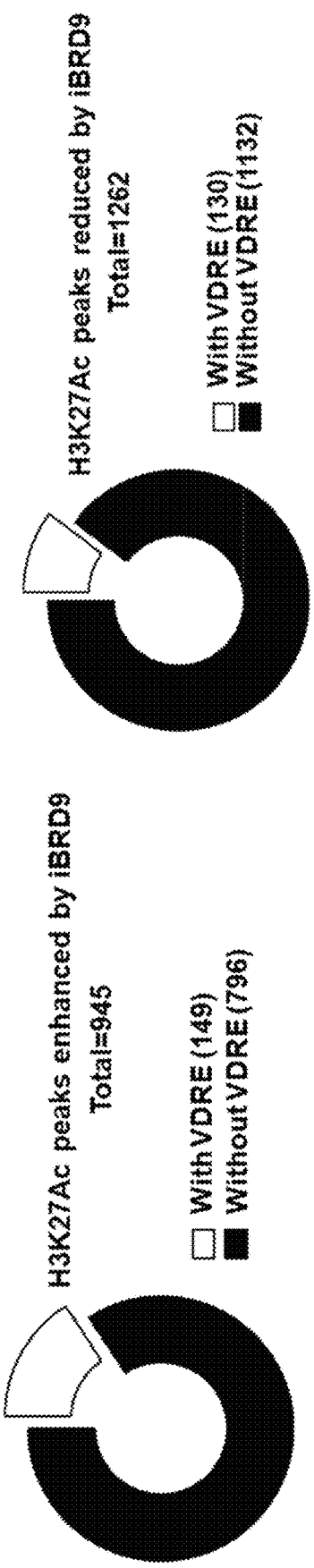
FIG. 9J
FIG. 9G

| Description | LogP |
|---|---|
| positive regulation of cell migration | -4.53 |
| desensitization of G-protein coupled receptor protein signaling pathway | -3.78 |
| hormone secretion | -3.05 |
| regulation of cell development | -2.73 |
| cAMP signaling pathway | -2.61 |
| digestive tract development | -2.57 |

| Description | LogP |
|---|---|
| regulation of cytokine production involved in inflammatory response | -3.84 |
| neuron apoptotic process | -3.63 |
| tumor necrosis factor superfamily cytokine production | -3.44 |
| positive regulation of cell death | -2.61 |
| intrinsic apoptotic signaling pathway in response to DNA damage | -2.55 |

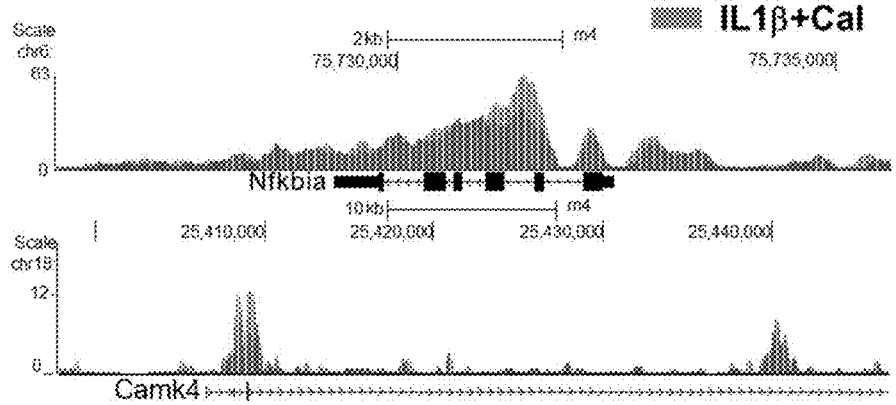

FIG. 9I

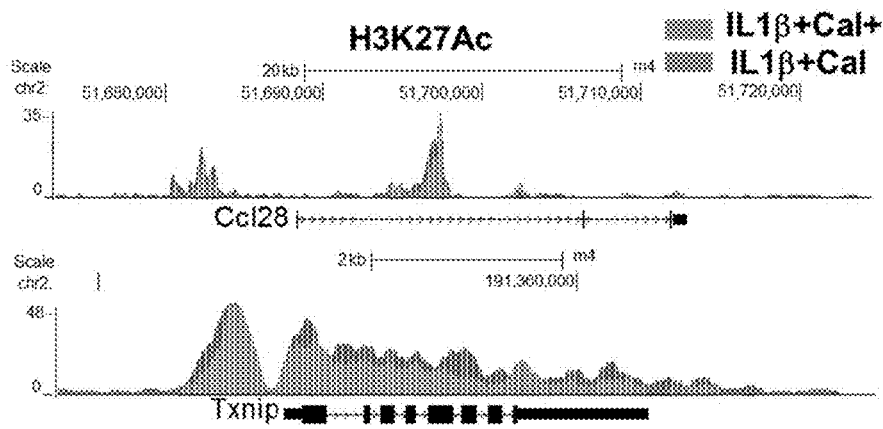

FIG. 9L

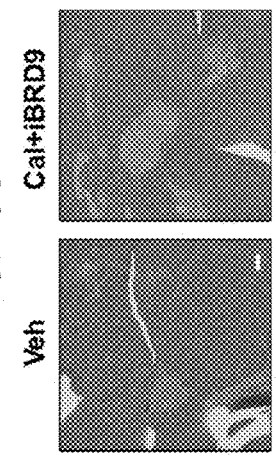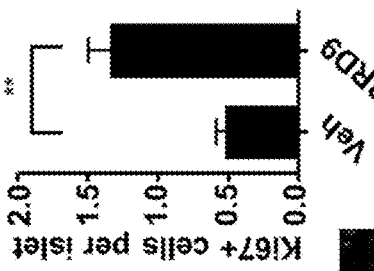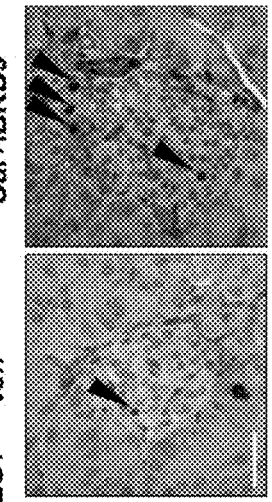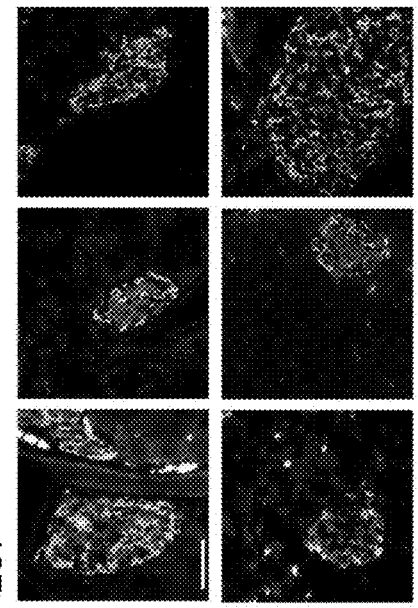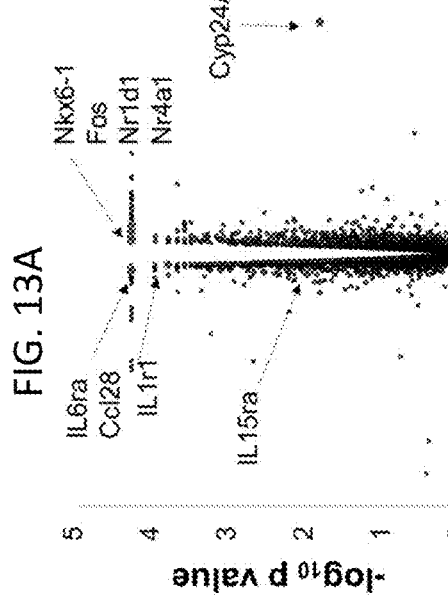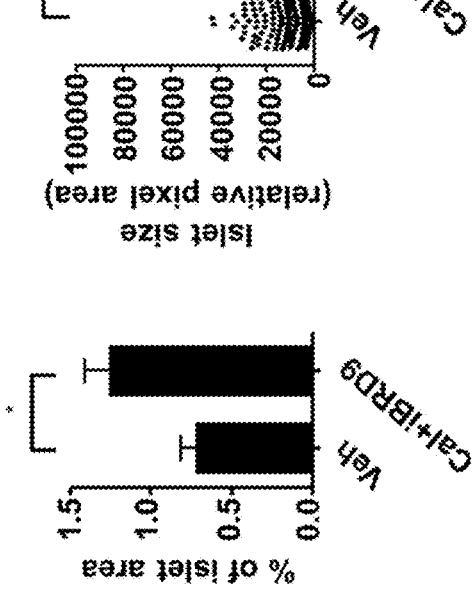

SEQUENCE LISTING

<160> NUMBER OF SEQ ID NOS: 50

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ctctatccat ggctacctgg                                              20

<210> SEQ ID NO 2

```
<211> LENGTH: 19
<212> TYPE: DNA
<213> ORGANISM: Artificial Sequence
<220> FEATURE:
<223> OTHER INFORMATION: primer

<400> SEQUENCE: 2
ccattacagg gctcctgag                                                    19

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
tgtgaagaag cgagacctg                                                    19

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
tcctctatgg gaacttgaaa gg                                                22

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
atcgagcttc gagactgtg                                                    19

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
agttgttaaa gctgtgccg                                                    19

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
gggagatgtg aagatgctg                                                    19

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
```
aagtgtagga cactgtccc                                                19

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
tgccctattt aaaggcctgt ct                                            22

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
cgagttgtga atggcacact t                                             21

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
acggatatca gcaccctgac                                               20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
attggttgag ccagcgatac                                               20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gactgtgggc atcaatctcc                                               20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
acaggtgaca gggaactgct                                               20

<210> SEQ ID NO 15
<211> LENGTH: 21
<212> TYPE: DNA

```
<213> ORGANISM: Artificial Sequence
<220> FEATURE:
<223> OTHER INFORMATION: primer

<400> SEQUENCE: 15
tctctgatcc agaccttcca a                                              21

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gaagtccaga ccgttatgca g                                              21

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tttgtcaagc agcacctttg                                                20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tctacaatgc cacgcttctg                                                20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gagaaatgaa gttgctgctg                                                20

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
ctttcaccat ctccagagc                                                 19

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
caactctcac tgaagccag                                                 19
```

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
ttaactgcat ctggctgag                                                  19

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
cagagcttga aggtgttgc                                                  19

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
agtgtggcta tgacttcgg                                                  19

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
gaaatgccac cttttgacag tg                                              22

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
tggatgctct catcaggaca g                                               21

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
tagtccttcc taccccaatt tcc                                             23

<210> SEQ ID NO 28
<211> LENGTH: 21
<212> TYPE: DNA
<213> ORGANISM: Artificial Sequence
<220> FEATURE:

```
<223> OTHER INFORMATION: primer

<400> SEQUENCE: 28
ttggtcctta gccactcctt c                                      21

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
atctttgctg cgatcaacag                                        20

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
tgatgtacac gtgtcattcc a                                      21

<210> SEQ ID NO 31
<211> LENGTH: 16
<212> TYPE: DNA
<213> ORGANISM: Artificial Sequence
<220> FEATURE:
<223> OTHER INFORMATION: primer

<400> SEQUENCE: 31
gagtccgcag caggtg                                            16

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
gtgtcagaga gtccatggga                                        20

<210> SEQ ID NO 33
<211> LENGTH: 19
<212> TYPE: DNA
<213> ORGANISM: Artificial Sequence
<220> FEATURE:
<223> OTHER INFORMATION: primer

<400> SEQUENCE: 33
aagtccactt acagggagc                                         19

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
tagaacttgt gggagaggc                                         19
```

```
<210> SEQ ID NO 35
<211> LENGTH: 19
<212> TYPE: DNA
<213> ORGANISM: Artificial Sequence
<220> FEATURE:
<223> OTHER INFORMATION: primer

<400> SEQUENCE: 35
aaatccacca aagctcacg                                                    19

<210> SEQ ID NO 36
<211> LENGTH: 19
<212> TYPE: DNA
<213> ORGANISM: Artificial Sequence
<220> FEATURE:
<223> OTHER INFORMATION: primer

<400> SEQUENCE: 36
attccttctc cagctccag                                                    19

<210> SEQ ID NO 37
<211> LENGTH: 19
<212> TYPE: DNA
<213> ORGANISM: Artificial Sequence
<220> FEATURE:
<223> OTHER INFORMATION: primer

<400> SEQUENCE: 37
gtacttggca ggaccagag                                                    19

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
ttctggaacc agaccttgac                                                   20

<210> SEQ ID NO 39
<211> LENGTH: 21
<212> TYPE: DNA
<213> ORGANISM: Artificial Sequence
<220> FEATURE:
<223> OTHER INFORMATION: primer

<400> SEQUENCE: 39
gtggcgagtt cagactgttg t                                                 21

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
tttttctagt ctgactggct tgg                                               23

<210> SEQ ID NO 41
<211> LENGTH: 20
<212> TYPE: DNA
<213> ORGANISM: Artificial Sequence
<220> FEATURE:
<223> OTHER INFORMATION: primer
```

```
<400> SEQUENCE: 41
tgggttccag cttctaggac                                              20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ccaacgcttt atcctctgcc                                              20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
gtgagtcagg tcagcatgga                                              20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
actcatgttt cctggagcga                                              20

<210> SEQ ID NO 45
<211> LENGTH: 9
<212> TYPE: PRT
<213> ORGANISM: Homo sapiens

<400> SEQUENCE: 45

Gly Met Met Lys Gly Gly Ile Arg Lys
1               5

<210> SEQ ID NO 46
<211> LENGTH: 9
<212> TYPE: PRT
<213> ORGANISM: Homo sapiens

<400> SEQUENCE: 46

Gly Met Lys Lys Glu Met Ile Met Ser
1               5

<210> SEQ ID NO 47
<211> LENGTH: 9
<212> TYPE: PRT
<213> ORGANISM: Homo sapiens

<400> SEQUENCE: 47

Gly Met Arg Lys Asp Met Ile Leu Ser
1               5

<210> SEQ ID NO 48
<211> LENGTH: 9
<212> TYPE: PRT
<213> ORGANISM: Homo sapiens
```

```
<400> SEQUENCE: 48

Gly Met Ser Lys Glu Ser Val Arg Asn
1               5

<210> SEQ ID NO 49
<211> LENGTH: 9
<212> TYPE: PRT
<213> ORGANISM: Homo sapiens

<400> SEQUENCE: 49

Gly Met Ser Lys Glu Ser Val Arg Asn
1               5

<210> SEQ ID NO 50
<211> LENGTH: 9
<212> TYPE: PRT
<213> ORGANISM: Homo sapiens

<400> SEQUENCE: 50

Gly Met Met Lys Glu Phe Ile Leu Thr
1               5
```

USE OF BROMODOMAIN-CONTAINING PROTEIN 9 ANTAGONISTS IN COMBINATION WITH VITAMIN D RECEPTOR AGONISTS IN DIABETES TREATMENT

CROSS-REFERENCE TO RELATED APPLICATIONS

This application is a continuation of International Application No. PCT/US2018/043345 filed Jul. 23, 2018, which was published in English under PCT Article 21(2), which in turn which claims priority to U.S. provisional application No. 62/536,154 filed Jul. 24, 2017, both herein incorporated by reference in their entireties.

FIELD

This disclosure provides methods of using an agent compound that increases the biological activity of a vitamin D receptor (VDR) (e.g., a VDR agonist), in combination with an antagonist of bromodomain-containing protein 9 (BRD9), to reduce blood glucose in a mammal, for example to treat type II diabetes.

BACKGROUND

Already a global epidemic, the incidence of T2D is expected to rapidly escalate in the coming decades. Initiated by insulin resistance, β cell dysfunction characterized by defective insulin secretion, endoplasmic reticulum (ER) stress and eventual β cell loss causally associates with disease progression (Ashcroft and Rorsman, 2012, Cell 148, 1160-71) (Halban et al., 2014, Diabetes care 37, 1751-8). Multiple therapeutic approaches currently combat hyperglycemia, however few treatments directly target (3 cell pathogenesis (Zhou et al., 2016, Nature reviews 12, 337-346). Thus, long-term control of disease progression remains challenging (Kahn et al., 2014, Lancet 383, 1068-1083).

The molecular underpinnings of obesity-induced 0 cell dysfunction are not fully understood (Donath et al., 2013, Cell metabolism 17, 860-872; Guo et al., 2013, J. Clin. Invest. 123, 3305-16; Talchai et al., 2012, Cell 150, 1223). Evidence links inflammation and specifically, the innate immune response of pancreatic islets to metabolic stress, to T2D progression (Donath and Shoelson, 2011, Nature reviews 11, 98-107) (Fernandez-Real and Pickup, 2012, Diabetologia 55, 273-8; Imai et al., 2013, Trends Endocrinol. Metab. 24, 351-360). In particular, inflammatory stress associated with increased interleukin 1β (IL1β) reduces insulin secretion and leads to β cell damage and loss of identity (Marzban, 2015, Diabetes 64, 1094-1096; Herder et al., 2015, TEM 26, 551-563; Morris, 2015, Molecular endocrinology 29, 946-962). Blocking IL1β signaling by antagonists has shown modest β cell functional improvement, although the long term efficacy remains to be determined (Donath et al., 2013, Cell metabolism 17, 860-872).

The anti-inflammatory activities of the vitamin D receptor (VDR), combined with epidemiological and human genetic studies linking vitamin D and VDR to both type 1 and 2 diabetes (Takiishi et al., 2010, (Takiishi et al., 2010, Endocrinol. Metab. Clin. North Am. 39, 419-446)), provide VDR as a therapeutic target for diabetes (Bouillon et al., 2008, Endocrine Rev. 29, 726-776; Baeke et al., 2010, Current Opin. Pharmacol. 10, 482-496; Cantorna et al., 2004, Am J Clin Nutr 80, 1717S-1720S). However, although vitamin D supplements reverse many diabetic phenotypes in T1D animal models (Del Pino-Montes et al., 2004, Calcif Tissue Int 75, 526-532; Mathieu et al., 1994, Diabetologia 37, 552-558), the therapeutic benefits in type 2 diabetic patients are less clear (Takiishi et al., 2010, Endocrinol. Metab. Clin. North Am. 39, 419-446). Given the limited understanding of the role of VDR in β cells, the potential benefits of activating VDR in pathological β cells in vivo are unknown.

Bromodomain-containing protein 9 (BRD9) is a member of a diverse nuclear and cytoplasmic family of proteins that recognize acetylated lysines (Filippakopoulos and Knapp, 2014, Nat. Rev. Drug Discov. 13, 337-356). Structural differences in the bromodomain of BRD9 distinguish it from other members such BRD2, BRD4 and BRDT (Filippakopoulos et al., 2010, Nature 468, 1067-73). BRD9 is a core component of the SWI/SNF (BAF) complex and, similar to other BAF components, is found to be mutated in multiple cancers (Kadoch et al., 2013, Nature genetics 45, 592-601).

SUMMARY

It is shown therein that VDR is a modulator of the stress response in beta (3) cells, and BRD9 is a determinant in the VDR-driven anti-inflammatory and pro-survival responses. In the absence of stress, BRD9 recruits the suppressive BAF transcriptional complex to silence VDR. In a dual regulatory mechanism, inhibition of the VDR-BRD9 interaction in combination with ligand activation of VDR cooperate to dismiss the BAF complex in favor of the activating PBAF complex to induce a coordinated transcriptional response. Notably, VDR ligand in combination with a BRD9 inhibitor is able to partially restore β cell function and glucose homeostasis in T2D mouse models. These results reveal an unexpected post-translational control of VDR function through a bromodomain reader and implicate its potential therapeutic function in diabetes.

Based on these observations, methods of using a therapy that uses both a vitamin D receptor (VDR) agonist and a bromodomain-containing protein 9 (BRD9) antagonist are provided. In some examples, such methods are used to treat a disorder that benefits from increased VDR activity, such as fibrosis (such as fibrosis of the lung, liver, kidney or pancreas), autoimmune disorders, and type II diabetes (T2D).

In some examples the methods include administering a therapeutically effective amount of one or more VDR agonists and one or more BRD9 antagonists to reduce blood glucose in a mammal, such as a decrease of at least 5%, at least 10%, at least 25%, at least 50%, or at least 75%. In some examples the methods include administering a therapeutically effective amount of one or more VDR agonists and one or more BRD9 antagonists to treat type 2 diabetes in a mammal. In some examples the methods include administering a therapeutically effective amount of one or more VDR agonists and one or more BRD9 antagonists to reduce fed and fasting blood glucose (such as a decrease of at least 5%, at least 10%, at least 25%, at least 50%, or at least 75%), increase insulin sensitivity (such as an increase of at least 10%, at least 25%, at least 50%, at least 75%, at least 80%, at least 90%, at least 95%, at least 100%, at least 200%, or at least 300%), increase glucose tolerance (such as an increase of at least 10%, at least 25%, at least 50%, at least 75%, at least 80%, at least 90%, at least 95%, at least 100%, at least 200%, or at least 300%), increase insulin secretion (such as an increase of at least 10%, at least 25%, at least 50%, at least 75%, at least 80%, at least 90%, at least 95%, at least 100%, at least 200%, or at least 300%), increase beta cell function (such as an increase of at least 10%, at least 25%, at least 50%, at least 75%, at least 80%, at least 90%, at least 95%, at least 100%, at least 200%, or at least 300%), increase the size of islets (such as an increase of at least 10%, at least 25%, at least 50%, at least 75%, at least 80%, at least 90%, at least 95%, at least 100%, at least 200%, or at least 300%), reduce beta cell death (such as a decrease of at least 5%, at least 10%, at least 25%, at least 50%, at least 75%, at least 80%, at least 90% or at least 95%), increase insulin granules (such as an increase of at least 10%, at least 25%, at least 50%, at least 75%, at least 80%, at least 90%, at least 95%, at least 100%, at least 200%, or at least 300%), reduce fibrosis (such as a decrease of at least 5%, at least 10%, at least 25%, at least 50%, at least 75%, at least 80%, at least 90% or at least 95%), treat an autoimmune disease, or combinations thereof.

Also provided are compositions that include one or more VDR agonists and one or more BRD9 antagonists. In some examples, such a composition is part of a nanoparticle. Also provided are kits that include one or more VDR agonists and one or more BRD9 antagonists.

Examples of VDR agonists that can be used include but are not limited to vitamin D, a vitamin D precursor, a vitamin D analog, a vitamin D receptor ligand, a vitamin D receptor agonist precursor, and combinations thereof. Examples of BRD9 antagonists that can be used include but are not limited to i-BRD9, TP742, BI-7273, BI-9564, dBRD9, GNE-375 and LP-99.

The foregoing and other objects and features of the disclosure will become more apparent from the following detailed description, which proceeds with reference to the accompanying figures.

BRIEF DESCRIPTION OF THE DRAWINGS

FIGS. 3A-3J. VDR is essential for R cell function. (A) Percentage of apoptotic cells, as measured by FACS analysis for Annexin5, in control and VDR knockdown human β-like cells. (B) Heat map of relative gene expression changes between control (siCtrl) and VDR knockdown (siVDR) INS1 cells in response to different stress conditions, as determined by qPCR. (C) Serum insulin levels in VDR$^{+/+}$ and VDR$^{-/-}$ mice (n=4, error bars show S.E.M., *P<0.05). (D) Serum proinsulin levels in VDR$^{+/+}$ and VDR$^{-/-}$ mice (n=4, error bars show S.E.M.). (E) Staining of MAFA and Insulin in VDR WT and VDR KO islets. (F) Heat maps of gene expression in mouse islets treated with vehicle, IL1β, or IL1β+Cal for 48 or 96 hours, showing the genes induced by IL1β are partially rescued by Cal treatment. (G) Venn diagram showing the overlap of between genes significantly suppressed by IL1β and genes rescued by Cal (VDR agonist calcipotriol) at 96 hours. (H) Gene ontology categories enriched in the 169 genes suppressed by IL1β and rescued by Cal at 96 hours. (I) Venn diagram showing the overlap between genes significantly induced by IL1β and genes rescued by Cal at 96 hours. (J) Gene ontology categories of the 332 genes induced by IL1β and rescued by Cal at 96 hours.

FIGS. 4A-4L. Bromodomain-containing proteins BRD7 and BRD9 bind acetylated VDR. (A) Heat map of VDR interacting proteins in human β-like cells in the absence or presence of ligand Cal, determined by MudPIT analyses (24 h after doxycycline induction of HA-VDR and ligand addition). Spectral counts normalized to VDR. (B) Western blot of endogenous BRD9 in immunoprecipitates from 293T cells expressing HA-tagged VDR treated with vehicle (DMSO), Cal, the BRD9 inhibitor iBRD9, or Cal+iBRD9. (C) Western blot of ectopically expressed VDR in immunoprecipitates from 293T cells expressing Flag-tagged BRD9, 1h after treatment with DMSO, Cal, iBRD9, or Cal+iBRD9. (D) In vitro interaction of purified full-length HA-VDR with the bromodomain of BRD9 fused to GST. (E) Alignment of T-box sequences from related nuclear receptors showing conservation of the VDR acetylated lysine K91 (from top to bottom, SEQ ID NOS: 45-50). (F) Crystal structure of the DNA binding domains of VDR (red) bound to DNA (blue), highlighting the sidechain of K91 (green) (PDB ID: 1kb2). (G) Western blot of endogenous BRD9 in immunoprecipitates from 293T cells expressing wild type, K91R, or K91A HA-tagged VDR. Acetylated VDR detected with pan acetyl lysine antibody. (H) Western blot of ectopically expressed VDR in immunoprecipitates from 293T cells expressing Flag-tagged BRD7, 1h after treatment with DMSO, Cal, or Cal+iBRD9. (I) Western blot of ectopically expressed Flag-BRD7 in immunoprecipitates from 293T cells expressing wild type, K91R, or K91A HA-tagged VDR. (J) Reported increases in hydrogen-deuterium exchange upon addition of 1,25 (OH)$_2$ vitamin D mapped onto the crystal structure of the DNA binding domain of VDR. (K) Western blot of endogenous PCAF in IP from INS1 cells expressing HA-VDR, 1 hr after indicated treatments. (L) Western blot of ectopically expressed HA-VDR in IP from 293T cells over-expressing wild-type or an enzymatically dead PCAF (D608A).

FIGS. 5A-5J. VDR acetylation and BAF interaction. (A) Immunoprecipitation of endogenous BAF/PBAF components in 293T cells shows that BRD9 interacts with BAF components BRG1 and ARID1B, but does not interact with PBAF component ARID2; (B) Scatterplot of the p value of all genes enriched in the drop-out screen with VDR labeled in red. Several epigenetic modifiers, including BRD7, are labeled in green; (C) Western blot of endogenous BRD9 in immunoprecipitates from 293T cells expressing HA-tagged VDR treated with vehicle (DMSO), Cal, the BRD9 inhibitor iBRD9, or Cal+iBRD9; (D) Quantification of relative signal intensity corresponding to (C) (n=2, error bars show S.E.M., **p<0.01); (E) Quantification of relative signal intensity corresponding to FIG. 2C (n=2, error bars show S.E.M., *p<0.05, **p<0.01); (F) Western blotting of full-length His-VDR showing that the SF9 (insect)-produced recombinant protein is acetylated; (G) Mass-spectrum indicating that lysine 91 on human VDR is acetylated; (H) Quantification of relative signal intensity corresponding to FIG. 4G (n=2, error bars show S.E.M., *p<0.05, p<0.01); (I) Quantification of relative signal intensity corresponding to FIG. 4H (n=2, error bars show S.E.M., p<0.01); (J) Quantification of relative signal intensity corresponding to FIG. 4I (n=2, error bars show S.E.M., **p<0.01).

FIGS. 6A-6F. BRD9 represses VDR activation upon acute cytokine stress in β cells. (A) Heat map of MudPit mass-spectral analyses of VDR interactomes in INS1 cells expressing HA-tagged VDR. Ligand and iBRD9-treated cells show increased interactions between VDR and PBAF-specific components PBRM1 and ARID2, but not BAF-specific components ARID1A and ARID1B. Interactions between VDR and mediator components, NURD complex and other co-factors also increase upon ligand or iBRD9 treatment. Spectral counts in individual samples are normalized by counts of VDR. (B) Western blots demonstrating that the interaction of VDR with PBAF complex components BAF180, PHF10, as well as shared BAF/PBAF components BAF155 and BRG1, increased with Cal or iBRD9 treatment, whereas the interaction with BAF complex-specific component ARID1B decreased upon activation of VDR. (C) qPCR results for early response (30 min) of IL1β stressed INS1 cells show a synergy of Cal and iBRD9 in up-regulating Nfkbia (IκBα), an early negative feedback regulator of NFκB signaling pathways. (n=3, error bars show S.E.M. *P<0.05). (D) Changes in NFKBIA (IκBα) protein levels correlate with gene expression changes in INS1 cells treated with IL1β for 30 mins. (E) Time course of Nfkbia expression during cytokine stress suggest that a synergy between iBRD9 and Cal can increase the expression of Nfkbia upon IL1β stress. The prolonged enhancement of Nfkbia expression can still be observed after 24 hrs, whereas Cal alone is not sufficient to induce a significant increase in Nfkbia expression (n=3, error bars show S.E.M., *P<0.05). (F) siRNA knock-down of BRD9, PBAF complex key component PBRM1 (BAF180), as well as PCAF confirming their significance in regulating Nfkbia expression (n=3, error bars show S.E.M., *P<0.05).

FIGS. 7A-7I. Synergy between iBRD9 and Cal directly reverse the transcriptome changes brought by IL10 and influence global DNA accessibility. (A) Number of genes significantly induced or repressed by 1 hour IL1β stress. The black bars represent genes rescued by Cal+iBRD9. (B) Heat map of all Cal+iBRD9 rescued genes. (C) Gene ontology categories of Cal+iBRD9 rescued IL1β-repressed genes indicate that the majority of these genes are related to β cell function including hormone secretion, development, and anti-ER stress response. (D) Gene ontology categories of Cal+iBRD9-rescued IL1β-induced genes indicate that the majority of these genes are related to β cell inflammatory and stress responses. (E) Percentage of differentially accessible regions (>4 fold) in multiple comparisons. IL1β stress (1 hr) induces increases as well as decreases in ATAC-seq peak intensity. Compared with IL1β stressed cells, Cal or iBRD9-treated samples primarily increase chromatin accessibility. The addition of both Cal and iBRD9 results in a synergistic increase in chromatin accessibility and demonstrate a genome-wide increase of accessibility for ~15% of all ATAC-seq peaks. (F) Heat map showing changes in chromatin accessibility 1 hour after the indicated treatments. Compared with DMSO treatment, chromatin accessibility measured by ATAC-seq peak intensity is overwhelmingly suppressed by IL1β, which is rescued by Cal or iBRD9. A "hyper-activated" state is seen upon combinatorial treatment of Cal and iBRD9. (G) Enriched transcription factors (TF) motifs in Cal+iBRD9 induced ATAC-seq peaks. (H) Chromatin accessibility at identified VDR response elements (VDREs) increases with Cal+iBRD9 treatment. (I) Genome browser tracks of ATAC-seq signals at 3 representative gene loci: Nfkbia, Nfkbiz, and Cckar, all showing a synergistic effect of Cal+iBRD9 at enhancer regions.

FIGS. 9A-9L. Activation of VDR directly antagonizes the global enhancer dynamics induced by IL1P. (A) Heat map of all H3K27Ac peaks repressed by IL1β (>1.5 fold) 1 hour after treatment. The decreases in H3K27Ac were partially recovered by ligand activation of VDR. (B) Heat map of all H3K27Ac peaks induced by IL1β (>1.5 fold) 1 hour after treatment. The increases in H3K27Ac were partially repressed by ligand activation of VDR. (C) Enriched TF binding motifs in VDR ligand-induced H3K27Ac peaks shows that the VDR binding element (VDRE) is highly enriched. (D) H3K27Ac signal intensity around accessible VDREs (within ATAC-seq peaks) related to Cal+iBRD9-rescued IL1P-repressed genes. IL1β significantly reduces H3K27Ac at VDREs, which was rescued by Cal+iBRD9. (E) H3K27Ac signal intensity around accessible VDREs (within ATAC-seq peaks) related to Cal+iBRD9 rescued IL1β induced genes. IL1β significantly induced H3K27Ac at VDREs, which was rescued by Cal+iBRD9. (F) Genome browser tracks showing H3K27Ac at 2 loci: Camk4 and Cckar, showing IL1β causes a decrease in H3K27 acetylation, which could be reversed with Cal+iBRD9 treatment. (G) Total number of H3K27Ac peaks synergistically enhanced by iBRD9 (IL1β+Cal+iBRD9 vs. IL1β+Cal) and the fraction containing VDREs, 6 hours after treatment. (H) GO categories enriched in genes associated with peaks in (G). (I) Genome browser tracks comparing H3K27Ac between Cal and Cal+iBRD9-treated samples at Nfkbia and Camk4 loci. (J) Total number of H3K27Ac peaks synergistically repressed by iBRD9 (IL1β+Cal+iBRD9 vs. IL1β+Cal) and the fraction containing VDREs, 6 hours after treatment. (K) GO categories enriched in genes associated with peaks in (J). (L) Genome browser tracks comparing H3K27Ac between Cal and Cal+iBRD9-treated samples at Ccl28 and Txnip loci.

FIGS. 13A-13L. Activation of VDR reverses β cell stress in vivo. (A) Volcano plot of gene expression changes induced in islets isolated from Cal-treated db/db (B6) mice, determined by RNA-seq analyses, reveals the induction of key factors for β cell function, whereas multiple pro-inflammatory genes are down-regulated. (B) GO analysis shows enrichment in pathways related to β cell function in the gene set whose expression is increased in islets upon Cal treatment. (C) H&E staining of db/db (BKS) pancreata treated with vehicle or Cal for 3 months. (Scale bar: 50Rm). (D) Islet area as percentage of total pancreas sections shows increased total islet area in Cal+iBRD9-treated db/db (BKS) mice. (n=6 for vehicle, n=15 for Cal, * p<0.05, error bars show S.E.M.). (E) Average islet size in vehicle and Cal+iBRD9-treated db/db (BKS) mice. (** p<0.01). (F) Immunohistochemistry of Ki67, a proliferation marker, in vehicle and Cal+iBRD9-treated pancreas sections. Dark arrow labels Ki67+ cells within islets (Scale bar: 50 µm). (G) Bar graph showing quantification of Ki67+ cells in islets from vehicle and Cal+iBRD9-treated mice indicating an increase in proliferation in Cal+iBRD9-treated islets. (H) Immunofluorescent staining of insulin (red) in pancreas sections from vehicle, Cal and Cal+iBRD9-treated db/db (BKS) mice. (Scale bar: 50 µm). (I) Immunofluorescent staining of insulin (red) and glucagon (green) in pancreas sections from vehicle and Cal+iBRD9 treated low-dose STZ-treated mice (Scale bar: 50 µm). (J) Bar graphs showing the percentage of 1 and a cells in vehicle and Cal+iBRD9-treated db/db (BKS) mice. (K) Transmission electron microscopic images of healthy human islets 24 hours after treatment with vehicle, IL1β, IL1β+Cal, or IL1β+Cal+iBRD9. IL1β caused multiple subcellular morphological changes such as loss of dense insulin granules (upper right) and dilated ER (lower right). Activation of VDR partially rescues the morphological degeneration caused by IL1β. (Scale bar: 1 µm). (L) Schematic representation of the mechanism underlying the synergy between Cal and iBRD9 in directing the association of VDR with alternate chromatin remodeling complexes and the consequential effects on transcription. Data reported as mean±SEM, *p<0.05, **p<0.01.

SEQUENCE LISTING

Figures 1A, 1B:
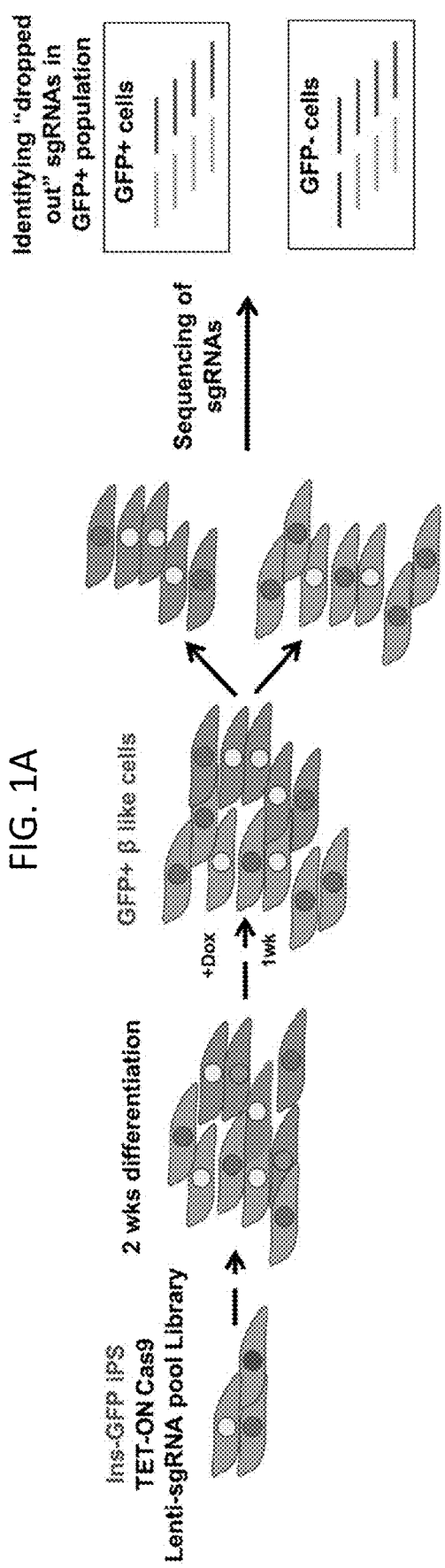
FIGS. 1A-1F. VDR is essential for § cell homeostasis. (A) Schematic representation of the genome-wide CRISPR loss-of-function screen in human iPSC-derived β-like cells. (B) Gene ontology analysis of targets compromising β-like cell function (p<0.01, 156 total genes). (C) p-value rank order plot of genes enriched in the loss-of-function screen, VDR is labeled in red. (D) Distribution of normalized reads of individual sgRNAs in GFP sorted cells; VDR sgRNAs are labeled in red. (E) Immunohistochemistry staining of pro-insulin in VDR$^{+/-}$ or VDR$^{-/-}$ islets (scale bar: 100 µm). (F) Serum proinsulin/insulin ratio in VDR$^{+/-}$ and VDR$^{-/-}$ male mice measured by ELISA (n=3, error bars S.E.M, * p<0.05).

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 31, 2019, 9 KB, which is incorporated by reference herein. In the accompanying sequence listing:
SEQ ID NOS: 1-44 are PCR primers.
SEQ ID NOS: 45-50 show exemplary T-box sequences from related nuclear receptors.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a VDR agonist" includes single or plural agonists and is considered equivalent to the phrase "comprising at least one VDR agonist." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as Jul. 24, 2017. All references and GenBank® Accession numbers cited herein are incorporated by reference in their entireties.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

Administration: To provide or give a subject an agent, such as a VDR agonist and a BRD9 antagonist, by any effective route. Exemplary routes of administration include, but are not limited to, oral, injection (such as subcutaneous, intramuscular, intradermal, intraperitoneal, intravenous, intra-articular, and intrathecal), sublingual, rectal, transdermal, intranasal, vaginal and inhalation routes.

Bromodomain-containing protein 9 (BRD9): A protein containing a bromodomain, which recognizes acetylated lysines on post-translationally modified proteins. This protein is upregulated in multiple cancer cell lines. It is closely related to BRD7. Sequences are publicly available, for example from the GenBank® database, such as GenBank® Accession Nos. NP_076413.3, NP_001304880.1, NP_001009877.2, NP_001019679.2, and NP_001180021.1 (proteins), and NM_001317951.1, NM_023924.4, and NM_001024508.3 (nucleic acids).

Diabetes mellitus: A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 2 diabetes results from insulin resistance, a condition in which cells fail to use insulin properly, sometimes combined with an absolute insulin deficiency. This form is also called "non-insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and in some examples diagnosed by demonstrating any one of:

a. Fasting plasma glucose level ≥7.0 mmol/l (126 mg/dl);
b. Plasma glucose ≥11.1 mmol/l (200 mg/dL) two hours after a 75 g oral glucose load as in a glucose tolerance test;
c. Symptoms of hyperglycemia and casual plasma glucose≥11.1 mmol/l (200 mg/dl);
d. Glycated hemoglobin (Hb A1C)≥6.5%

Effective amount or therapeutically effective amount: The amount of agent, such as a VDR agonist and a BRD9 antagonist, that is an amount sufficient to prevent, treat (including prophylaxis), reduce, and/or ameliorate the symptoms and/or underlying causes of any of a disorder or disease. In one embodiment, an "effective amount" is sufficient to reduce or eliminate a symptom of type II diabetes in a mammal, for example by lowering blood glucose.

Mammal: This term includes both human and non-human mammals. Similarly, the term "subject" includes both human and veterinary subjects (such as cats, dogs, cows, and pigs) and rodents (such as mice and rats).

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15$^{th}$ Edition (1975), describes compositions and formulations suitable for pharmaceutical delivery of the one or more VDR agonists and one or more BRD9 antagonists.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Subject: Any mammal, such as humans, non-human primates, pigs, sheep, cows, dogs, cats, rodents and the like which is to be the recipient of the particular treatment, such as treatment with a VDR agonist and a BRD9 antagonist. In two non-limiting examples, a subject is a human subject or a murine subject. In some examples, the subject has type 2 diabetes. In some examples, the subject has elevated blood glucose.

Treating a disease: "Treatment" refers to a therapeutic intervention that ameliorates a sign or symptom of a disease or pathological condition (for instance, fibrosis) after it has begun to develop. "Prevention" refers to inhibiting the full development of a disease, for example in a person who is known to have a predisposition to a disease such as a person who has been or is at risk for developing type II diabetes.

Vitamin D: A group of fat-soluble secosteroid prohormones and hormones, the two major forms of which are vitamin D2 (ergocalciferol), and vitamin D3 (cholecalciferol) which is converted to 1α,25 dihydroxyvitamin $D_3$ (1 α,25-$(OH)_2$-D3), also known as calcitriol, the physiologically active form of vitamin D.

Vitamin D agonist or analog: Any compound, synthetic or natural, that binds to and activates the VDR, such as a VDR ligand (e.g., calcitriol), VDR agonist precursor, vitamin D analogs, vitamin D precursors.

Specific, non-limiting examples of natural and synthetic vitamin D agonists and analogs include 1α,25$(OH)_2D_3$, calcipotriol, LG190090, LG9190119, LG190155, LG190176, and LG190178 (see, for instance, Boehm et al., (1999) *Chemistry & Biology*, 6:265-275); LY2108491, and LY2109866 (Ma et al., (2006) *J Clin. Invest.*, 116:892-904); 2β-(3-Hydroxypropoxy)1α,25-Dihydroxyvitamin $D_3$ (ED-71) (Tsurukami et al., (1994) *Calcif Tiss. Int.* 54:142-149); EB1089 (Pepper et al., (2003) *Blood*, 101:2454-2460); OCT (22-oxa-calcitrol) (Makibayashi et al., (2001) *Am. J. Path.*, 158:1733-1741); (1αOH-2,19-nor-25hydroxyvitamin$D_3$) and (1,3-Deoxy-2-CHCH$_2$OH-19-nor-25-hydroxyvitaminD3) (Posner et al., (2005) *Bioorganic & Medicinal Chemistry*, 13:2959-2966) and any of the vitamin D analogs disclosed in Rey et al., (1999) *J. Organic Chem.*, 64:3196-3206; and bile acid derivatives such as lithochoic acid (LCA) and ursodoxycholic acid (UDCA) (see, for instance, Nehring et al., (2007) *PNAS*, 104:10006-10009; Makishima et al., (2002) *Science,* 296:1313-1316; Copaci et al., (2005) *Rom. J. Gastroenterol.,* 14:259-266). Each of these references is hereby incorporated by reference in its entirety.

Vitamin D precursor: A compound capable of being converted to an agonist of the vitamin D receptor by an enzyme. In certain, non-limiting examples, that enzyme is CYP27B1. Specific, non-limiting examples of vitamin D precursors include vitamin $D_3$ (cholecalciferol), 25-hydroxy-vitamin $D_3$ (25-OH-$D_3$) (calcidiol), as well as vitamin D2 (ergocalciferol) and its precursors.

Vitamin D receptor (VDR): A member of the nuclear hormone receptor (NHR) superfamily and is a key regulator of calcium homeostasis and skeletal health. VDR possesses the common nuclear receptor structure, for example, is comprised of an N-terminal activation domain, a DNA-binding region (DBD) with two zinc finger domains, a hinge region and a ligand-binding domain (LBD). VDR activated gene transcription requires initial nuclear translocation via importin-α, heterodimerization with RXR, and binding to response elements present in target genes. VDR regulates genes associated with the maintenance of calcium and phosphate homeostasis in the intestine and kidney. The signal initiated by VDR/RXR heterodimers is modulated by the association of co-activating or co-repressing proteins and also depends on other signaling partners in the nuclear compartment. The VDR/RXR heterodimer is non-permissive, in that the presence or absence of RXR ligands is not known to affect VDR responses.

Endogenous activators of the VDR include the biologically active form of vitamin D (1α,25(OH)$_2$D3 (calcitriol)) and bile acids such as lithocholic acid (LCA) and its derivatives (LCA-acetate, LCA-formate, 3-keto LCA).

Overview

The primary cause of disease progression in type 2 diabetes (T2D) is inflammatory stress-induced β cell dysfunction; however, preservation of β cell function under diabetic conditions remains challenging. It is shown herein that the vitamin D receptor (VDR) is a key modulator of the inflammatory response in β cells. It was found that a ligand-dependent switch between the BAF and PBAF chromatin remodeling complexes is mediated by the alternate binding of bromodomain-containing proteins 9 (BRD9) and BRD7, respectively, to acetylated VDR. Mechanistically, BRD9 inhibition synergistically cooperates with ligand-dependent VDR activation to abrogate cytokine-induced transcriptomic changes, in part via PBAF-mediated changes in chromatin accessibility and enhancer landscape. The inventors show that combined VDR activation and BRD9 inhibition significantly restores β cell function to ameliorate hyperglycemia in multiple murine T2D models. These results establish the VDR-BRD9 as a central hub in orchestrating β cell anti-inflammatory responses and demonstrate its therapeutic use in treatment of T2D.

Figure 13J:
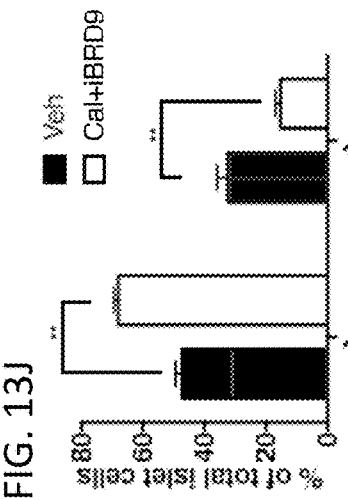
Figure 13L:
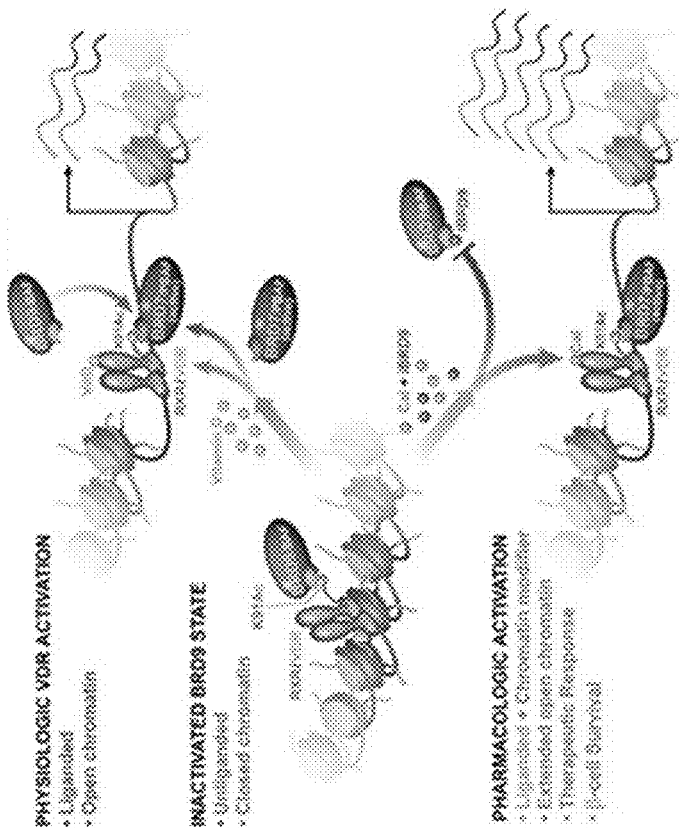

It is shown herein that VDR is a critical factor in β cell survival and function. Initially identified in an unbiased CRISPR knockout screen, genetic loss-of-function and ex vivo gain-of-function demonstrate a protective role for VDR in β cells and the modulation of islet stress. In exploring the regulatory mechanisms of VDR-driven transcriptional action the shuttling of VDR between competing chromatin remodeling complexes was observed (FIG. 13L). Specifically, provided is a novel acetylated lysine in VDR that facilitates its recognition by the highly related bromodomain reader proteins, BRD9 and BRD7, respective components of the BAF and PBAF complexes. It is shown that VDR shuttles between BAF and PBAF complexes in a ligand-dependent fashion. In addition, a highly selective BRD9 inhibitor, iBRD9, cooperates with VDR ligand to favor PBAF complex binding and significantly potentiates VDR signaling. Mechanistically, binding of the PBAF complex enhances chromatin accessibility at consensus VDR binding elements to modulate the expression of key inflammatory response genes including the inhibitor of NF-kB, Nfkbia.

Despite many shared components, the BAF and PBAF complexes are distinct assemblies (Hodges et al., 2016, Cold Spring Harbor Prespect. Med. 6. a026930). While the PBAF complex is a superior transcriptional activator compared to the BAF complex in vitro (Lemon et al., 2001, Nature 414, 924-928; Rafati et al., 2011, PLoS biology 9, e1001206), the ability of these two complexes to mediate ligand-dependent signaling was not previously known. The inventors describe herein a novel mechanism in which acetylation at K91 in VDR is recognized by the BRD7/9 subfamily of bromodomain proteins to direct the association of the PBAF and BAF complexes in a ligand-dependent fashion. Fortuitously, the switching of VDR's partner from BAF-BRD9 to PBAF-BRD7 can also be pharmacologically manipulated by targeting the "reader" of VDR acetylation, thereby providing an additional level of nuclear receptor signaling regulation.

Pro-inflammatory cytokines such as IL1β and TNF-α are detrimental to β cell function (Nackiewicz et al., 2014, Diabetologia 57, 1645-1654) and multiple clinical trials targeting these cytokines are ongoing (Imai et al., 2013, Trends Endocrinol. Metab. 24, 351-360). However, use of selective inhibitors of inflammation to treat T2D has seen only modest improvements. In contrast, it is shown herein that exploiting VDR as a negative modulator of NFκB signaling in β cells is highly effective, and that combining a VDR activator with a BRD9 inhibitor results in prolonged suppression of the damaging effects of inflammatory insults.

While multiple therapies aimed at improving β cell function are in the clinic or under development, chronic stress-induced damage to β cells poses a serious challenge for long term therapeutic efficacy (Zhou et al., 2016, Nature reviews 12, 337-346). By focusing on the VDR shuttle between BAF and PBAF complexes, provided herein is a novel therapeutic strategy to suppress inflammation via sustained receptor activation in β cells. This method demonstrates the power of genomic reprogramming, tackling the problem at the genome-wide level. As this is how β cells limit chronic inflammation, exploiting the power of the VDR, its acetylation, and the safety of its ligands offer a very different approach in the treatment of T2D.

Based on these observations, provided here are methods of reducing blood glucose in a mammal. Such methods can include administering a therapeutically effective amount of one or more VDR agonists to the mammal, and administering a therapeutically effective amount of one or more BRD9 antagonists to the mammal, thereby reducing the blood glucose. In some examples, blood glucose is decreased by of at least 5%, at least 10%, at least 25%, or at least 50%, for example as compared to administration of no VDR agonists and no BRD9 antagonists (e.g., administration of PBS).

In addition, provided are methods of treating type 2 diabetes in a mammal. Such methods can include administering a therapeutically effective amount of one or more VDR agonists to the mammal, and administering a therapeutically effective amount of one or more BRD9 antagonists to the mammal, thereby treating the type 2 diabetes in the mammal.

Provided are methods of reducing fed and fasting blood glucose. Such a method can include administering a therapeutically effective amount of one or more VDR agonists to the mammal, and administering a therapeutically effective amount of one or more BRD9 antagonists to the mammal, thereby reducing fed and fasting blood glucose. In some examples, the fed and fasting blood glucose is reduced in the treated mammal by at least 10%, at least 20%, at least 30%, at least 50%, at least 75%, or at least 90% as compared to an absence of administration of the VDR agonists and BRD9 antagonists.

In addition, provided are methods of treating an autoimmune disease. Such methods can include administering a therapeutically effective amount of one or more VDR agonists to the mammal having an autoimmune disease, and administering a therapeutically effective amount of one or more BRD9 antagonists to the mammal, thereby treating the autoimmune disease. An autoimmune disease is one in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces. Exemplary autoimmune diseases affecting mammals that can be treated with the disclosed combination of VDR agonist and BRD9 antagonist include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, and pernicious anemia.

In addition, provided are methods of reducing fed and fasting blood glucose, increasing insulin sensitivity, increasing glucose tolerance, increasing insulin secretion, increasing beta cell function, increasing the size of islets, reducing beta cell death, increasing insulin granules, or combinations thereof. Such methods can include administering a therapeutically effective amount of one or more VDR agonists to a mammal (such as one with type II diabetes), and administering a therapeutically effective amount of one or more BRD9 antagonists to the mammal, thereby reducing fed and fasting blood glucose, increasing insulin sensitivity, increasing glucose tolerance, increasing insulin secretion, increasing beta cell function, increasing the size of islets, reducing beta cell death, increasing insulin granules, or combinations thereof. In some examples, the fed and fasting blood glucose is reduced in the treated mammal by at least 10%, at least 20%, at least 30%, at least 50%, at least 75%, or at least 90% as compared to an absence of administration of the VDR agonist(s) and BRD9 antagonist(s). In some examples, insulin sensitivity is increased in the treated mammal by at least 10%, at least 20%, at least 30%, at least 50%, at least 75%, at least 90%, at least 100%, at least 200%, at least 300% or at least 500%, as compared to an absence of administration of the VDR agonist(s) and BRD9 antagonist(s). In some examples, glucose tolerance is increased in the treated mammal by at least 10%, at least 20%, at least 30%, at least 50%, at least 75%, at least 90%, at least 100%, at least 200%, at least 300% or at least 500%, as compared to an absence of administration of the VDR agonist(s) and BRD9 antagonist(s). In some examples, insulin secretion is increased in the treated mammal by at least 10%, at least 20%, at least 30%, at least 50%, at least 75%, at least 90%, at least 100%, at least 200%, at least 300% or at least 500%, as compared to an absence of administration of the VDR agonist(s) and BRD9 antagonist(s). In some examples, beta cell function is increased in the treated mammal by at least 10%, at least 20%, at least 30%, at least 50%, at least 75%, at least 90%, at least 100%, at least 200%, at least 300% or at least 500%, as compared to an absence of administration of the VDR agonist(s) and BRD9 antagonist(s). In some examples, the size or number of islets is increased in the treated mammal by at least 10%, at least 20%, at least 30%, at least 50%, at least 75%, at least 90%, at least 100%, at least 200%, at least 300% or at least 500%, as compared to an absence of administration of the VDR agonist(s) and BRD9 antagonist(s). In some examples, beta cell death is reduced in the treated subject by at least 10%, at least 20%, at least 30%, at least 50%, at least 75%, or at least 90% as compared to an absence of administration of the VDR agonist(s) and BRD9 antagonist(s). In some examples, insulin granules (e.g., the amount or number of) is increased in the treated mammal by at least 10%, at least 20%, at least 30%, at least 50%, at least 75%, at least 90%, at least 100%, at least 200%, at least 300% or at least 500%, as compared to an absence of administration of the VDR agonist(s) and BRD9 antagonist(s). In some examples, combinations of these reductions are achieved.

In addition, provided are methods of reducing fibrosis, such as fibrosis of the liver, pancreas, or kidney. Such methods can include administering therapeutically effective amounts of one or more VDR agonists to a mammal (such as one with type II diabetes), and administering a therapeutically effective amount of one or more BRD9 antagonists to the mammal, thereby reducing fibrosis. In some examples, fibrosis is reduced in the treated mammal by at least 10%, at least 20%, at least 30%, at least 50%, at least 75%, or at least 90% as compared to an absence of administration of the VDR agonist(s) and BRD9 antagonist(s).

In some examples, the disclosed methods of administering a therapeutically effective amount of one or more VDR agonists to a mammal, and administering a therapeutically effective amount of one or more BRD9 antagonists to the mammal treats a disease, such as a liver disease, kidney disease, or pancreatic disease in the subject. Examples of liver diseases that can be treated using the disclosed methods include one or more of alcohol liver disease, fatty liver disease, liver fibrosis/cirrhosis, biliary fibrosis/cirrhosis, liver cancer, hepatitis B virus infection, hepatitis C virus infection, sclerosing cholangitis, Budd-Chiari syndrome, jaundice, nonalcoholic steatohepatitis, hemochromatosis, and Wilson's disease. In some examples the liver cancer is a hepatocellular carcinoma, cholangiocarcinoma, angiosarcoma, or hemangiosarcoma. Examples of pancreatic diseases that can be treated with the disclosed methods include but are not limited to pancreatitis, pancreatic fibrosis and pancreatic ductal adenocarcinoma (PDA). In some examples, the kidney disease is fibrosis of the kidney.

The disclosed methods can further include administering one or more additional therapeutic compounds, such as those used to regulate insulin, blood sugar, or reduce inflammation, such as insulin, an alpha-glucosidase inhibitor, amylin agonist, dipeptidyl-peptidase 4 (DPP-4) inhibitor, meglitinide, sulfonylurea, or a peroxisome proliferator-activated receptor (PPAR)-gamma agonist.

In some examples, the subject is a mammal, such as a human, cat, or dog. In some examples, the subject has diabetes. Methods of administration are routine, and can include subcutaneous, intraperitoneal, intrathecal, intramuscular, or intravenous injection or infusion. In some examples, use of VDR agonists with BRD9 antagonists does not lead to (or significantly reduces, such as a reduction of at least 20%, at least 50%, at least 75%, or at least 90%) the adverse side effects observed with thiazolidinediones (TZDs) therapeutic insulin sensitizers, including weight gain, increased liver steatosis and bone fractures (e.g., reduced effects on bone mineral density, trabecular bone architecture and cortical bone thickness).

In some examples, the one or more VDR agonists and one or more BRD9 antagonists are administered concurrently. In some examples, the one or more VDR agonists and one or more BRD9 antagonists are administered sequentially. In some examples, the therapeutically effective amount of the one or more VDR agonists is at least 0.01 mg/kg, such as at least 0.1 mg/kg, or at least 0.5 mg/kg. In some examples, the therapeutically effective amount of the one or more BRD9 antagonists is at least 0.1 mg/kg, such as at least 1 mg/kg, or at least 10 mg/kg. In some examples, the one or more VDR agonists, one or more BRD9 antagonists, or both, are part of a nanoparticle.

In some examples the VDR agonist (or composition containing such) can increase the biological activity of the VDR by at least 25%, at least 50%, at least 75%, at least 90%, at least 95%, at least 100%, at least 200%, at least 300%, at least 400% or at least 500%, as compared to the biological activity in the absence of the compound. Thus in one example, a compound that increases the biological activity of a VDR protein can decrease fasting blood glucose by at least 10%, at least 20%, at least 25%, at least 30%, at least 40%, at least 50%, at least 75%, at least 80%, or at least 90%, as compared to an absence of the agonist. In one example, VDR agonist activity is determined by monitoring expression of VDR target genes such as Cyp24A1. Thus, in some examples the VDR agonist (or composition containing such) can increase Cyp24A1 expression by at least 25%, at least 50%, at least 75%, at least 90%, at least 95%, at least 100%, at least 200%, at least 300%, at least 400% or at least 500%, as compared to the biological activity in the absence of the compound. In some embodiments, the VDR agonist is not significantly degraded by Cyp24A1.

Examples of VDR agonists include but are not limited to: vitamin D, a vitamin D precursor, a vitamin D analog, a vitamin D receptor ligand, a vitamin D receptor agonist precursor, or combinations thereof. Specific examples of VDR agonists include but are not limited to calcipotriol, 25-hydroxy-$D_3$ (25-OH-$D_3$) (calcidiol); vitamin D3 (cholecalciferol); vitamin D2 (ergocalciferol), 1,α25-dihydroxyvitamin $D_3$ (calcitriol), and combinations thereof.

A BRD9 antagonist need not completely inhibit BRD9 protein activity. In some examples, such compounds reduce BRD9 protein activity by at least 10%, at least 20%, at least 25%, at least 40%, at least 50%, at least 75%, at least 80%, at least 90%, at least 95%, or at least 99%. In some examples, a BRD9 antagonist binds in the pocket of BRD9 where the acetylated lysine (K-91) binds. Examples of BRD9 antagonists include but are not limited to: I-BRD-9, TP742, BI-7273, BI-9564, dBRD9, GNE-375 and LP-99.

In some examples, the one or more VDR agonists comprises calcipotriol and the one or more BRD9 antagonists comprises I-BRD9.

Also provided are compositions that include one or more VDR agonists, and one or more BRD9 antagonists. In some examples, the one or more VDR agonists, and one or more BRD9 antagonists, or both, are part of a nanoparticle. Examples of nanoparticles that can be used in the disclosed compositions and methods include, but are not limited to those provided in US Publication Nos. 20130287688, 20130287857, 20100233251, 20100092425, 20120027808, 20080226739, and 20050215507 and U.S. Pat. Nos. 7,427,394, 8,343,497, 8,562,998, 7,550,441, 7,727,969, 8,343,498, and 8,277,812, all herein incorporated by reference. In some examples the nanoparticle is a lipid or polymeric nanoparticle. In a specific example, the nanoparticle includes a linear-dendritic hybrid polymer for encapsulating biologically active materials, comprising: a ligand for a predetermined target; a dendron; and a polyethylene glycol (PEG) chain linking the ligand to the dendron. In some examples the nanoparticle includes on its surface one or more of albumin (such as BSA), retinol binding protein, mannose-6-phosphase modified albumin, a fatty acid ester, a retinyl ester, and a linear-dendritic hybrid polymer. In some examples, the nanoparticle is between about 0.1 nm and 5000 nm in diameter, such as 1-100 nm, 0.1-1 nm, 5-20 nm, 5-15 nm, 10-5,000 nm, 20-1,000 nm, 10-500 nm, 10-200 nm, 10-150 nm, 10-100 nm, 10-25 nm, 20-40 nm, or 10, 15, 20, 25, 35, 45, 50, 75, 100, 150 or 200 nm in diameter In some examples, the composition includes a pharmaceutically acceptable carrier.

Also provided are kits that include one or more VDR agonists, and one or more BRD9 antagonists, for example in the same or separate containers. In some examples, the one or more VDR agonists, and one or more BRD9 antagonists, or both, are part of a nanoparticle. In one example, the nanoparticle is or includes a lipid nanoparticle and/or a polymeric nanoparticle. Such compositions and kits can further include at least one additional therapeutic compound, such as insulin, an alpha-glucosidase inhibitor, amylin agonist, dipeptidyl-peptidase 4 (DPP-4) inhibitor, meglitinide, sulfonylurea, or a peroxisome proliferator-activated receptor (PPAR)-gamma agonist. Exemplary PPAR-gamma agonists include a thiazolidinedione (TZD), aleglitazar, farglitazar, muraglitazar, and tesaglitazar. Exemplary TZDs include pioglitazone, rosiglitazone, rivoglitazone, and troglitazone. Other exemplary additional compounds are provided herein.

Treatment Using VDR Agonists and BRD9 Antagonists

Methods of using a combination VDR agonist and BRD9 antagonist are provided. One or more VDR agonists and one or more BRD9 antagonists, such as 1, 2, 3, 4 or 5 different VDR agonists and 1, 2, 3, 4 or 5 different BRD9 antagonists (such as one VDR agonist and one BRD9 antagonist), can be administered in therapeutically effective amounts, for example to reduce blood glucose, reduce fed and fasting blood glucose, reduce fibrosis, increase insulin sensitivity, increase glucose tolerance, increase insulin secretion, increase beta cell function, increase the size of islets, reduce beta cell death, increase insulin granules or combinations thereof, in a mammal. For example, such methods can be used to treat a disease, for example type II diabetes, an autoimmune disease, or fibrosis (such as fibrosis of the liver, pancreas or kidney). In fact, such methods are useful to treat any disease or condition where increased VDR activity is beneficial. In some examples, such effects are observed for at least one week after treatment, at least two weeks after treatment, at least three weeks after treatment, at least one month after treatment, at least five weeks after treatment, at least six weeks after treatment, at least seven weeks after treatment, at least eight weeks after treatment, or at least two months after treatment (such as after a single dose of a VDR agonist and a single dose of a BRD9 antagonist). In some examples, such effects are observed within 1 week after treatment, within 2 weeks after treatment, within 3 weeks after treatment, within 4 weeks after treatment, within 5 weeks after treatment, within 6 weeks after treatment, within 7 weeks after treatment, within 8 weeks after treatment, within 9 weeks after treatment, within 10 weeks after treatment, within 11 weeks after treatment, or within 12 weeks after treatment (such as after a single dose of a VDR agonist and a single dose of a BRD9 antagonist).

The one or more VDR agonists and one or more BRD9 antagonists can be administered to humans or other mammals by any means, including orally, intravenously, intramuscularly, intraperitoneally, intranasally, intradermally, intrathecally, subcutaneously, via inhalation or via suppository. In one non-limiting example, the one or more VDR agonists and one or more BRD9 antagonists are administered via injection. Administration can be systemic or local. In some examples, site-specific administration of the composition can be used, for example by administering one or more VDR agonists and one or more BRD9 antagonists to pancreas tissue (for example by using a pump, or by implantation of a slow release form at the site of the pancreas). The particular mode of administration and the dosage regimen can be selected by the attending clinician, taking into account the particulars of the case. Treatment can involve daily or multi-daily (e.g., twice daily, 3× daily, 4× daily), or less than daily (e.g., twice weekly, every other week, monthly, every 7 days, every 10 days, every 14 days, every 30 days, every 60 days, etc.) doses over a period of a few days, few weeks, to months, or even years. For example, a therapeutically effective amount of one or more VDR agonists and one or more BRD9 antagonists can be administered in a single dose, twice daily, twice a week, three times a week, weekly, every other week, or in several doses, for example daily, or during a course of treatment. In a particular non-limiting example, treatment involves once daily dose, twice daily dose, once weekly dose, every other week dose, or monthly dose.

The amount of VDR agonist(s) and BRD9 antagonist(s) administered can be dependent on the subject being treated, the severity of the affliction, and the manner of administration. Within these bounds, the formulation to be administered will contain a quantity of the VDR agonist(s) and BRD9 antagonist(s) in amounts effective to achieve the desired effect in the subject being treated. For example, a therapeutically effective amount of VDR agonist(s) and BRD9 antagonist(s) can be the amount of each necessary to treat diabetes, treat fibrosis, treat an autoimmune disease, or reduce blood glucose levels (for example a reduction of at least 5%, at least 10% or at least 20%, for example relative to no administration of VDR agonist(s) and BRD9 antagonist(s)).

In some examples, the VDR agonist(s) and BRD9 antagonist(s) are administered in combination (such as sequentially or simultaneously or contemporaneously) with one or more other agents, such as those useful in the treatment of diabetes or insulin resistance (e.g., insulin), those useful in the treatment of fibrosis (e.g., one or more nuclear receptor ligands), or those useful in the treatment of autoimmune disorders (e.g., steroid such as prednisone, immunosuppressants).

Anti-diabetic agents are generally categorized into six classes: biguanides (e.g., metformin); thiazolidinediones (including rosiglitazone (Avandia®), pioglitazone (Actos®), rivoglitazone, and troglitazone); sulfonylureas; inhibitors of carbohydrate absorption; fatty acid oxidase inhibitors and anti-lipolytic drugs; and weight-loss agents. Any of these agents can also be used in the methods or compositions disclosed herein. Exemplary anti-diabetic agents include those disclosed in *Diabetes Care,* 22(4):623-634. One class of anti-diabetic agents of use is the sulfonylureas. Another class of anti-diabetic agents is the biguanide antihyperglycemics. Other examples are provided herein.

In some examples, the VDR agonist(s) and BRD9 antagonist(s) can be administered in combination with effective doses of anti-diabetic agents (such as biguanides, thiazolidinediones, or incretins) and/or lipid lowering compounds (such as statins or fibrates). The terms "administration in combination," "co-administration," or the like, refer to both concurrent and sequential administration of the active agents. Administration of the VDR agonist(s) and BRD9 antagonist(s), may also be in combination with lifestyle modifications, such as increased physical activity, low fat diet, low sugar diet, and smoking cessation.

Additional agents that can be used in combination with the VDR agonist(s) and BRD9 antagonist(s) include, without limitation, anti-apoptotic substances such as the Nemo-Binding Domain and compounds that induce proliferation such as cyclin dependent kinase (CDK)-6, CDK-4 and Cyclin D1. Other active agents can be utilized, such as antidiabetic agents for example, insulin, metformin, sulphonylureas (e.g., glibenclamide, tolbutamide, glimepiride), nateglinide, repaglinide, thiazolidinediones (e.g., rosiglitazone, pioglitazone), peroxisome proliferator-activated receptor (PPAR)-gamma-agonists (such as C1262570) and antagonists, PPAR-gamma/alpha modulators (such as KRP 297), alpha-glucosidase inhibitors (e.g., acarbose, voglibose), Dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMGCoA) reductase inhibitors (such as a statin), insulin and insulin analogues, GLP-1 and GLP-1 analogues (e.g., exendin-4) or amylin. In some embodiments the agent is an immunomodulatory factor such as anti-CD3 mAb, growth factors such as HGF, vascular endothelial growth factor (VEGF), platelet-derived growth factor (PDGF), lactogens, or parathyroid hormone-related protein (PTHrP).

In some embodiments, methods are provided for treating diabetes or pre-diabetes in a subject by administering a therapeutically effective amount of a composition including the VDR agonist(s) and BRD9 antagonist(s), to the subject. The subject can have T2D. The subject can be any mammalian subject, including human subjects and veterinary subjects such as cats and dogs. The subject can be a child or an adult. The subject can also be administered insulin. The method can include measuring blood glucose levels.

In some examples, the method includes selecting a subject with diabetes, such as T2D, or a subject at risk for diabetes, such as a subject with pre-diabetes. These subjects can be selected for treatment with the VDR agonist(s) and BRD9 antagonist(s). In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An OGTT two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in *Standards of Medical Care in Diabetes*—2010 (American Diabetes Association, *Diabetes Care* 33:S11-61, 2010).

In some examples, the subject treated with the VDR agonist(s) and BRD9 antagonist(s) has HbA1C of greater than 6.5% or greater than 7%.

In some examples, treating diabetes (such as T2D) includes one or more of increasing glucose tolerance (such as an increase of at least 5%, at least 10%, at least 20%, or at least 50%, for example relative to no administration of the VDR agonist(s) and BRD9 antagonist(s)), decreasing insulin resistance (for example, decreasing plasma glucose levels, decreasing plasma insulin levels, or a combination thereof, such as decreases of at least 5%, at least 10%, at least 20%, or at least 50%, for example relative to no administration of the VDR agonist(s) and BRD9 antagonist(s)), decreasing serum triglycerides (such as a decrease of at least 10%, at least 20%, or at least 50%, for example relative to no administration of the VDR agonist(s) and BRD9 antagonist(s), decreasing free fatty acid levels (such as a decrease of at least 5%, at least 10%, at least 20%, or at least 50%, for example relative to no administration of the VDR agonist(s) and BRD9 antagonist(s)), and decreasing HbA1c levels in the subject (such as a decrease of at least 0.5%, at least 1%, at least 1.5%, at least 2%, or at least 5% for example relative to no administration of the VDR agonist(s) and BRD9 antagonist(s)). In some embodiments, the disclosed methods include measuring glucose tolerance, insulin resistance, plasma glucose levels, plasma insulin levels, serum triglycerides, free fatty acids, and/or HbA1c levels in a subject.

In some examples, administration of the VDR agonist(s) and BRD9 antagonist(s) treats T2D or pre-diabetes, by decreasing of HbA1C, such as a reduction of at least 0.5%, at least 1%, or at least 1.5%, such as a decrease of 0.5% to 0.8%, 0.5% to 1%, 1 to 1.5% or 0.5% to 2%. In some examples the target for HbA1C is less than about 6.5%, such as about 4-6%, 4-6.4%, or 4-6.2%. In some examples, such target levels are achieved within about 26 weeks, within about 40 weeks, or within about 52 weeks. Methods of measuring HbA1C are routine, and the disclosure is not limited to particular methods. Exemplary methods include HPLC, immunoassays, and boronate affinity chromatography.

In some examples, administration of the VDR agonist(s) and BRD9 antagonist(s) treats diabetes or pre-diabetes by increasing glucose tolerance, for example, by decreasing blood glucose levels (such as two-hour plasma glucose in an OGTT or FPG) in a subject. In some examples, the method includes decreasing blood glucose by at least 5% (such as at least 10%, at least 15%, at least 20%, at least 25%, at least 30%, at least 35%, or more) as compared with a control (such as no administration of any of insulin, VDR agonist(s), or BRD9 antagonist(s). In particular examples, a decrease in blood glucose level is determined relative to the starting blood glucose level of the subject (for example, prior to treatment with the VDR agonist(s) and BRD9 antagonist(s). In other examples, decreasing blood glucose levels of a subject includes reduction of blood glucose from a starting point (for example greater than about 126 mg/dL FPG or greater than about 200 mg/dL OGTT two-hour plasma glucose) to a target level (for example, FPG of less than 126 mg/dL or OGTT two-hour plasma glucose of less than 200 mg/dL). In some examples, a target FPG may be less than 100 mg/dL. In other examples, a target OGTT two-hour plasma glucose may be less than 140 mg/dL. Methods to measure blood glucose levels in a subject (for example, in a blood sample from a subject) are routine.

In other embodiments, the disclosed methods include comparing one or more indicators of diabetes (such as glucose tolerance, triglyceride levels, free fatty acid levels, or HbA1c levels) to a control (such as no administration of insulin, VDR agonist(s) or BRD9 antagonist(s)), wherein an increase or decrease in the particular indicator relative to the control (as discussed above) indicates effective treatment of diabetes. The control can be any suitable control against which to compare the indicator of diabetes in a subject. In some embodiments, the control is a sample obtained from a healthy subject (such as a subject without diabetes). In some embodiments, the control is a historical control or standard reference value or range of values (such as a previously tested control sample, such as a group of subjects with diabetes, or group of samples from subjects that do not have diabetes). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

Treatment or Prevention of Fibrosis

In some examples, the disclosed methods can be used to reduce fibrosis (for example by decreasing the fibrotic content of a fibrotic liver, kidney or pancreas). Thus, in some examples, the method reduces fibrosis (for example by decreasing the fibrotic content of a fibrotic liver, kidney or pancreas) by at least 10%, at least 20%, at least 25%, at least 40%, at least 50%, at least 75%, at least 80%, at least 90%, or at least 95%, as compared to an absence of the treatment with the VDR agonist(s) and BRD9 antagonist(s). In some examples, the disclosed methods are prophylactic. For example, the method can include administering a subject at risk for developing fibrosis a therapeutic composition that includes a VDR agonist(s) and a BRD9 antagonist(s). Such prophylactic administration can delay the onset of the symptoms of fibrosis of the liver, kidney or pancreas. For example, prophylactic administration of a composition that includes a VDR agonist(s) and BRD9 antagonist(s) can be used to prevent the onset of one or more symptoms or features of fibrosis. For example, as an organ undergoes fibrosis, the functional cellular mass of the organ is reduced as it is replaced by scar tissue (collagens and other abnormal matrix components). In addition, fibrosis causes architectural disorganization that can diminish function and lead to pathology, such as portal hypertension and increased risk of hepatocellular carcinoma in the case of the liver. Severe portal hypertension usually manifests as bleeding esophageal/gastric varices and/or ascities. In the kidney and pancreas the features of advanced fibrosis are renal failure and endocrine and/or exocrine pancreatic failure.

The VDR agonist(s) and BRD9 antagonist(s) can be used for treatment of fibrosis in combination with other therapeutic agents, such as chemotherapies and biotherapies. In one example, the other therapeutic agents include one or more nuclear receptor ligands, including but not limited to ligands for peroxisome proliferator-activated receptor-gamma (PPAR-γ, NR1C3), peroxisome proliferator-activated receptor-alpha (PPAR-α, NR1C1) and peroxisome proliferator-activated receptor-delta (PPAR-δ, NR1C2), farnesoid X receptor (FXR, NR1H4), interferon-gamma (IFN-γ), angiotensin converting enzyme inhibitors, angiotensin II receptor antagonists, ursodeoxycholic acid (UDCA), curcumin, anti-oxidants including, but not limited to vitamin E, retinoids such as Vitamin A, and therapies that deliver proteases to the liver to degrade pathological ECM. In some examples, other therapeutic agents are part of a composition provided herein.

Exemplary VDR Agonists

The disclosed methods and compositions use or include one or more VDR agonists (such as a VDR ligand) that can bind to and activate the VDR. VDR agonists include but are not limited to 1α,25(OH)$_2$-D3 and precursors and analogs thereof, VDR ligands, and VDR agonist precursors. The disclosure is not limited to particular vitamin D agonists. A variety of biologically active vitamin D agonists are contemplated.

In some examples, 1α,25(OH)$_2$D$_3$ or a vitamin D precursor or analog is used as a VDR agonist. It is not necessary to use the most biologically active form of vitamin D to achieve a beneficial therapeutic effect. The naturally occurring ligand of the vitamin D receptor is calcitriol. In one embodiment, precursors of calcitriol (such as calcidiol) are administered to a subject, and are then converted within the target cell population to calcitriol.

In addition, hepatic stellate cells (HSCs) express CYP24A1, a cytochrome P450 enzyme that terminates the biological effect of calcitriol by side chain hydroxylation. Thus, in one embodiment, a VDR ligand or other VDR agonist or agonist precursor that is resistant to deactivation by CYP24A1 is used to achieve more effective and longer lasting VDR activation in target cell populations. In specific examples, the VDR ligand is one that can be activated by CYP27B1 while being resistant to deactivation by CYP24A1.

Exemplary VDR agonists include those molecules that activate the VDR. Methods of determining if an agent is a VDR agonist are routine. For example, induction of CYP24A1 expression can be measured in cells that express VDR after contact with the agent, wherein an increase in CYP24A1 expression (such as a 10- to 20-fold increase in expression) indicates that the agent is a VDR agonist. Other methods include transfected reporter gene constructs and FRET assays. In some examples, binding of an agonist to a purified LBD is detected by measuring induced recruitment for coactivator peptides (e.g., LXXLL). For example VDR agonists can increase CYP24A1 expression in a VDR-expressing cell by at least 20%, at least 50%, at least 75%, at least 80%, at least 90% at least 100%, at least 200% or even at least 1000% or more as compared to the absence of the agonist.

VDR agonists include vitamin D compounds, precursors and analogs thereof. Vitamin D compounds include, but are not limited to compounds which have at least one of the following features: the C-ring, D-ring and 3β-hydroxycyclohexane A-ring of vitamin D interconnected by the 5,7 diene double bond system of vitamin D together with any side chain attached to the D-ring (e.g., compounds with a 'vitamin D nucleus' and substituted or unsubstituted A-, C-, and D-rings interconnected by a 5,7 diene double bond system typical of vitamin D together with a side chain attached to the D-ring).

Vitamin D analogs include those non-secosteroid compounds capable of mimicking various activities of the secosteroid calcitriol. Examples of such compounds include, but are not limited to, LG190090, LG190119, LG190155, LG190176, and LG1900178 (See, Boehm et al., *Chemistry & Biology* 6:265-275, 1999).

Vitamin D compounds include those vitamin D compounds and vitamin D analogs which are biologically active in vivo, or are acted upon in a mammalian subject such that the compound becomes active in vivo. Examples of such compounds include, but are not limited to: vitamin D, calcitriol, and analogs thereof [e.g., 1α-hydroxyvitamin D$_3$ (1α-OH-D$_3$), 1,25-dihydroxyvitamin D$_2$ (1,25-(OH)$_2$D$_2$), 1α-hydroxyvitamin D$_2$ (1α-OH-D$_2$), 1α,25-(OH)$_2$-16-ene-D$_3$, 1α,25-(OH)$_2$-24-oxo-16-ene-D$_3$, 1α,24R(OH)$_2$-D$_3$, 1α,25(OH)$_2$-22-oxa-D$_3$, 20-epi-22-oxa-24a,24b,-dihomo-1α,25(OH)$_2$-D$_3$, 20-epi-22-oxa-24a,26a,27a,-trihomo-1α25(OH)$_2$-D$_3$, 20-epi-22-oxa-24homo-1α,25(OH)$_2$-D$_3$, 1,25-(OH)$_2$-16,23E-diene-26-trifluoro-19-nor-D$_3$, and nonsecosteroidal vitamin D mimics.

In one example, the VDR agonist is one or more of the following vitamin D, 1,α25 dihydroxyvitamin D$_3$, calcipotriol, 1α-hydroxyvitamin D$_3$, 1,25-dihydroxyvitamin D$_2$, 1α-hydroxyvitamin D$_2$, 1α,25-(OH)$_2$-16-ene-D$_3$, 1α,25-(OH)$_2$-24-oxo-16-ene-D$_3$, 1α,24R(OH)$_2$-D3, 1α,25(OH)$_2$-22-oxa-D$_3$, 20-epi-22-oxa-24a,24b,-dihomo-1α,25(OH)$_2$-D$_3$, 20-epi-22-oxa-24a,26a,27a,-trihomo-1α25(OH)$_2$-D$_3$, 20-epi-22-oxa-24homo-1α,25(OH)$_2$-D$_3$, and 1,25-(OH)$_2$-16,23E-diene-26-trifluoro-19-nor-D$_3$.

In a one embodiment, the biologically active vitamin D compound is selected from 1,α25-dihydroxyvitamin D$_3$, 19-nor-1,25-dihydroxyvitamin D$_2$, 19-nor-1,25-dihydroxy-21-epi-vitamin D$_3$, 1,25-dihydroxy-24-homo-22-dehydro-22E-vitamin D$_3$, and 19-nor-1,25-dihydroxy-24-homo-22-dehydro-22E-vitamin D$_3$, and non-secosteroidal vitamin D mimics. In an additional example, the biologically active VDR agonist is selected from the analogs represented by the following formula:

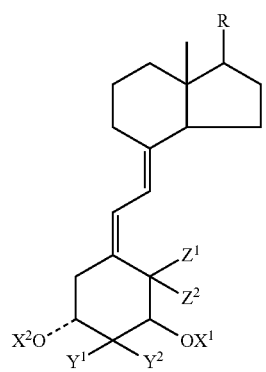

wherein $X^1$ and $X^2$ are each selected from the group consisting of hydrogen and acyl; wherein $Y^1$ and $Y^2$ can be H, or one can be O-aryl or O-alkyl while the other is hydrogen and can have a β or α configuration, $Z^1$ and $Z^2$ are both H, or $Z^1$ and $Z^2$ taken together are CH$_2$; and wherein R is an alkyl, hydroxyalkyl or fluoroalkyl group, or R may represent the following side chain:

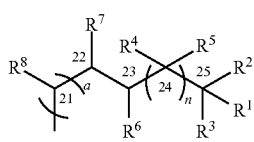

wherein (a) may have an S or R configuration and wherein $R^1$ represents hydrogen, hydroxy or O-acyl, $R^2$ and $R^3$ are each selected from the group consisting of alkyl, hydroxyalkyl and fluoroalkyl, or, when taken together represent the group —$(CH_2)m$- where (m) is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or, $R^4$ and $R^5$ taken together represent double-bonded oxygen, $R^6$ and $R^7$ taken together form a carbon-carbon double bond and $R^8$ may be H or $CH_3$, and wherein (n) is an integer having a value of from 1 to 5, and wherein the carbon at any one of positions 20, 22, or 23 in the side chain may be replaced by an O, S, or N atom.

In one example, the VDR agonists do not cause symptoms of hypercalcemia when administered to a subject. In another example, the VDR agonists do not generate as much (i.e., a lesser degree) of a calcemic response as compared to calcitriol when administered to a subject. In one example, VDR agonists have low calcemic response characteristics as compared to calcitriol. In another embodiment, these compounds are selected from $1\alpha,25\text{-}(OH)_2\text{-}24\text{-epi-}D_2$, $1\alpha,25\text{-}(OH)_2\text{-}24a\text{-Homo-}D_3$, $1\alpha,25\text{-}(OH)_2$ $24a\text{-Dihomo-}D_3$, $1\alpha,25\text{-}(OH)_2\text{-}19\text{-nor-}D_3$, and $20\text{-epi-}24\text{-homo-}1\alpha,25\text{-}(OH)_2\text{-}D_3$.

Other exemplary VDR agonists that can be used are provided in Table 1.

TABLE 1

1,25-$(OH)_2D_3$ and its synthetic analogs (taken from Nagpal et al., *Endocr. Rev.* 2005;26:662-687).

Vitamin D Analogs

TABLE 1-continued
1,25-(OH)$_2$D$_3$ and its synthetic analogs (taken from Nagpal et al., *Endocr. Rev.* 2005;26:662-687).
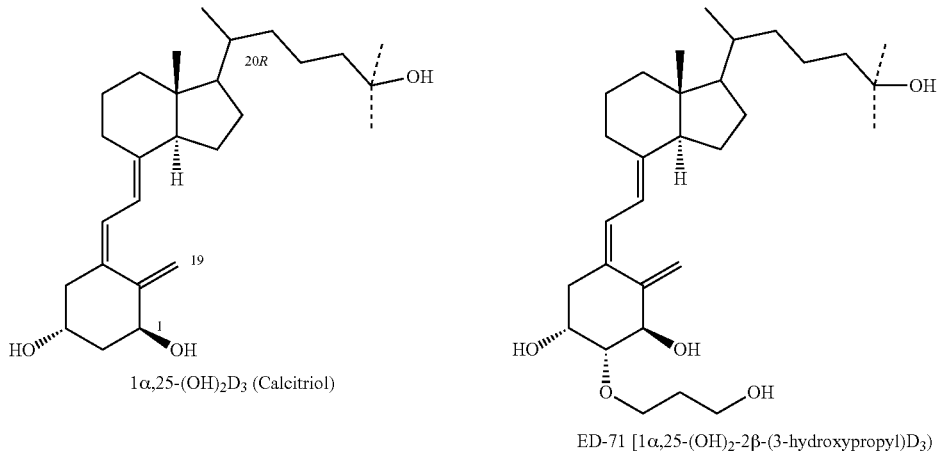
1α,25-(OH)$_2$D$_3$ (Calcitriol)
ED-71 [1α,25-(OH)$_2$-2β-(3-hydroxypropyl)D$_3$)
"20-Epi Vitamin D Analogs"
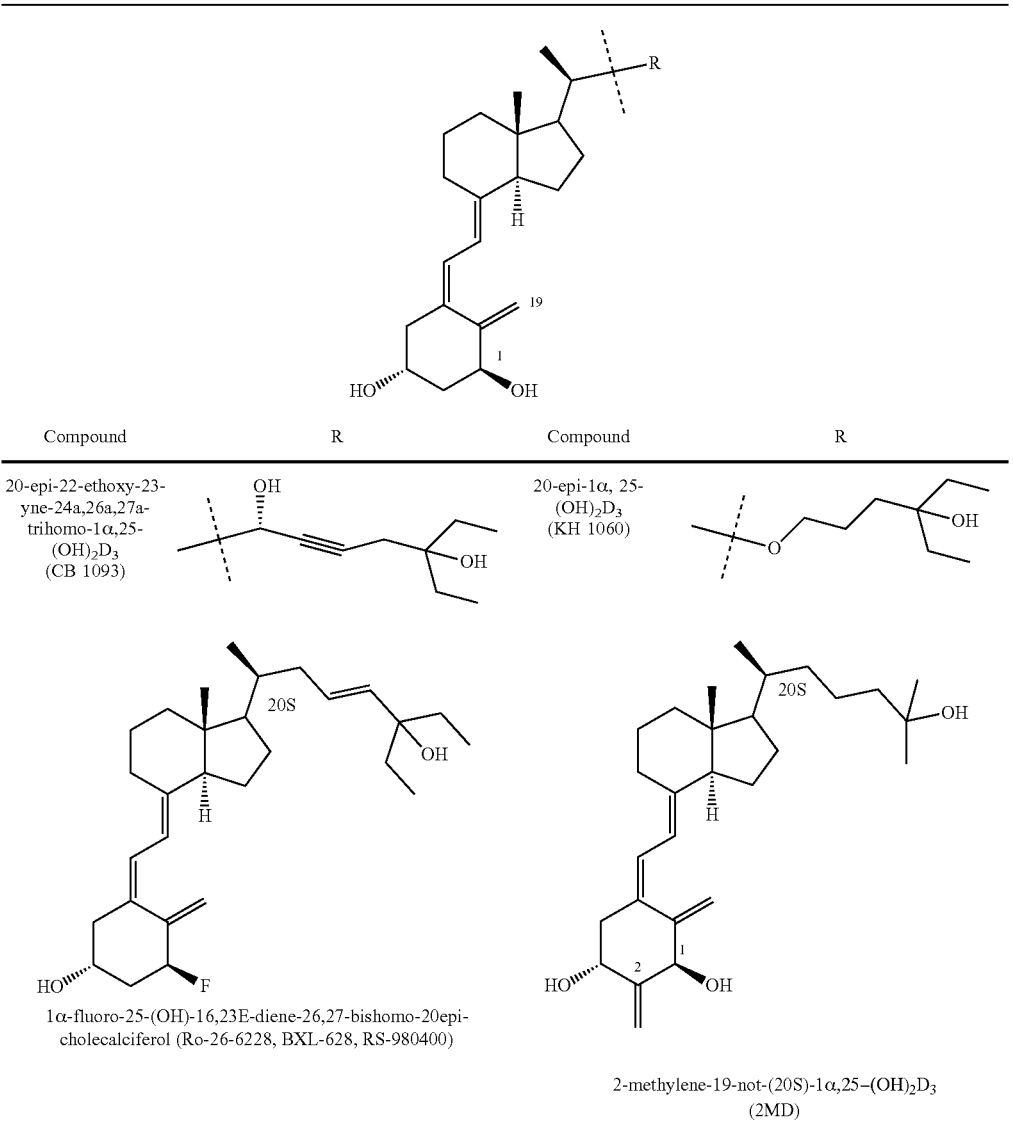
| Compound | R | Compound | R |
|---|---|---|---|
| 20-epi-22-ethoxy-23-yne-24a,26a,27a-trihomo-1α,25-(OH)$_2$D$_3$ (CB 1093) | | 20-epi-1α, 25-(OH)$_2$D$_3$ (KH 1060) | |
1α-fluoro-25-(OH)-16,23E-diene-26,27-bishomo-20epi-cholecalciferol (Ro-26-6228, BXL-628, RS-980400)
2-methylene-19-not-(20S)-1α,25-(OH)$_2$D$_3$ (2MD)

In one example, therapeutically effective doses of vitamin D2 and D3 range, from about 50 IU to about 50,000 IU. In some embodiments, vitamin D2 and/or D3 is administered in an oral dose of, for example, less than about 75 IU, about 100 IU, about 250 IU, about 500 IU, about 750 IU, about 1,000 IU, about 1,500 IU, about 2,000 IU, about 2,500 IU, about 5,000 IU, about 7,500 IU, about 10,000 IU, about 15,000 IU, about 20,000 IU, about 25,000 IU, about 40,000 IU, or about 50,000 IU, or more. In other embodiments, calcitriol is administered in a dose of from 0.001 to 10 micrograms. For instance, calcitrol is administered, in some embodiments, in a dose of about 0.01 µg, about 0.05 µg, about 0.1 µg, about 0.25 µg, about 0.5 µg, about 1 µg, about 5 µg, or about 10 µg.

In one example, the VDR agonist is cholecalciferol or calcidiol. In some examples, a higher dose than usual is administered, but with less frequency, for example, 50,000 to 500,000 units weekly.

In another embodiment, if the VDR agonist is not a 1α-hydroxy compound, a daily dose between 1.0 and 100 µg per day per 160 pound patient is administered, such as between 5.0 and 50 µg per day per 160 pound patient. In a different embodiment, if the biologically active vitamin D compound is a 1α-hydroxy compound, a daily dose of between 0.1 and 20 µg per day per 160 pound patient is administered, while a preferred dose is between 0.5 and 10µ per day per 160 pound patient. In a particular example, the dose is between 3-10 µg per day.

BRD9 Antagonists

The disclosed methods and compositions use or include one or more BRD9 antagonists. In some examples, the BRD9 antagonist is specific for BRD9. BRD9 antagonists include but are not limited to I-BRD9, TP742, BI-7273, BI-9564, dBRD9, GNE-375 and LP-99, as well as BRD9 antagonists provided in Remillard et al., *Angew. Chem. Int. Ed.* 56:1-7, 2017 and Theodoulou et al., *J. Med. Chem.* 99:1425-39, 2016 (all herein incorporated by reference).

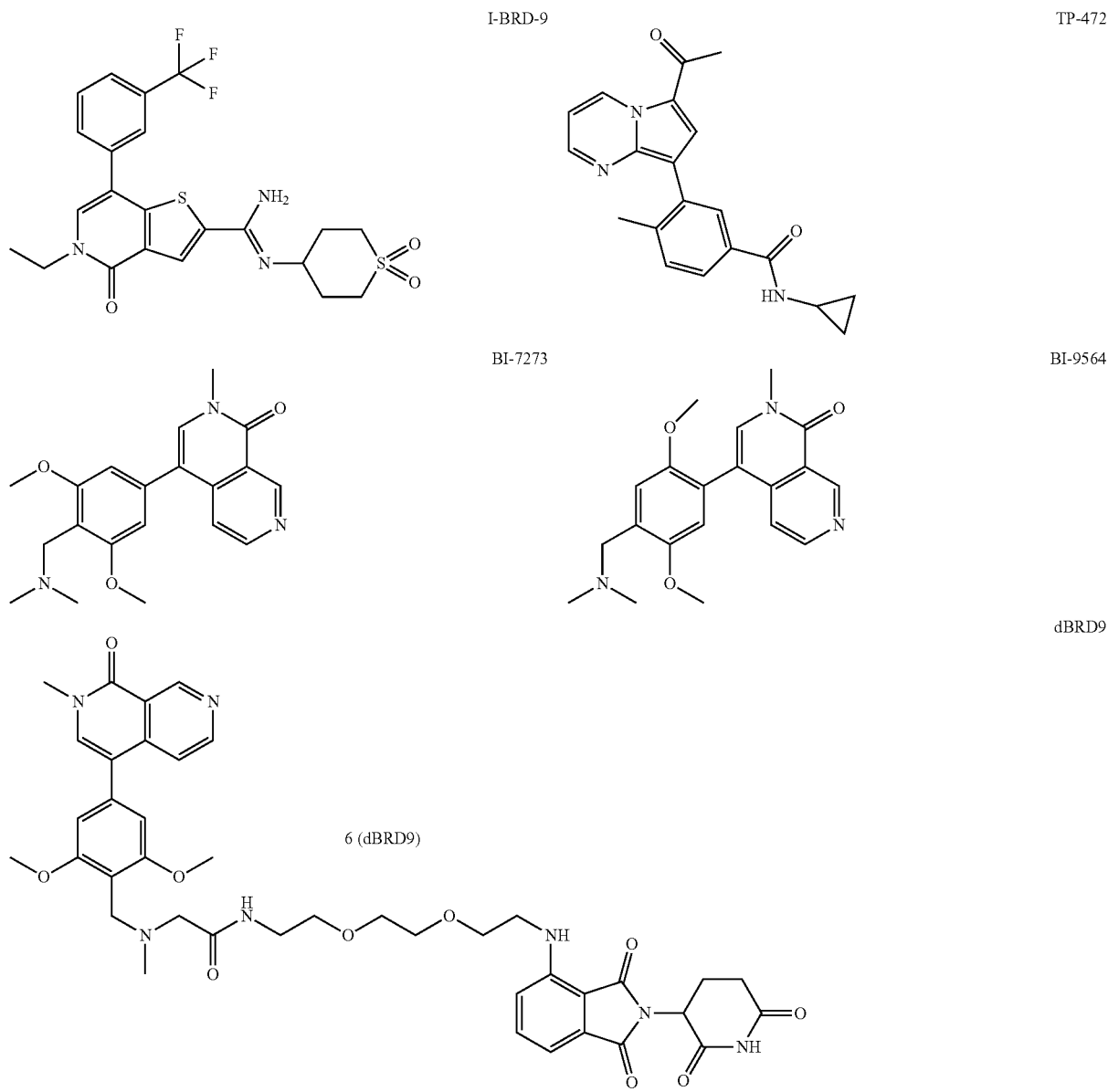

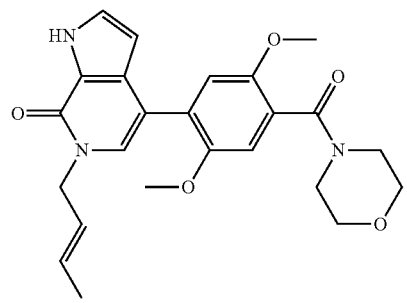

GNE-375

C<sub>24</sub>H<sub>27</sub>N<sub>3</sub>O<sub>5</sub>
Mol. Wt. 437.49

-continued

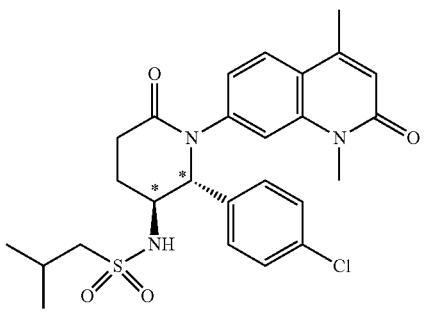

LP99

The disclosure is not limited to particular BRD9 antagonists. A variety of biologically active BRD9 antagonists are contemplated.

Methods of determining if an agent is a BRD9 antagonist are known. For example, the TR-FRET methods described in Theodoulou et al., J. Med. Chem. 99:1425-39, 2016 can be used. Briefly, compounds can be incubated with Alexa Fluor647 ligand (GSK2833930A) in Greiner 384-well black low volume microtitre plates and incubated in the dark for 30 min at room temperature. Detection reagents can include Eu-W1024 Anti-6xHis antibody. The plates can be read to determine donor and acceptor counts. From this, the ratio of acceptor/donor is calculated ($\lambda ex=337$ nm, $\lambda em$ donor=615 nm, em acceptor=665 nm) and used for data analysis. For example BRD9 antagonists can decrease BRD9 activity by at least 20%, at least 50%, at least 75%, at least 80%, at least 90% at least 100%, at least 200% or even at least 1000% or more as compared to the absence of the antagonist.

Pharmaceutical Compositions

Pharmaceutical compositions that include one or more VDR agonists, and one or more BRD9 antagonists, are provided. In some examples, the one or more VDR agonists, and one or more BRD9 antagonists, or both, are part of a nanoparticle. Such compositions can be formulated with an appropriate pharmaceutically acceptable carrier, depending upon the particular mode of administration chosen.

Additional therapeutic agents, such as agents for the treatment of diabetes, can be included. Thus, the pharmaceutical compositions can include a therapeutically effective amount of another agent. Other active agents can be utilized, such as antidiabetic agents for example one or more of: insulin, metformin, meglitinide, sulphonylureas (e.g., glibenclamide, tolbutamide, glimepiride), nateglinide, repaglinide, thiazolidinediones (e.g., rosiglitazone, pioglitazone), an alpha-glucosidase inhibitor, a amylin agonist, peroxisome proliferator-activated receptor (PPAR)-gamma-agonists (such as C1262570, aleglitazar, farglitazar, muraglitazar, tesaglitazar, and TZD) and PPAR-γ antagonists, PPAR-gamma/alpha modulators (such as KRP 297), alpha-glucosidase inhibitors (e.g., acarbose, voglibose), dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMGCoA) reductase inhibitors (such as a statin), insulin and insulin analogues, GLP-1 and GLP-1 analogues (e.g. exendin-4) or amylin. Exemplary TZDs that can be part of the composition include pioglitazone, rosiglitazone, rivoglitazone, and troglitazone.

The pharmaceutically acceptable carriers and excipients useful in this disclosure are conventional. See, e.g., Remington: The Science and Practice of Pharmacy, The University of the Sciences in Philadelphia, Editor, Lippincott, Williams, & Wilkins, Philadelphia, Pa., 21$^{st}$ Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, proteins, such as human serum albumin or plasma preparations.

Preparations for parenteral administration can include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration, including topical administration of the VDR agonist(s) and BRD9 antagonist(s) compositions provided herein, can include ointments, lotions, creams, gels, drops, suppositories, sprays, liquids and powders. Conventional pharmaceutical carriers, aqueous, powder or oily bases, thickeners and the like may be necessary or desirable.

Therapeutic agents for oral administration, including oral administration of the VDR agonist(s) and BRD9 antagonist(s) compositions provided herein, include powders or granules, suspensions or solutions in water or non-aqueous media, capsules, sachets, or tablets. Thickeners, flavorings, diluents, emulsifiers, dispersing aids or binders may be included.

Therapeutic agents, including the VDR agonist(s) and BRD9 antagonist(s) composition, can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In some embodiments, the composition including one or more VDR agonists, and one or more BRD9 antagonists is included in a controlled release formulation, for example, a microencapsulated formulation. Various types of biodegradable and biocompatible polymers, methods can be used (see, for example, U.S. Patent Publication Nos. 2007/0148074; 2007/0092575; and 2006/0246139; U.S. Pat. Nos. 4,522, 811; 5,753,234; and 7,081,489; PCT Publication No. WO/2006/052285; Benita, *Microencapsulation: Methods and Industrial Applications*, $2^{nd}$ ed., CRC Press, 2006).

In other embodiments, a composition including one or more VDR agonists, and one or more BRD9 antagonists is included in a nanodispersion system. Nanodispersion systems and methods for producing such nanodispersions are known See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), poly(ethylene glycol). Exemplary low molecular weight surfactants include sodium dodecyl sulfate, hexadecyl pyridinium chloride, polysorbates, sorbitans, poly(oxyethylene) alkyl ethers, poly(oxyethylene) alkyl esters, and combinations thereof. In one example, the nanodispersion system includes PVP and ODP or a variant thereof (such as 80/20 w/w). In some examples, the nanodispersion is prepared using the solvent evaporation method, see for example, Kanaze et al., *Drug Dev. Indus. Pharm.* 36:292-301, 2010; Kanaze et al., *J. Appl. Polymer Sci.* 102:460-471, 2006.

Many types of release delivery systems for the composition including one or more VDR agonists, and one or more BRD9 antagonists can be used. Examples include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the composition is contained in a form within a matrix such as those described in U.S. Pat. Nos. 4,452,775; 4,667,014; 4,748,034; 5,239, 660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as type II diabetes and autoimmune disorders. Long-term release, as used herein, means that the implant is constructed and arranged to deliver therapeutic levels of the active ingredient for at least 30 days, such as at least 60 days. Long-term sustained release implants include some of the release systems described above (see U.S. Pat. No. 6,218, 371).

The dosage form of the pharmaceutical composition can be determined by the mode of administration chosen. For instance, in addition to injectable fluids, topical, inhalation, oral, and suppository formulations can be employed. Topical preparations can include eye drops, ointments, sprays, patches, and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Methods of preparing such dosage forms are known.

The pharmaceutical compositions that include one or more VDR agonists, and one or more BRD9 antagonists can be formulated in unit dosage form, suitable for individual administration of precise dosages. In one non-limiting example, a unit dosage contains from about 1 mg to about 1 g of one or more VDR agonists, such as about 10 mg to about 100 mg, about 50 mg to about 500 mg, about 100 mg to about 900 mg, about 250 mg to about 750 mg, or about 400 mg to about 600 mg. In other examples, a therapeutically effective amount of one or more VDR agonists protein is about 0.01 mg/kg to about 50 mg/kg, for example, about 0.05 mg/kg to about 10 mg/kg, about 0.05 mg/kg to about 0.1 mg/kg, about 0.01 mg/kg to about 0.1 mg/kg, or about 1 mg/kg to about 10 mg/kg. In one non-limiting example, a unit dosage contains from about 1 mg to about 5 g of one or more BRD9 antagonists, such as about 10 mg to about 100 mg, about 50 mg to about 500 mg, about 100 mg to about 1000 mg, about 250 mg to about 750 mg, or about 400 mg to about 800 mg. In other examples, a therapeutically effective amount of one or more BRD9 antagonists protein is about 0.01 mg/kg to about 50 mg/kg, for example, about 0.5 mg/kg to about 25 mg/kg, about 0.5 mg/kg to about 15 mg/kg, about 1 mg/kg to about 20 mg/kg, or about 1 mg/kg to about 10 mg/kg.

The disclosure is illustrated by the following non-limiting Examples.

Example 1

Materials and Methods

This example describes the materials and methods used to obtain the results described in Examples 2-8. Also see Wei et al., *Cell* 173:1-15, 2018, herein incorporated by reference in its entirety.

Differentiation of hiPSC to Human β-Like Cells

The method of Yoshihara et al. (Cell metabolism 23, 622-634, 2016) was used. Briefly, hiPSCs (derived from HUVECs and including GFP under the control of the human insulin promoter, INS-GFP) were cultured to 90% confluency in complete mTeSR Media, at which time the media was changed to 100 ng/ml Activin (R&D Systems, 338-AC), 25 ng/ml Wnt3a (R&D Systems, 5036-WN) in differentiation media (800 ml DMEM/F12, 13.28 g BSA, 10 ml Glutamax, 560 mg NaHCO3, 330 mg thiamine, 100 mg reduced glutathione, 3300 mg vitamin C, 14 µg selenium, 10 ml NEAA, 2 ml trace element B, 1 ml trace element C, 7 µl β-ME, 2 ml DLC, 2 ml GABA, 2 ml LiCl, 129.7 µg pipecolic acid, insulin 2 mg up to 1,000 ml) for 2 days and then 100 ng/ml activin in differentiation media for another 2 days. Subsequently, media was replaced with differentiation media with 1 µM dorsomorphin (Biovision, 1656-5), 2 µM retinoic acid (Sigma, R2625-1G), 10 µM SB431542 (Sigma, S4317-5MG), and 1% B27 supplement (GIBCO, 17504-044) for 7 days. Media was then replaced with 10 µM Forskolin (Sigma, F6886-25MG), 10 µM dexamethasone (Sigma, D4902-100MG), 10 µM Alk5 inhibitor II (Calbiochem, 616452 or Enzo, ALX-270-445), 10 mM nicotinamide (Sigma, 72340-100G), 1 uM 3,3',5-Triiodo-L-thyronine sodium salt (T3), and 1% B27 supplement for 10 days. At day 21, the expression of INS-GFP is confirmed regularly by fluorescence microscopy.

CRISPR Screening

"Drop off" genome-wide CRISPR screening was performed using a protocol similar to that described previously (Wang et al., 2014, *Science* 343, 80-84). A Tet-ON inducible rtTA and subsequently a genomic lentiviral sgRNA library (Wang et al., 2014, Science 343, 80-84) were transduced into an INS (human insulin promoter)-GFP iPS cell line as reported (Yoshihara et al., 2016, Cell metabolism 23, 622-634). Selection with 3 different markers (puromycin for rtTA, blasticidin for sgRNA library and neomycin for insulin-GFP), generated an iPS cell line that contained both vectors. At least $5 \times 10^7$ cells were maintained at every passage to guarantee the coverage of the library. The cells were placed under a standard differentiation protocol and the rtTA was induced after 2 weeks of differentiation, concurrent with INS-GFP expression. Doxycycline was added for 1 week. Finally, the cells were FACS-sorted by GFP expression and both GFP+ and GFP-cells from the same batch were collected, genomic DNA extracted and libraries were prepared for high throughput sequencing. The sgRNA sequences were amplified with primers described in Wang et al. (Science 343, 80-84, 2014) and sequenced by an Illumina HiSeq 2000. The sequences were aligned and analyzed by MAGeCK (Li et al., 2014, Genome biology 15, 554).

Mice

The following mice strains were from Jackson: VDR KO (B6.129S4-Vdrtm1Mbd/J), B6 db (B6.BKS(D)-Leprdb/J), BKS db (BKS.Cg-Dock7m+/+ Leprdb/J), C57BL6/J. Animals were maintained in a specific pathogen-free animal facility on a 12-hr light-dark cycle at an ambient temperature of 23° C. Water and food were provided ad lib. All animal experiments used age-matched male mice. VDR KO and control littermate mice were maintained on a VDR KO rescue diet containing 21% calcium, 0.67% phosphorus, and 20% lactose supplemented with 4.4 U vitamin D per gram diet.

Low-Dose STZ Induction 8 week old C57B16 male mice were injected intraperitoneally with streptozotocin (Sigma, S0130) at the dose of 50 mg/kg every day for 5 consecutive days. Blood glucose was measured 1 week after final injection and mice were separated into different treatment groups to ensure all groups had a similar starting glucose level.

T2D Animal Model Treatment db/db (B6) mice were grouped based on glucose levels at the age of 5 weeks. Treatments were started from 6 weeks and animals were treated with vehicle (30% 2-Hydroxypropyl-β Cyclodextrin, Sigma, H-107) or drugs 3 times a week. Calcipotriol (Tocris, 60 ug/kg) and iBRD9 (R&D, 10 mg/kg) were dissolved in 30% β-cyclodextran and injected intraperitoneally 3 times a week. For db/db (BKS) mice, treatment started from age of 10 weeks. Calcipotriol (Tocris, 30 ug/kg) and iBRD9 (R&D, 5 mg/kg) were dissolved in 30% β-cyclodextran and injected intraperitoneally 3 times a week.

RNA-Seq Library Generation

Total RNA was isolated from tissue or cell pellets using the RNA mini kit (Qiagen). Sequencing libraries were prepared from 100-500 ng total RNA using the TruSeq RNA Sample Preparation Kit v2 (Illumina) according to the manufacturer's protocol. Briefly, mRNA was purified, fragmented, and used for first-, then second-strand cDNA synthesis followed by adenylation of 3' ends. Samples were ligated to unique adapters and subjected to PCR amplification. Libraries were then validated using the 2100 BioAnalyzer (Agilent), normalized, and pooled for sequencing. RNA-Seq libraries prepared from two biological replicates for each experimental condition were sequenced on the Illumina HiSeq 2000 using bar-coded multiplexing and a 100 bp read length.

High-Throughput Sequencing and Analysis

Image analysis and base calling were performed with Illumina CASAVA-1.8.2. This yielded a median of 29.9M usable reads per sample. Short read sequences were mapped to a UCSC mm9 reference sequence using the RNA-seq aligner STAR (Dobin et al., 2013). Known splice junctions from mm9 were supplied to the aligner and de novo junction discovery was also permitted. Differential gene expression analysis, statistical testing and annotation were performed using Cuffdiff 2 (Trapnell et al., 2013). Transcript expression was calculated as gene-level relative abundance in fragments per kilobase of exon model per million mapped fragments and employed correction for transcript abundance bias (Roberts et al., 2011). RNA-Seq results for genes of interest were also explored visually using the UCSC Genome Browser.

Gene Expression Analysis by qPCR

Samples were run in triplicate and expression was normalized to the levels of the housekeeping controls Rplp0 (36b4) for human and mouse. Samples were analyzed by qPCR, using SYBR Green dye (Bio-rad). Statistical comparisons were made using Student's t test. Error bars are mean±SEM. Primers used are shown below:

```
rNfkbia FP:
                                          (SEQ ID NO: 1)
CTCTATCCATGGCTACCTGG rNfkbia RP:
                                          (SEQ ID NO: 2)
CCATTACAGGGCTCCTGAG rRela FP:
                                          (SEQ ID NO: 3)
TGTGAAGAAGCGAGACCTG rRela RP:
                                          (SEQ ID NO: 4)
TCCTCTATGGGAACTTGAAAGG
```

-continued rRelb FP:
ATCGAGCTTCGAGACTGTG
(SEQ ID NO: 5)

rRelb RP:
AGTTGTTAAAGCTGTGCCG
(SEQ ID NO: 6)

rNfkb1 FP:
GGGAGATGTGAAGATGCTG
(SEQ ID NO: 7)

rNfkb1 RP:
AAGTGTAGGACACTGTCCC
(SEQ ID NO: 8)

mCyp24A1 FP:
TGCCCTATTTAAAGGCCTGTCT
(SEQ ID NO: 9)

mCyp24A1 RP:
CGAGTTGTGAATGGCACACTT
(SEQ ID NO: 10)

mFbp1 FP:
ACGGATATCAGCACCCTGAC
(SEQ ID NO: 11)

mFbp1 RP:
ATTGGTTGAGCCAGCGATAC
(SEQ ID NO: 12)

mG6Pase FP:
GACTGTGGGCATCAATCTCC
(SEQ ID NO: 13)

mG6Pase RP:
ACAGGTGACAGGGAACTGCT
(SEQ ID NO: 14)

mPEPCK FP:
TCTCTGATCCAGACCTTCCAA
(SEQ ID NO: 15)

mPEPCK RP:
GAAGTCCAGACCGTTATGCAG
(SEQ ID NO: 16)

mIns2 FP:
TTTGTCAAGCAGCACCTTTG
(SEQ ID NO: 17)

mIns2 RP:
TCTACAATGCCACGCTTCTG
(SEQ ID NO: 18)

mCasp1 FP:
GAGAAATGAAGTTGCTGCTG
(SEQ ID NO: 19)

mCasp1 RP:
CTTTCACCATCTCCAGAGC
(SEQ ID NO: 20)

mCcl2 FP:
CAACTCTCACTGAAGCCAG
(SEQ ID NO: 21)

mCcl2 RP:
TTAACTGCATCTGGCTGAG
(SEQ ID NO: 22)

mCxcl1 FP:
CAGAGCTTGAAGGTGTTGC
(SEQ ID NO: 23)

mCxcl1 RP:
AGTGTGGCTATGACTTCGG
(SEQ ID NO: 24)

mIl1b FP:
GAAATGCCACCTTTTGACAGTG
(SEQ ID NO: 25)

mIl1b RP:
TGGATGCTCTCATCAGGACAG
(SEQ ID NO: 26)

mIl6 FP:
TAGTCCTTCCTACCCCAATTTCC
(SEQ ID NO: 27)

mIl6 RP:
TTGGTCCTTAGCCACTCCTTC
(SEQ ID NO: 28)

mNlrp3 FP:
ATCTTTGCTGCGATCAACAG
(SEQ ID NO: 29)

mNlrp3 RP:
TGATGTACACGTGTCATTCCA
(SEQ ID NO: 30)

msXBP1 FP:
GAGTCCGCAGCAGGTG
(SEQ ID NO: 31)

msXBP1 RP:
GTGTCAGAGAGTCCATGGGA
(SEQ ID NO: 32)

mUcn3 FP:
AAGTCCACTTACAGGGAGC
(SEQ ID NO: 33)

mUcn3 RP:
TAGAACTTGTGGGAGAGGC
(SEQ ID NO: 34)

mPDX1 FP:
AAATCCACCAAAGCTCACG
(SEQ ID NO: 35)

mPDX1 RP:
ATTCCTTCTCCAGCTCCAG
(SEQ ID NO: 36)

mNkx6-1 FP:
GTACTTGGCAGGACCAGAG
(SEQ ID NO: 37)

mNkx6-1 RP:
TTCTGGAACCAGACCTTGAC
(SEQ ID NO: 38)

Isolation of Pancreatic Islets

Mouse pancreatic islets were isolated as previously described (Yoshihara et al., 2010, Nat. Commun 1:127) with slight modification. Briefly, 0.5 mg/ml collagenase P (Roche REF 1213873001, diluted in HBSS buffer, GIBCO, 14170-112) was injected through the common bile duct, and the perfused pancreas dissected and incubated at 37° C. for 21 min. Digested exocrine cells and intact islets were separated via centrifugation (900×g for 15 min) over Histopaque-1077 (Sigma, H8889), and intact islets were manually selected. Human islets were provided by the Integrated Islets Distribution Program (see details below).

| IIDP Donor ID | Sex | Age (years) | Race | BMI | Cause of Death |
|---|---|---|---|---|---|
| 1448 | Male | 45 | White | 40.4 | Cerebro-vascular/stroke |
| 1503 | Male | 59 | White | 33.94 | Anoxia |
| 1741 | Male | 52 | White | 22.1 | Cerebro-vascular/stroke |

Metabolic Cage Analyses

Metabolic cage analyses were conducted with a Comprehensive Lab Animal Monitoring System (Columbus Instruments). $CO_2$ production, $O_2$ consumption, RER, and ambulatory counts by x-peak were determined for 3 consecutive days and nights, with at least 24 hr adaptation before data recording.

Histology (H&E Staining, Immunohistochemistry and Immunofluorescence)

For immunohistochemistry, FFPE tissues sections were deparaffinized and antigen retrieval performed using Vector Antigen Unmasking buffer (H3301). VectaStain ABC kit and ImmPACT DAB substrate (Vector Lab) were used to develop signal. Antibodies used: Pro-insulin (R&D, MAB13361, 1:100), insulin (Abcam, ab7842, 1:100), MAFA (Novus, NB400-137, 1:50), NKX6-1 (Cell Signaling, 54551, 1:100), and Glucagon (Abcam, ab82270, 1:100). DAPI-containing mounting media (VECTASHIELD mounting medium for fluorescence) was used for nuclear staining. Immunostaining was visualized by ZEISS 780 confocal microscopy analysis.

Immunoprecipitation

Immunoprecipitations were performed as described previously (He et al., 2010, Mol. Cell 38, 428-38). Briefly, cells are lysed using ice-cold lysis buffer (HEPES 20 mM pH8, EDTA 0.2 mM, NaCl 0.3 mM, NP40 0.5%, 15% glycerol) for 15 min, and after centrifuging the supernatant was collected. For HA- or Flag-tagged proteins, immunoprecipitations were performed using HA-magnetic beads (Pierce, P188836), or Flag-magnetic beads (Sigma, M8823) for 1.5 hr at 4° C. For other immunoprecipitations, primary antibodies were incubated with lysates for 2 hr followed by Protein A magnetic beads (Life Technologies, 10001D). After 3 washes with wash buffer (HEPES 10 mM pH8, EDTA 0.2 mM, NaCl 0.3 mM, NP40 0.1%, 15% glycerol), the beads were boiled with NuPage LDS sample buffer and the lysates were stored at $-20°$ C.

Mudpit Mass-Spec

Samples were precipitated by methanol/chloroform. Dried pellets were dissolved in 8 M urea/100 mM TEAB, pH 8.5. Proteins were reduced with 5 mM tris(2-carboxyethyl) phosphine hydrochloride (TCEP, Sigma-Aldrich) and alkylated with 10 mM chloroacetamide (Sigma-Aldrich). Proteins were digested overnight at 37° C. in 2 M urea/100 mM TEAB, pH 8.5, with trypsin (Promega). Digestion was quenched with formic acid, 5% final concentration.

The digested samples were analyzed on a Fusion Orbitrap tribrid mass spectrometer (Thermo). The digest was injected directly onto a 30 cm, 75 um ID column packed with BEH 1.7 um C18 resin (Waters). Samples were separated at a flow rate of 200 nl/min on a nLC 1000 (Thermo). Buffers A and B were 0.1% formic acid in water and acetonitrile, respectively. A gradient of 1-30% B over 90 min, an increase to 40% B over 30 min, an increase to 90% B over another 10 min and held at 90% B for a final 10 min of washing was used for 140 min total run time. Column was re-equilibrated with 20 ul of buffer A prior to the injection of sample. Peptides were eluted directly from the tip of the column and nanosprayed directly into the mass spectrometer by application of 2.5 kV voltage at the back of the column. The Orbitrap Fusion was operated in a data-dependent mode. Full MS1 scans were collected in the Orbitrap at 120K resolution with a mass range of 400 to 1600 m/z and an AGC target of 5e5. The cycle time was set to 3 sec, and within this 3 sec the most abundant ions per scan were selected for CID MS/MS in the ion trap with an AGC target of 1e4 and minimum intensity of 5000. Maximum fill times were set to 50 ms and 100 ms for MS and MS/MS scans respectively. Quadrupole isolation at 1.6m/z was used, monoisotopic precursor selection was enabled and dynamic exclusion was used with exclusion duration of 5 sec.

Protein and peptide identification were done with Integrated Proteomics Pipeline—IP2 (Integrated Proteomics Applications). Tandem mass spectra were extracted from raw files using RawConverter (ref1) and searched with ProLuCID (ref2) against rat UniProt database. The search space included all fully-tryptic and half-tryptic peptide candidates. Carbamidomethylation on cysteine was considered as a static modification. Acetylation (42.010565) was considered as a differential modification on Lysine and the N-terminus. Data was searched with 50 ppm precursor ion tolerance and 600 ppm fragment ion tolerance. Data was filtered to 10 ppm precursor ion tolerance post search. Identified proteins were filtered using DTASelect (ref3) and utilizing a target-decoy database search strategy to control the false discovery rate to 1% at the protein level.

siRNA Knock-Down Assay

INS1 cells were cultured at 37° C. in 5% C02 in air in RPMI-1640 (Sigma Aldrich) supplemented with 10% (v/v) fetal bovine serum, 1% (v/v) Antibiotic-Antimycotic (Gibco) 10 mM HEPES, 2 mM glutamax, 1 mM sodium pyruvate, and 50 μM β-mercaptoethanol (RPMI for INS1 medium). INS1 cells were transfected with Lipofectamine RNAiMAX (Invitrogen) for 24 hr, and cytokines were added for 24 hr or 1 hour. siRNAs were from GE Healthcare (VDR: L-097753-02-0005, PCAF: L-085879-02-0005, BAF180: L-088113-02-0005, non-targeting pool: D-001810-10-05).

Intraperitoneal Glucose or Insulin Tolerance Tests (TT)

Intraperitoneal GTTs were performed on overnight fasted mice. Blood glucose values were assessed before and at 0, 15, 30, 60, and 120 min after i.p. administration of 0.5 g/kg of glucose. Serum insulin levels were assessed before and at 0, 15, and 60 min after the i.p. administration of glucose using a rat/mouse Insulin ELISA kit (Millipore). IP-ITT assays were performed on mice after a 6 hr fast with an injection of 2 U/kg of insulin (Humalin R, Eli Lilly).

shRNA Knockdown shRNA constructs for human VDR, as well as control shRNA, were from Transomics. Lentiviral shRNAs were produced in 293T cells and polybrene (6 g/ml) was used in transduction. Puromycin selection was performed for 1 week at 1 ug/ml.

FACS Analysis

Annexin V staining was performed per manufacturers' instructions (Ebioscience, 88-8008-74, BD, 561126). FACS analysis were performed using BD FACSCantoII.

Antibodies

Antibodies used were: BRD9 (Bethyl A303-781A), VDR (Santa Cruz, sc1008, sc-13133), FLAG (Sigma F3165), HA (Roche, 11867423001), Lysine acetylation (Cell Signaling 9441s), GST (Santa Cruz sc-4033), PCAF (Cell Signaling 3378s), SMARCC1/2 (Cell Signaling, 11956), BRG1 (Cell Signaling 3508), PBRM1 (Bethyl, A301-591A), PHF10 (Genetex, GTX116314), ARID1B (Bethyl, A301-040A), HDAC3 (Cell Signaling 2632), KAT7 (Bethyl, A302-224A), NCOA5 (Bethyl A300-790A), THRAP3 (Bethyl A300-955A), IKBa (Cell Signaling 4814), p65 (Cell Signaling 8242), IKKb (Cell Signaling 8943), pIKKa (Cell Signaling 2697), a-Tubulin (EMD, Cp06-100), H3K4Me1 (Abcam, ab8895), H3K27Ac (Abcam, ab4729), H3K4Me3 (Abcam ab8580), NKX6-1 (Cell Signaling, 54551), Glucagon (Abcam, ab82270).

ELISA

ELISA were performed per manufacturer's instructions: mouse insulin (Millipore, EZRMI-13K), mouse proinsulin (Mercodia, NC9088881).

Chromatin Immunoprecipitation (ChIP)

INS1 cells were treated with Cal (100 nM), iBRD9 (10 uM) and/or IL1β prior to harvest for ChIP assays. The experimental procedure for ChIP was as previously described (Barish et al., 2010, Genes Dev 24:2760-5). Briefly, after fixation, nuclei from were isolated, lysed, and sheared with a Diagenode Bioruptor to yield DNA fragment sizes of 200-1,000 bp followed by immunoprecipitation.

ChIP-Seq Data Analysis

The procedure was as previously described (Barish et al., 2010, Genes Dev 24:2760-5). Briefly, short DNA reads were aligned against the mouse mm9 or rat rn4 reference genome using the Illumina CASAVA v1.8.2. Reads were aligned using the Bowtie aligner, allowing up to two mismatches in the read. Only tags that map uniquely to the genome were considered for further analysis. Subsequent peak calling and motif analysis were conducted using HOMER, a software suite for ChIP-seq analysis. The methods for HOMER, described below, have been implemented and are available at http://homer.ucsd.edu. One tag from each unique position was considered to eliminate peaks resulting from clonal amplification of fragments during the ChIP-seq protocol. Peaks were identified by searching for clusters of tags within a sliding 200 bp window, requiring adjacent clusters to be at least 1 kb away from each other. The threshold for the number of tags that determine a valid peak was selected for an FDR <0.001, as empirically determined by repeating the peak finding procedure using randomized tag positions. Peaks are required to have at least 4-fold more tags (normalized to total count) than input or immunoglobulin G control samples and 4-fold more tags relative to the local background region (10 kb) to avoid identifying regions with genomic duplications or nonlocalized binding. Differential H3K27Ac peaks are called by Homer using a threshold of 1.5 fold change and p value<0.0001. Peaks are annotated to gene products by identifying the nearest RefSeq transcriptional start site. Visualization of ChIP-seq results was achieved by uploading custom tracks onto the University of California, Santa Cruz genome browser. Gene ontology analysis were performed using Metascape (metascape.org) or DAVID (david.ncifcrf.gov).

ATAC-Seq

INS1 cells were pretreated with vehicle, Cal, iBRD9, or iBRD9 16 hrs before IL1β were added for 1 hr and $5 \times 10^4$ cells were harvested to prepare ATAC-seq libraries. Reads were aligned by Bowtie to rn4 and peaks were called by Homer using default settings. Differential peaks were called by Homer using default settings (Fold change >4, p value <0.0001).

Transmission Electronic Microscopy (TEM)

Islets in suspension were pelleted in 2% low melting point agarose and subsequently fixed in 2.5% glutaraldehyde with 2% paraformaldehyde in 0.15M cacodylate buffer containing 2 mM calcium chloride, pH 7.4, for one hour at 4° C. The pellet was trimmed down to contain the minimal amount of agarose possible, washed in buffer, and secondarily fixed in 1% osmium tetroxide/0.3% potassium ferrocyanide in buffer. Subsequently, the pellet was washed in water and en bloc stained with 2% uranyl acetate followed by a graded dehydration in ethanol (35%, 50%, 70%, 90%, 100%, 100%). Samples were then rapidly infiltrated in Spurr's resin using a Pelco BioWave microwave processing unit (Ted Pella, Redding, Calif.), embedded in Pelco Pyramid tip mold (Ted Pella, Redding, Calif.), and cured at 60° C. overnight. 70 nm ultrathin sections were then cut on a Leica UC7 ultramicrotome (Leica, Vienna) and Islets were examined on a Libra120 (Zeiss, Oberkochen, Germany) at 120V.

LC-MS Analysis

An internal standard of d4-succinate was added to all samples prior to analysis. 500 mL of methanol containing 100 pmol of d4-succinate was added to 50 uL plasma samples and vortexed for 1 min. The samples were then centrifuged at 17.000× g for 10 min at 4° C. After drying the supernatant via SpeedVac, the extract was dissolved in H2O (50 mL) and 10 mL was subjected to liquid chromatography mass spectrometry (LC-MS). Compound i-BRD9 was measured using a TSQ Quantiva mass spectrometer (Thermo) and Dionex Ultimate 3000 (Thermo) fitted with a Gemini C18 HPLC column (5 mm; 4.6 mm×50 mm, Phenomenex). LC solvents used were: solvent A, 0.1% formic acid in water; solvent B, 0.1% formic acid in acetonitrile. Separations took place over 16 min with a flow rate of 0.4 mL/min and consisted of the following steps: 5 to 50% solvent B over 9 min, 50 to 80% B over 1 min, 80% B for 1 min, 80 to 5% B over 0.1 min, and 5% B for 5 min. MS analyses were performed using electrospray ionization (ESI) in positive ion mode for i-BRD9 and negative ion mode for d4-succinate. Positive and negative mode source parameters were as follows: spray voltage 3.5 kV, ion transfer tube temperature of 325° C., and a vaporizer temperature of 275° C. Multiple reaction monitoring transitions for target compound and internal standard are shown in (Table 2).

TABLE 2

MRM transitions for target compounds and internal standard

| Compound | Polarity | Precursor (m/z) | Product (m/z) | Collision Energy (V) | RF Lens (V) |
|---|---|---|---|---|---|
| i-BRD9-1 | Positive | 498.2 | 349.1 | 30 | 120 |
| i-BRD9-2 | Positive | 498.2 | 321.0 | 46 | 120 |
| i-BRD9-3 | Positive | 498.2 | 283.0 | 55 | 120 |
| i-BRD9-4 | Positive | 498.2 | 366.0 | 30 | 120 |
| d4-succinate | Negative | 121.1 | 77.1 | 10 | 30 |

Data and Software Availability

The accession number for the RNA-seq data reported herein is NCBI SRA: SRP103617. The accession number for the ChIP-seq and ATAC-seq data is SRA: SRP103615.

Example 2

VDR is Required for β Cell Maintenance In Vitro

Figure 1C:
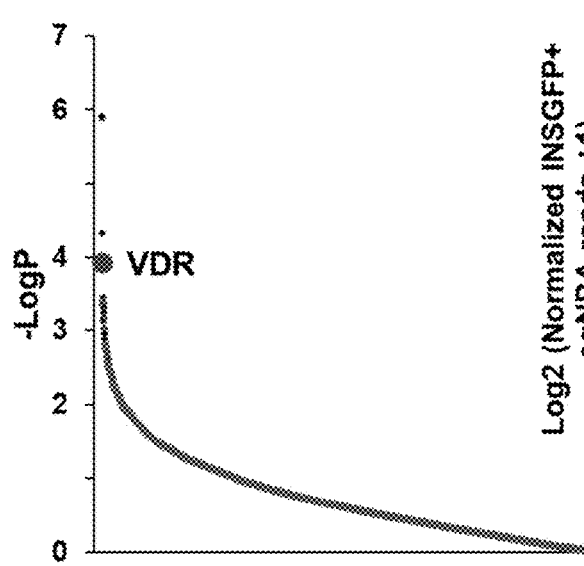
Figure 1D:
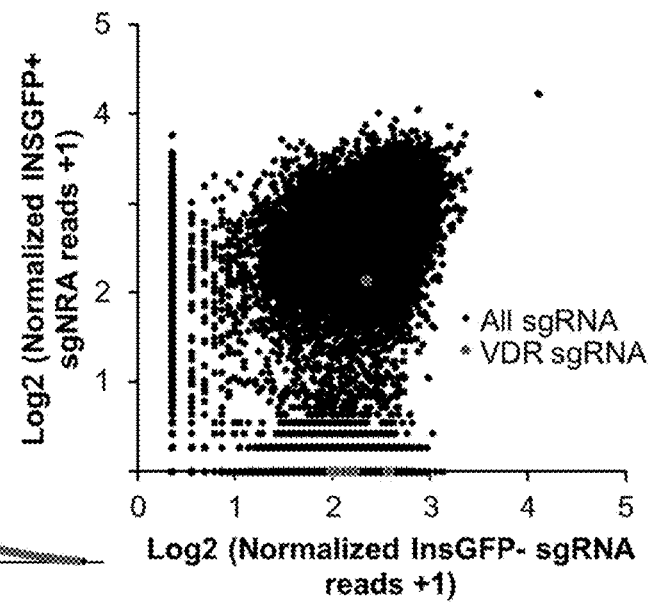
Figure 1E:
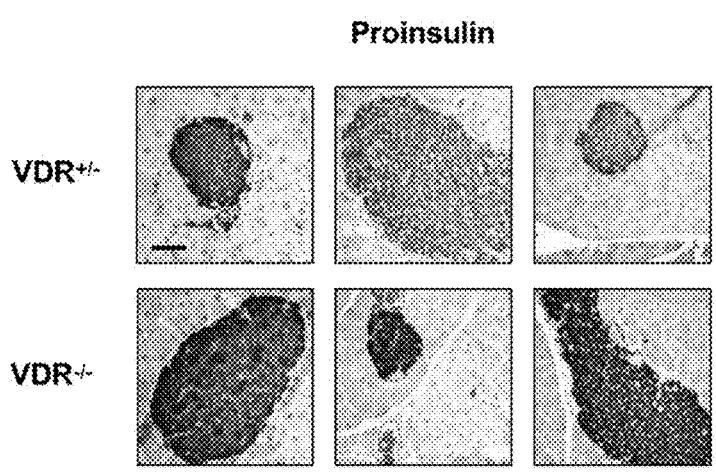
Figure 1F:
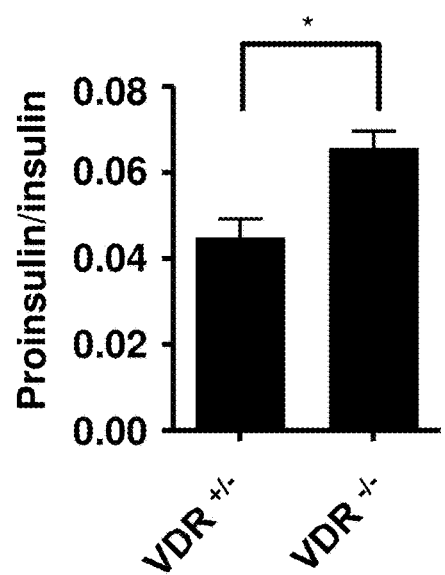
Figure 2A:
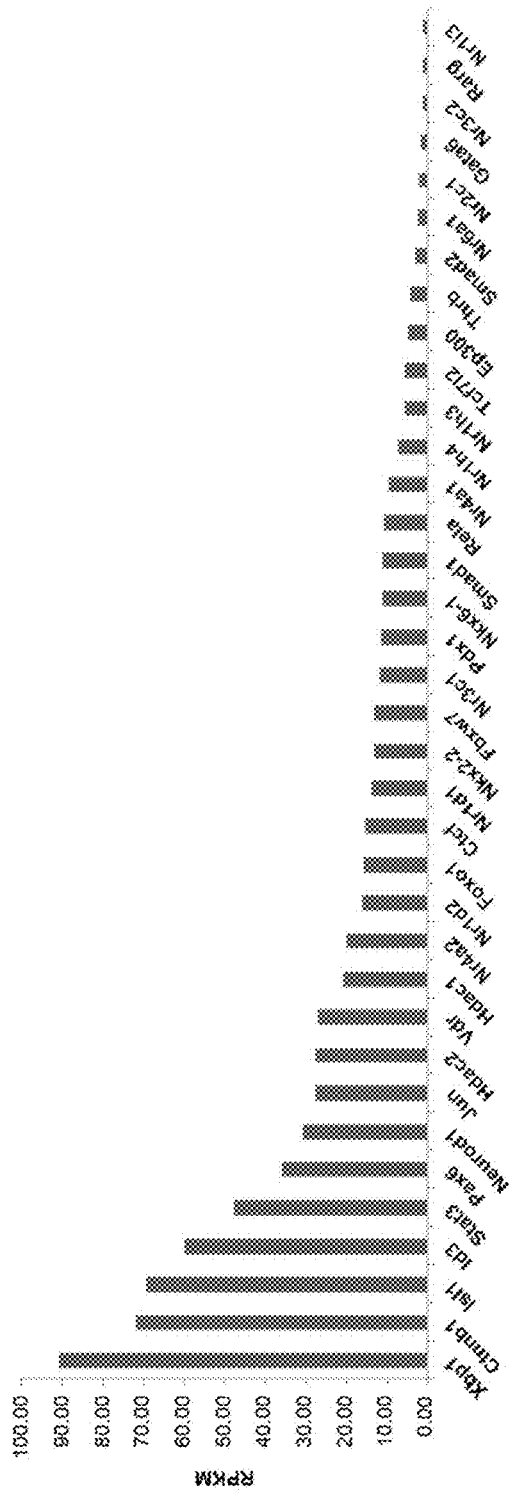
FIGS. 2A-2B. VDR is expressed in β cells. (A) Ranking of highly expressed transcription factors by average RPKM in single-cell RNA seq. Average RPKM is shown. VDR is shown in red. (B) Heat map of single cell expression values of key alpha cell and β cell markers, together with VDR.
Figure 2B:
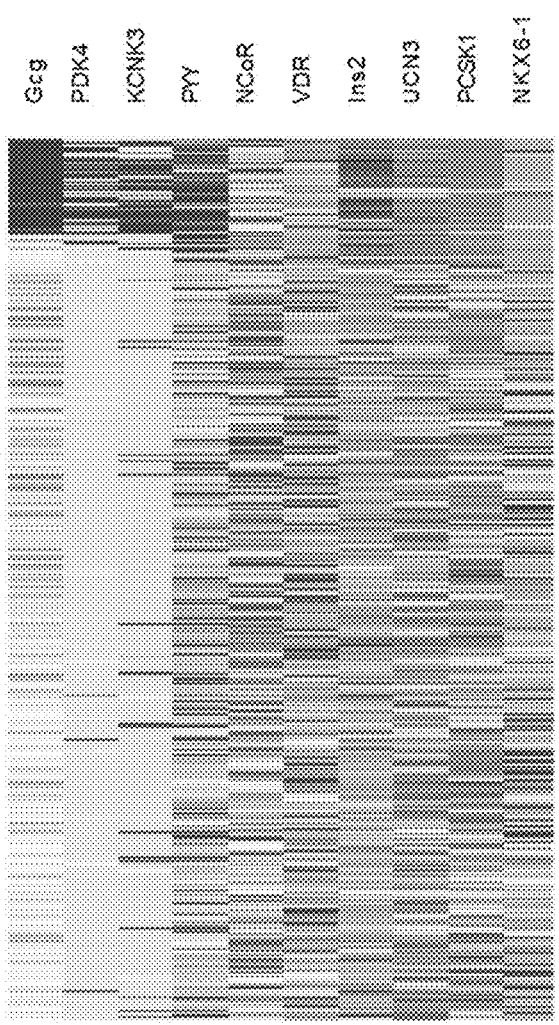

To identify the mechanisms regulating β cell survival and expansion, a genomic CRISPR knock-out screen (Wang et al., 2014, Science 343, 80-84) was performed in human induced pluripotent stem (iPS) cell-derived β-like cells (Yoshihara et al., 2016, Cell metabolism 23, 622-634). The incorporation of an inducible Cas9 expression system into β-like cells carrying a human insulin promoter-driven GFP reporter (INS-GFP) allowed genes essential for β-like cell survival to be identified (enrichment of sgRNAs in GFP- compared to GFP+ cells, FIG. 1A). Gene ontology analysis of the enriched genes reveals categories related to chromatin modification/remodeling, cell cycle and transcription (FIG. 1B). This unbiased genomic screen identified VDR as one of the most enriched gene targets, with 6 of the 7 sgRNAs targeting VDR found only in the GFP-cells (FIGS. 1C, D). Consistent with a potential role for VDR in β cell identity and/or survival, published data sets confirm VDR expression in both β cells and c cells (Benner et al., 2014, BMC genomics 15, 620; DiGruccio et al., 2016, Mol Metab 5, 449-458; Xin et al., 2016, PNAS 113, 3293-8). Further interrogation of a single cell transcriptional dataset (Xin et al., 2016, PNAS 113, 3293-8) revealed VDR to be one of the most highly expressed transcription factors in mouse islet cells, particularly in β cells (FIGS. 2A-2B).

To determine the functional significance of VDR expression in β cells, iPS cell lines harboring inducible shRNA knockdowns of VDR were differentiated into β-like cells and then challenged with IL1β. Consistent with VDR playing a role in cell survival during stress, increased cytokine-induced cell death was seen in the VDR-depleted β-like cells (FIG. 3A). Furthermore, in the rat β cell line INS1, the expression of key β cell genes was reduced in cytokine and palmitic acid treated cells upon VDR knockdown (FIG. 3B). Moreover, whole body VDR knock-out (KO) mice display increased islet staining for proinsulin, a marker of ER stress and β cell dysfunction, and an increased proinsulin:insulin ratio in the serum (FIGS. 1E, 1F, 3C, 3D) (Bouillon et al., 2008, Endocrine Rev. 29, 726-776; Hasnain et al., 2014, Nature Med. 20, 1417-26; Hasnain et al., 2016, J Mol Endocrinol 56, R33-54). Combined with reduced levels of insulin and MAFA in islets from VDR KO mice (FIG. 3E), these findings indicate that β cell function is compromised upon loss of VDR.

Given the above observations, it was determined whether VDR activation can protect β cells against inflammatory damage. Isolated mouse islets were cultured with IL1β in the presence or absence of the VDR ligand, calcipotriol (Cal), and the transcriptomic changes determined by RNA-Seq. Exposure to IL1β for 48 hours induced widespread transcriptional changes, with 704 and 718 genes up- and down-regulated, respectively (p<0.05, FIG. 3F). These transcriptional changes were largely maintained, with some even amplified, upon prolonged exposure (1090 and 989 genes up- and down-regulated after 96 hours, FIG. 3F). Co-treatment with Cal protected islets from IL1β-induced damage, with more pronounced effects evident at the later time point (FIGS. 3F-3J). Gene ontology of the IL1β suppressed genes whose expression was restored upon Cal treatment are mainly associated with β cell function, whereas the IL1β induced genes repressed by Cal are associated with inflammation (FIGS. 3H, 3J). These observations indicate that VDR can protect against IL1β-induced β cell dysfunction, by counteracting the inflammatory response and maintaining β cell functionality.

Example 3

VDR Shuttles Between BRD9 and BRD7

To determine the molecular underpinning of VDR function, the VDR interactome was characterized in human β-like cells. INS-GFP iPS cells incorporating an inducible ectopic expression system for HA-tagged VDR were differentiated into β-like cells, and VDR expression induced to coincide with the peak expression of insulin, as measured by GFP expression. VDR was subsequently immunoprecipitated from cells grown in the presence or absence of Cal 24 hours after VDR induction, and associating proteins identified by mass spectrometry.

Figure 4A:
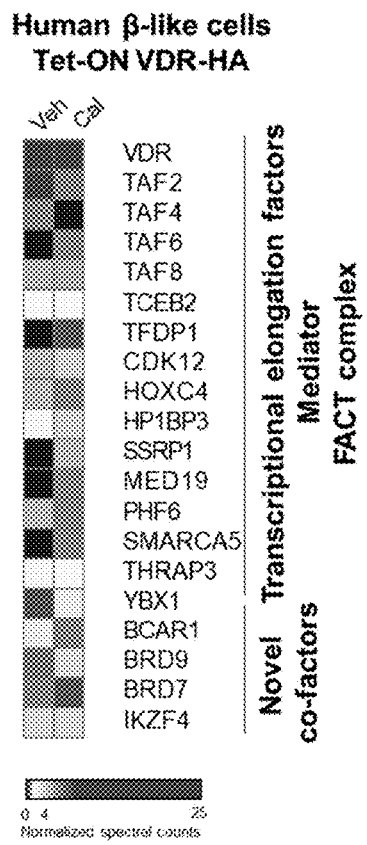
Figure 5A:
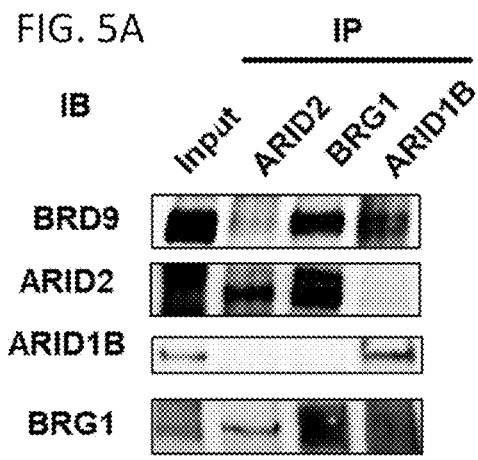
Figure 5B:
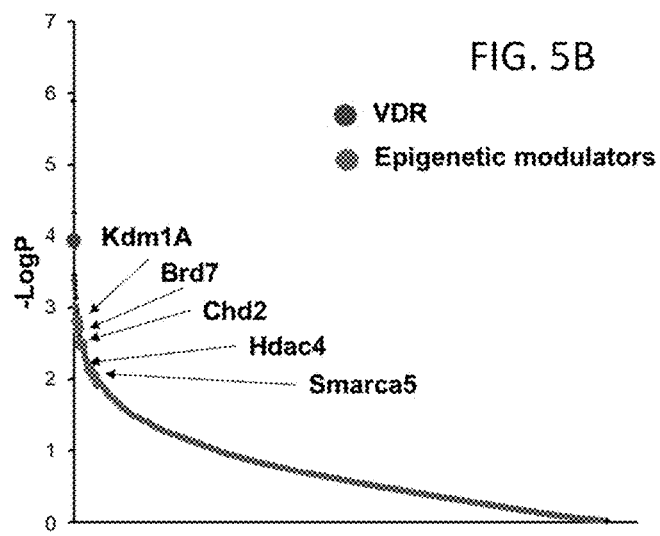

Multiple transcription elongation factors and components of the mediator and FACT complexes co-immunoprecipitated with VDR (FIG. 4A). In addition, novel VDR-interacting proteins were identified, most notably the bromodomain-containing factor 9 (BRD9), and its paralog, BRD7 (FIG. 4A). BRD9 was recently identified as a core component of the BAF complex, whereas BRD7 is found in the PBAF complex. Interestingly, BRD7 was also identified in these CRISPR screen (p=0.002), (FIGS. 1B, 5B).

Figure 4B:
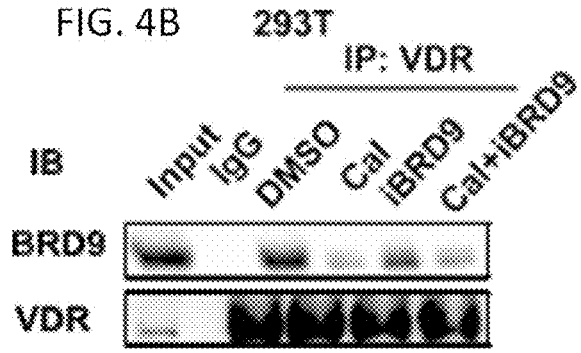
Figure 4D:
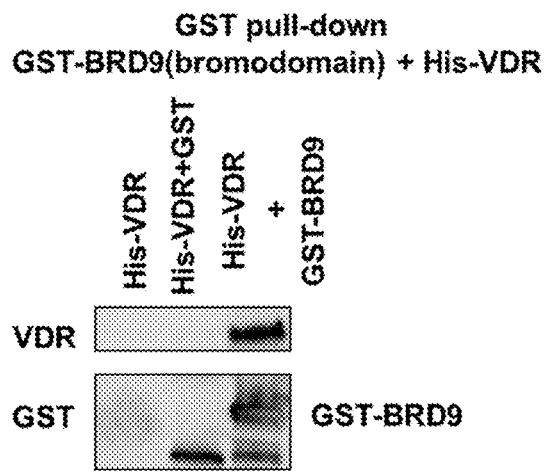
Figure 4C:
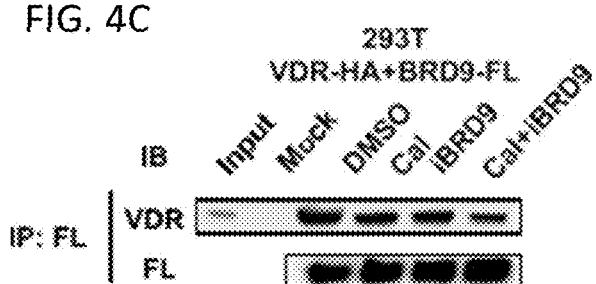
Figure 5C:
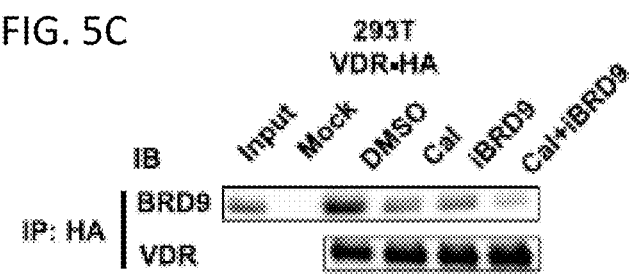
Figure 5D:
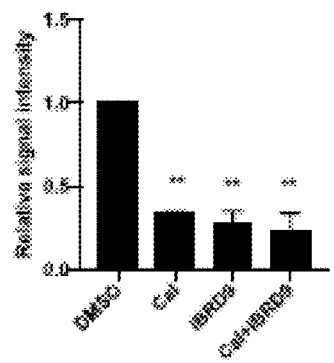
Figure 5E:
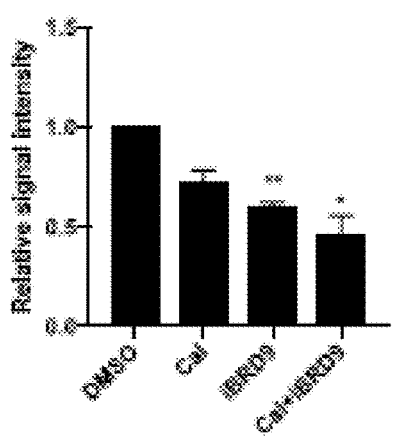
Figure 5F:
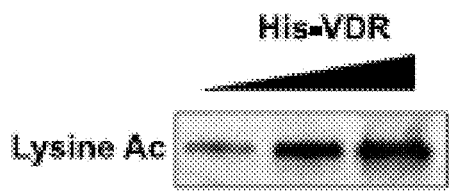

To verify these novel interactions, it was confirmed that endogenous BRD9 co-immunoprecipitates with HA-tagged VDR, and conversely, that HA-tagged VDR can be immunoprecipitated with Flag-tagged BRD9 in 293T cells (FIG. 4B, 4C, 5C). Somewhat surprisingly, the strength of this interaction decreased in the presence of VDR ligand as measured by proteomic and Western blot analyses (FIGS. 4A-4C, 5C-5E). Furthermore, a selective inhibitor of the bromodomain of BRD9, but not BRD7, iBRD9 (Theodoulou et al., J. Med. Chem. 99:1425-39, 2016), reduced the interaction between VDR and BRD9, indicating that BRD9 directly binds to VDR via its bromodomain (FIGS. 4B and C). Consistent with this, it was observed that the bromodomain of BRD9 is sufficient for the interaction with VDR (purified recombinant His-tagged VDR binds the GST-tagged bromodomain of BRD9 (FIGS. 4D, 5F).

Figure 4E:
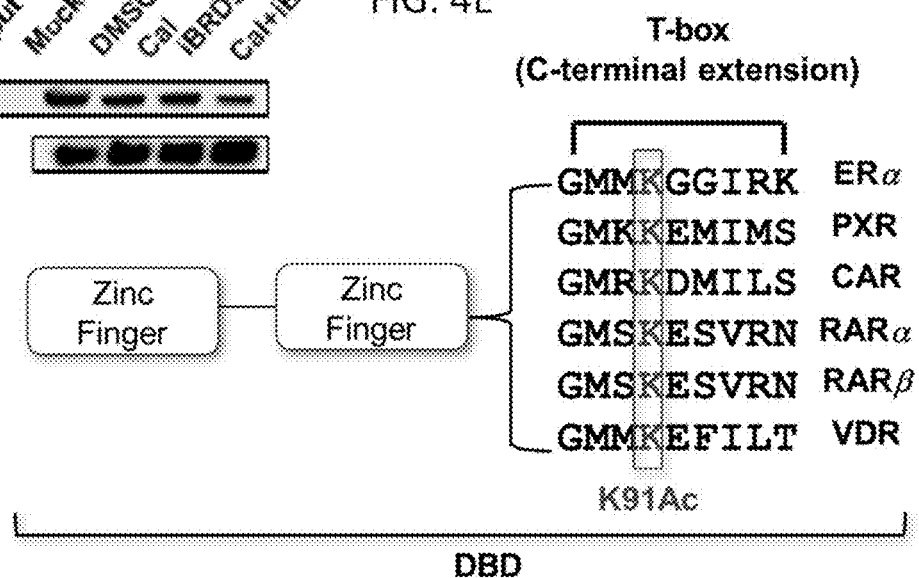

Since bromodomains bind acetylated lysines, it was hypothesized that acetylation of VDR was required for the interaction. Indeed, mass spectrometry clearly showed the presence of an acetylated lysine in a VDR peptide containing lysine 91 (K91Ac) (FIG. 5G). Interestingly, K91 is located in the T-box domain (Lee et al., 1994, European J. Biochem./FEBS 224, 639-650; Quack et al., 1998, Nucleic acids research 26, 5372-8) juxtaposed to the DNA-binding zinc fingers, a domain conserved in closely-related nuclear receptors including RARα and PXR (FIG. 4E). The crystal structure of the heterodimeric VDR:RXR DNA binding domains bound to direct repeat DNA elements (Shaffer and Gewirth, 2002, EMBO J 21, 2242-52) reveals the side-chain of K91 protruding away from the DNA double helix and on the opposite side to RXR, indicating it may serve as a docking site for the interaction with BRD9 (FIG. 4F). To confirm the importance of K91Ac in the VDR:BRD9 interaction, K91 was mutated to alanine (K91A) or arginine (K91R). Mutating K91 significantly reduced the interaction with BRD9, as well as the total acetylation level of VDR (FIG. 4G, 5H).

Similarly, it was confirmed that HA-tagged VDR was able to immunoprecipitate Flag-tagged BRD7 (FIGS. 4H, 5I). However, in contrast with BRD9, the interaction of VDR with BRD7 progressively increased in the presence of Cal and Cal+iBRD9, suggestive of competitive BRD9/BRD7 binding (FIG. 4H). Indeed, it was observed that VDR acetylation at the same site, K91, was required for the interaction with BRD7 (FIG. 4I), supporting the competitive binding hypothesis.

Figure 4J:
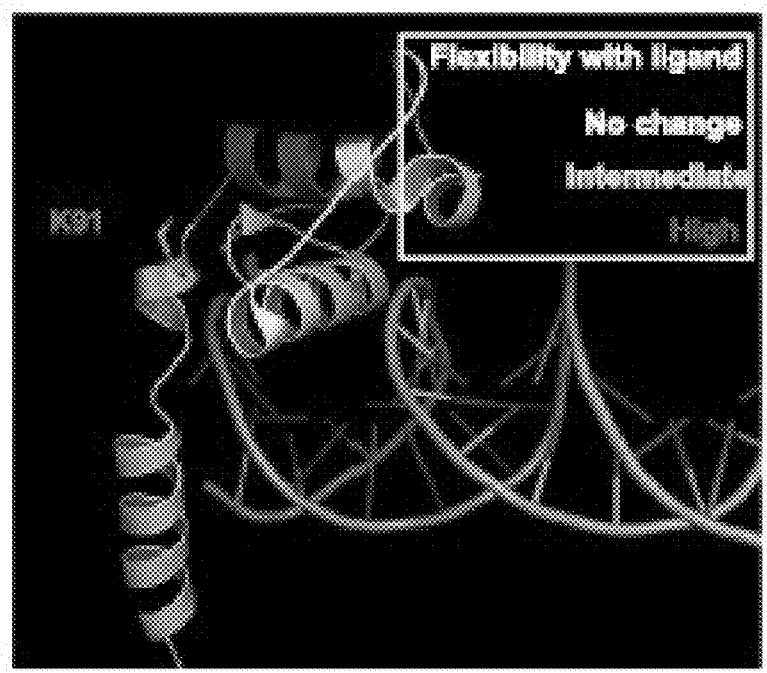

The notion of a ligand-induced shift in the association of VDR from BRD9 to BRD7 is supported by previous findings that revealed increased conformational flexibility in the DNA-binding domain and T box regions upon binding of 1,25(OH)2 vitamin D (Zhang et al., 2011, Nat. Struct. Mol. Biol. 18:556-63) (FIG. 4J).

Figure 4K:
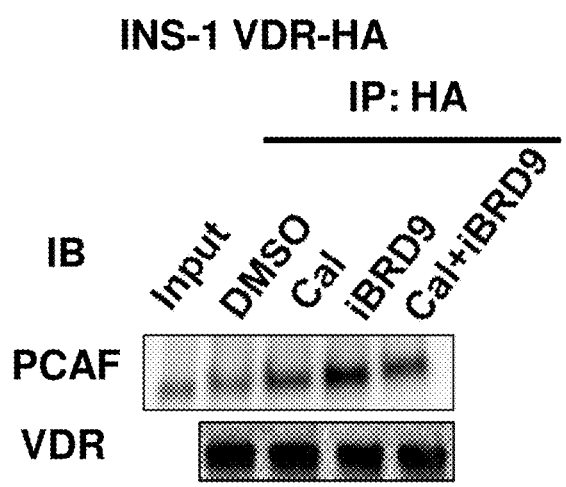
Figure 4L:
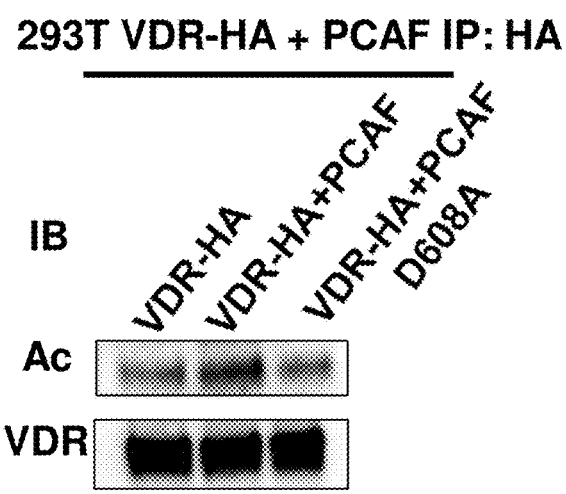

As the T-box region has been implicated in the interaction of nuclear receptors with PCAF (KAT2b) (Blanco et al., 1998, Genes & Development 12:1638-1651), the interaction between VDR and PCAF was examined. PCAF binding increased with Cal and/or iBRD9 treatment (FIG. 4K), as seen for BRD7 but the reverse of that seen for BRD9 binding. As a lysine acetyltransferase, it was determined whether PCAF directly acetylates VDR. VDR acetylation indeed increased when expressed together with PCAF, but not with the enzymatically dead PCAF D608A mutant (Jin et al., EMBO reports 15, 1192-1201, 2014) (FIG. 4L).

Taken together, these observations demonstrate an unrecognized regulatory mechanism for VDR, whereby T-box acetylation partitions recruitment between BRD9 or BRD7, depending on the absence or presence of VDR ligand, respectively.

Example 4

BRD9 Dissociation Promotes VDR-Mediated Transcription in β Cells

To determine if BRD9 and BRD7 recruit the SWI/SNF (BAF) and PBAF complexes, respectively, the effects of VDR ligand (Cal) and the BRD9 inhibitor (iBRD9) on the composition of the VDR protein complex was determined. VDR ligand (Cal) was used to favor BRD7-PBAF association, iBRD9 to block re-association to BAF.

Proteomic analyses of INS1 cells expressing HA-tagged VDR confirmed the ligand-dependent association of VDR with its heterodimeric partners, the RXRs, as well as components of the basal transcriptional machinery (FIG. 6A). The VDR association of proteins common to the BAF and PBAF complexes increased in the presence of Cal or iBRD9 (e.g., SMARCA1, SMARCA2, SMARCA4, FIGS. 6A, 6B, 8A-8E). The interactions of key components of the PBAF complex including PBRM1 (BAF180) and ARID2, but not components exclusive to the BAF complex (ARID1A and ARID1B), significantly increased in the presence of Cal or iBRD9 (FIGS. 6A, 6B, 8A-8E). This indicates that the activation state of VDR$^{K91Ac}$ (i.e., ±Cal or iBRD9), is conditional, dependent on its association with the BAF or PBAF complexes.

Based on these observations, it was proposed that BRD9 attenuates VDR activity. To determine if this regulatory mechanism is functional relevant in β cells, the effects of Cal and iBRD9 upon IL1β-induced stress in INS1 cells were determined (Hahn et al., 1997, Transplantation Proceedings 29:2156-7; Riachy et al., 2006, Apoptosis 11:151-9). Within 30 minutes of exposure, IL1β induced expression of Nfkbia (IκBα, a key negative feedback early response gene, Verma et al., 1995, Genes & Development 9:2723-35). This anti-inflammatory modulator was increased with Cal and Cal+iBRD9 treatments (FIG. 6C), with parallel changes seen at the protein level (FIG. 6D).

Figure 8A:
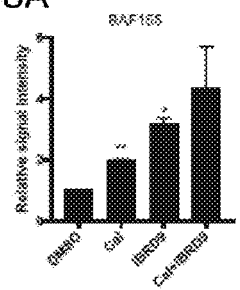
FIGS. 8A-8L. VDR regulates NFκB signaling. (A-E) Quantification of relative signal intensities corresponding to FIG. 6B (n=2, error bars show S.E.M., **p<0.01); (F) INS-1 cells expressing VDR-WT or VDR-K91R were treated with IL1β plus and minus Cal for 1 hr, and Nfkbia levels were measured by qPCR (n=3, error bars show S.E.M., *p<0.05); (G-I) ChIP-qPCR of ARID1B, a BAF-specific component, show that addition of iBRD9 reduces BAF complex binding at key VDR target loci Nfkbia, Nfkbiz, and Camk4; (J-L) ChIP-qPCR of BAF180, a PBAF-specific component, show that addition of iBRD9 increases PBAF complex binding at key VDR target loci Nfkbia, Nfkbiz, and Camk4.
Figure 8B:
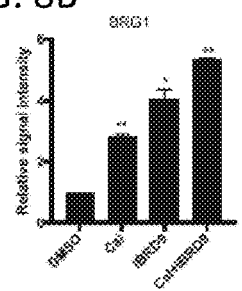
Figure 8C:
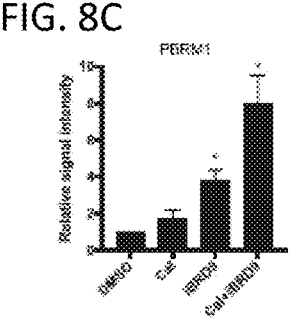
Figure 8D:
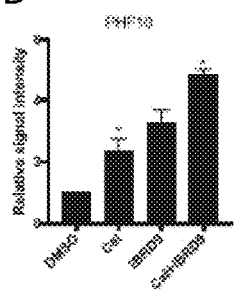
Figure 8E:
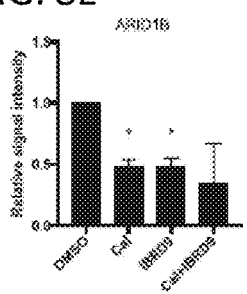
Figure 8F:
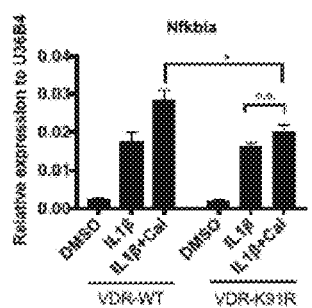
Figure 8G:
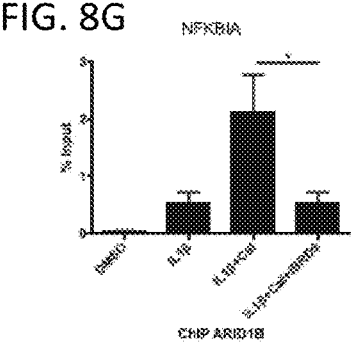
Figure 8H:
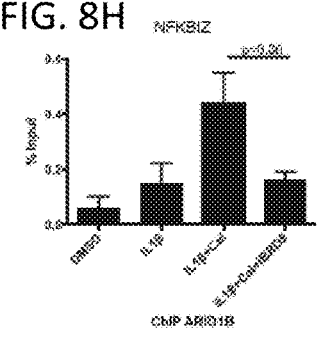
Figure 8I:
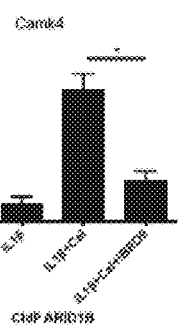
Figure 8J:
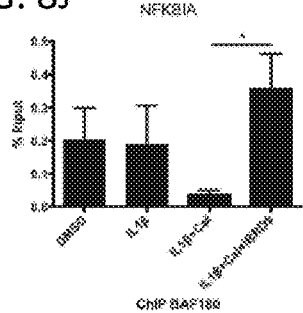
Figure 8K:
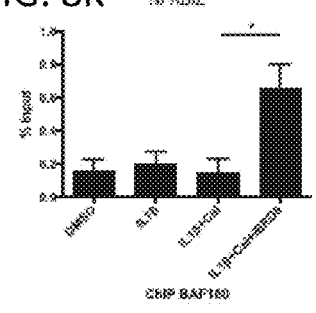
Figure 8L:
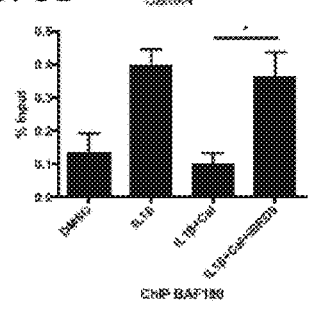

Furthermore, the induction of Nfkbia upon Cal treatment was largely abrogated in cells expressing the VDR mutant lacking the crucial lysine (K91R) (FIG. 8F). Beyond an acute effect, the iBRD9-Cal combination led to sustained Nfkbia induction (>24 hr) (FIG. 6E) portending a possible sustained anti-inflammatory effect (see below). Moreover, knockdown of the PBAF component PBRM1 or PCAF significantly compromised the activation of Nfkbia (FIG. 6F). These findings support BRD9 as a regulator of unliganded VDR, whereby inhibition of BRD9 binding allows increased association of VDR with the PBAF complex and PCAF to prolong transcriptional activation.

Example 5

Enhanced Activation of VDR Promotes a β Cell Stress Response

Transcriptional changes induced by the addition of Cal and iBRD9 were used to explore mechanistic transitions in cytokine-stressed β cells.

IL1β alone led to rapid widespread changes in INS1 cells, with 499 and 496 genes significantly induced and repressed, respectively, 1 hour after treatment (fold change >1.5) (FIG. 7A). Co-treatment with Cal+iBRD9 protected the cells against cytokine-induced stress, abrogating ~25% of the IL1-induced transcriptional changes (141 up- and 127 down-regulated genes, FIGS. 7A and 7B). Gene ontology (GO) analyses of these Cal+iBRD9-responsive genes identified β cell function (FIG. 7C), and cytokine response and NF-κB signaling (FIG. 7D) in the IL1β-repressed and induced gene sets, respectively. Thus, Cal+iBRD9 significantly protects against cytokine-induced damage by reducing the pro-inflammatory response and preventing the loss in functionality of β cells.

The proteomics data indicated that inhibiting the interaction with BRD9 redirects VDR towards the PBAF complex (FIGS. 6A and 6C). Consistent with this, it was observed that Cal+iBRD9 treatment reduced ARID1B binding—a component of the BAF complex, and increased BAF180 binding—a component of the PBAF complex, at multiple target gene promoters (FIGS. 8A-8L).

Given the established roles of the BAF and PBAF complexes in chromatin remodeling, the impact of this VDR-directed switch on genome-wide chromatin accessibility was determined. Notably, transposase-based sequencing (ATAC-Seq) (Buenrostro et al., 2013, Nature methods 10, 1213-8) revealed a synergistic overhaul of chromatin accessibility upon Cal and iBRD9 treatments. IL1β induced stress led to an overall reduction in chromatin accessibility in INS1 cells one hour after treatment (FIG. 7E). In contrast, Cal and iBRD9 as single agents antagonized a large portion of these changes, resulting a significant increase (>4-fold) in chromatin accessibility at ~4% (1,935 and 1,703 peaks) of all ATAC-seq peaks in IL1β-treated cell (FIGS. 7E and 7F). The combined Cal+iBRD9 treatment increased accessibility and resulted in global increases (>4-fold) at >3 times more peaks (~15%, 7,932 out of 51,397 peaks) (FIGS. 7E and 7F).

Figure 7I:
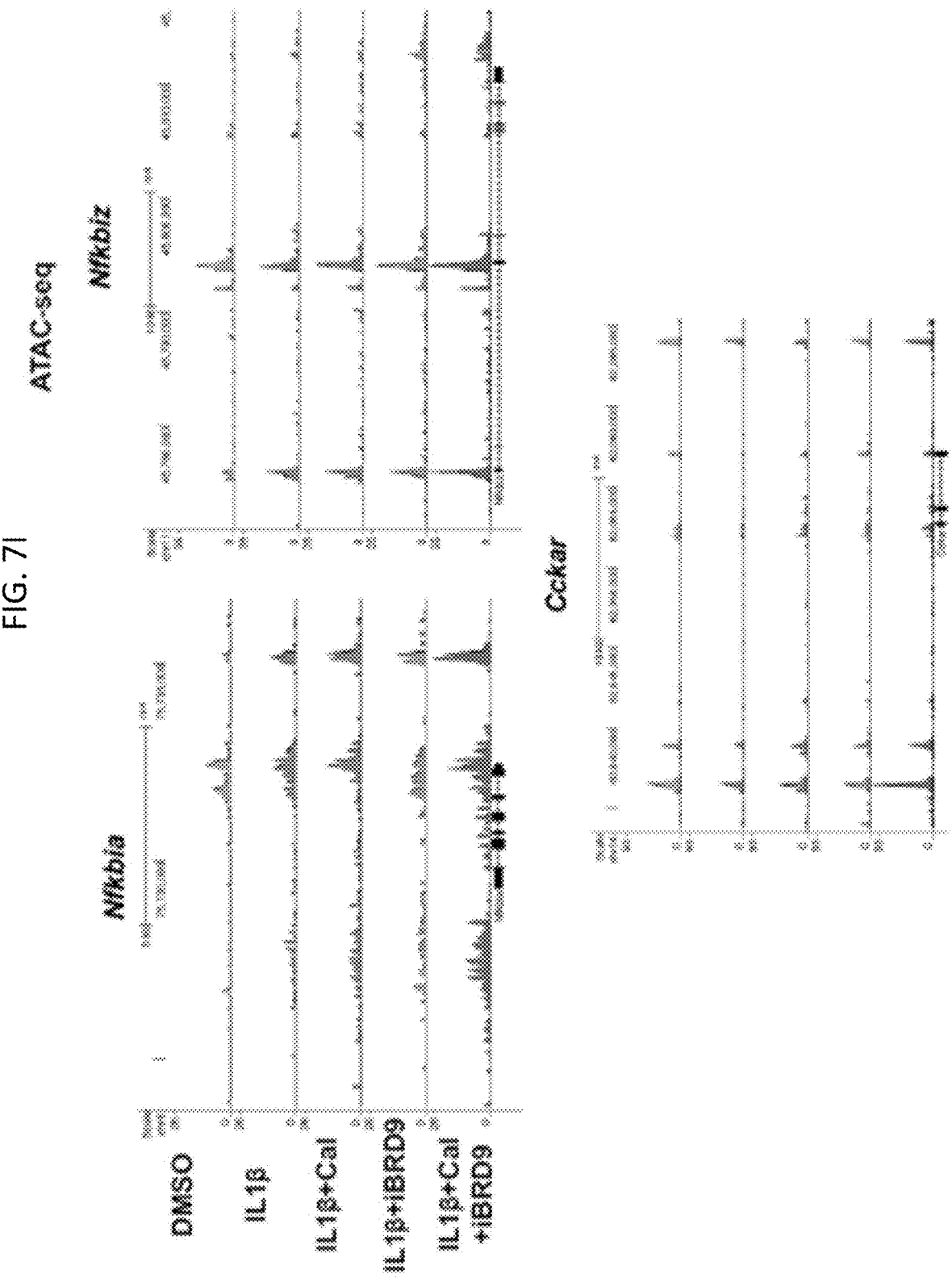

Motif analyses of Cal+iBRD9-induced ATAC-Seq peaks identified Vitamin D response elements (VDREs) as the top-ranking motif together with CTCF (FIG. 7G), indicating a direct role of VDR in counteracting the effects of IL1β. Indeed, chromatin accessibility was markedly increased at identified VDREs upon Cal+iBRD9 treatment (FIG. 7H). In particular, chromatin accessibility at Nfkbia and Nfkbiz was significantly increased upon Cal+iBRD9 treatment (FIG. 7I), consistent with the sustained Nfkbia expression (FIG. 7I). In addition, the reduction in chromatin accessibility induced by IL1β stress at key genes involved in β cell functionality including Cckar was reversed by Cal+iBRD9 treatment (FIG. 7I).

These observations indicate dissociating BRD9 from VDR by ligand or inhibitor results in selected increases in chromatin accessibility at VDR target genes.

Example 6

Activation of VDR Reverses Cytokine-Induced Changes in Enhancer Landscape

To determine how BRD9 regulates VDR-driven transcriptional responses, the genome-wide enhancer landscape was mapped using H3K27Ac as a mark of active enhancers (Rada-Iglesias et al., 2011, Nature 470, 279-283). Short-term IL1β exposure (1 hour) significantly altered the enhancer landscape, with widespread decreases and increases in H3K27 acetylation (FIGS. 9A and 9B, respectively). As was observed for chromatin accessibility (FIG.

7E), Cal and iBRD9 as single agents were both able to partially reverse the impact of IL1β (FIGS. 9A and 9B). Examination of the sites where Cal+iBRD9 treatment increased H3K27 acetylation revealed VDRE as the most enriched motif (FIG. 9C), indicating a direct role for VDR in reversing the 1LIP-induced enhancer changes. Furthermore, an interrogation of the Cal+iBRD9 rescued gene set (FIG. 7B) revealed that the VDRE-proximal decreases (at repressed genes, FIG. 9D) and increases (at activated genes, FIG. 9E) in H3K27 acetylation induced by IL1β were partially restored with Cal+iBRD9 treatment (FIGS. 9D-9F).

Given the sustained hyper-activation of Nfkbia expression observed with the combined Cal+iBRD9 treatment (FIG. 6E), the epigenomic changes after a prolonged IL1 stress (6 hours) were determined. At this later time point, increased H3K27Ac with Cal+iBRD9 treatment was seen at 945 peaks compared to Cal alone, of which 149 (16%) contained VDREs (FIG. 9G). The genes associated with these VDRE$^+$ peaks are mainly related to R cell function (e.g., Camk4) and anti-inflammatory responses (e.g., Nfkbia, FIGS. 9H-9I). Concomitantly, Cal+iBRD9 treatment reduced H3K27Ac at 1232 peaks, of which 130 (10.5%) contain VDREs (FIG. 9J), with the VDRE$^+$ gene set mainly related to the inflammatory response (FIGS. 9K and 9L).

Together, these data indicate a synergistic action of Cal+iBRD9 on H3K27Ac levels that effect both transcriptional activation and repression. The less pervasive changes in H3K27Ac levels compared to those in chromatin accessibility are consistent with alterations in enhancer elements being secondary to changes in chromatin accessibility. Combined with the marked changes in chromatin accessibility (FIGS. 7E-7I), these data identify a balance between PBAF- and BAF-modulated VDR transcription whereby VDR activation in combination with BRD9 inhibition shifts VDR toward the PBAF complex, resulting in reshaping of the enhancer landscape and antagonism of cytokine-induced transcriptomic changes.

Example 7

VDR-PBAF Complex Reverses R Cell Dysfunction to Reduce Hyperglycemia

The improvements in markers of p cell survival and function with Cal+iBRD9 treatment indicate that this approach may have therapeutic utility. The benefits of Cal+iBRD9 treatment in a dietary stress mouse model were examined.

Figure 10A:
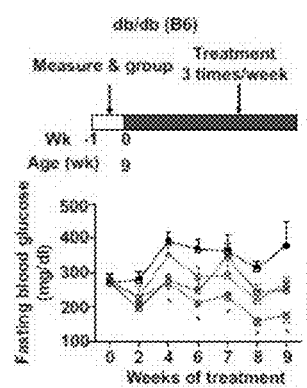
FIGS. 10A-10I. Combinatorial treatment of Cal and iBRD9 rescue β cell dysfunction and improve glucose metabolism in type 2 diabetes animal models. (A) 9 week old db/db (B6) male mice were grouped and treated with vehicle, Cal, iBRD9 or Cal+iBRD9 through i.p. injections 3 times a week. Treatment with Cal mildly reduces overnight fasting glucose levels in db/db (B6) mice, whereas Cal+iBRD9 potently reduces glucose levels (n=6-11, error bars show S.E.M., *P<0.05). (B) Mice in all groups maintain similar weight (n=6, error bars show S.E.M.). (C) Cal-treated and Cal+iBRD9 treated db/db (B6) mice (after 9 weeks treatment) have better glucose tolerance based on IP glucose tolerance test (IPGTT) (n=6, error bars show S.E.M., *P<0.05). (D) Cal, iBRD9, and Cal+iBRD9-treated db/db (B6) mice have higher fasting serum insulin levels (n=4-6, error bars show S.E.M., *P<0.05). (E) Cal+iBRD9 treated db/db (B6) mice secrete more insulin during a glucose challenge. (F) 9 week old db/db (BKS) male mice were grouped and treated with vehicle, Cal or Cal+iBRD9 through i.p. injections 3 times a week. Cal+iBRD9 treatment significantly reduced overnight fasted glucose levels in db/db (BKS) mice (n=8, error bars show S.E.M., *P<0.05). (G) Cal and Cal+iBRD9-treated db/db (BKS) mice have higher fasting serum insulin levels (n=5, error bars show S.E.M., *P<0.05). (H) 8 week old C57/B6 male mice were grouped and injected with low-dose STZ everyday for 5 consecutive days. 1 week after the final injection, the mice were grouped based on glucose levels and treated with vehicle, Cal or Cal+iBRD9 through i.p. injections 3 times a week. Cal+iBRD9 treatment significantly reduced overnight fasted glucose levels in low-dose STZ-treated mice (n=8-10, error bars show S.E.M., *P<0.05). (I) IPGTT of STZ-treated mice reveals better glucose tolerance for Cal+iBRD9 treated mice (n=5, error bars show S.E.M., *P<0.05).
Figure 10B:
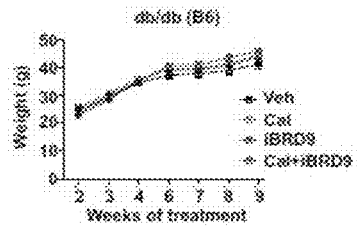

B6.BKS(D)-Lepdb/J (hereafter referred to as db/db (B6)) mice have markedly increased levels of cytokines that lead to β cell dysfunction and insulin resistance (Chan et al. 2013, Diabetes 62:1557-1568). To determine whether VDR-driven therapies are protective against dietary-induced inflammatory stress, mice were injected with vehicle, Cal alone (60 µg/kg i.p.), iBRD9 alone (10 mg/kg i.p.), or the combination (Cal: 60 µg/kg i.p.+iBRD9:10 mg/kg i.p.) 3 times a week for 9 weeks. Vehicle-treated db/db (B6) mice developed pronounced hyperglycemia within 4 weeks, with fasted blood glucose levels ~400 mg/dl (FIG. 10A). Cal and iBRD9 as single agents achieved modest improvements in blood glucose levels after 4-6 weeks treatment. However, mice receiving the Cal+iBRD9 combination showed a significant reduction in blood glucose after 4 weeks treatment, with the beneficial effects progressively increasing with treatment duration (FIG. 10A). These improvements in glucose homeostasis were achieved without significant changes in body weight (FIG. 10B), liver or epididymal white adipose tissue (eWAT) weights, serum calcium level, or metabolic rate (FIGS. 11A-11E).

Figure 10C:
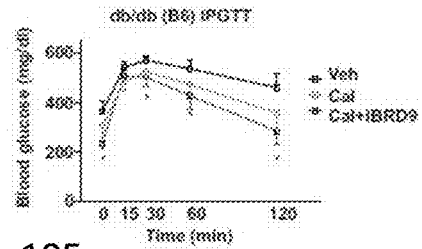
Figure 10D:
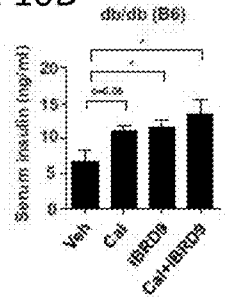
Figure 10E:
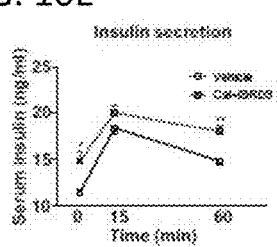

Intraperitoneal glucose tolerance tests (IPGTT) were performed to evaluate the functionality of the β cells independent of the incretin effect. While mice treated with Cal alone showed improved glucose clearance compared to vehicle-treated mice, more significant improvements were achieved with Cal+iBRD9 (FIG. 10C), indicating improved insulin secretion with the combination therapy. Consistent with this, random fed serum insulin levels were significantly increased by Cal+iBRD9 treatment, and increased insulin secretion was observed during an intraperitoneal glucose challenge (FIGS. 10D, 10E). These observations indicate that activation of VDR combined with the dismissal of the BAF complex improves β cell function and thereby glucose homeostasis in an inflammation-driven diabetes model.

Figure 10F:
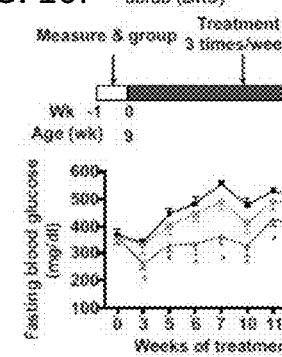
Figure 10G:
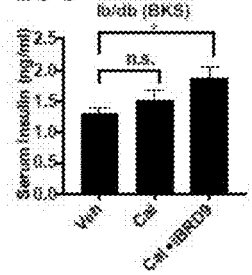
Figure 11A:
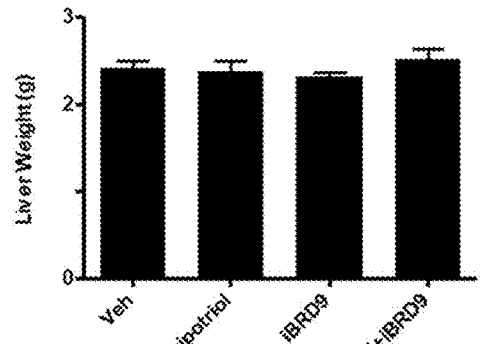
FIGS. 11A-11F. Cal and iBRD9 do not affect whole body metabolism. (A) Liver weight of db/db (B6) mice treated with Vehicle, Cal, iBRD9, or Cal+iBRD9 (n=6, error bars show S.E.M.). (B) Epididymal white adipose tissue (eWAT) weight of db/db (B6) mice treated with Vehicle, Cal, iBRD9, or Cal+iBRD9 (n=6, error bars show S.E.M.). (C) Oxygen consumption (VO2) of mice treated with vehicle or Cal+iBRD9. (D) $CO_2$ production of mice treated with vehicle or Cal+iBRD9. (E) Serum calcium levels of mice in all treatment groups (n=10, error bars show SD). (F) Whole body weights of db/db (BKS) mice during treatment with Vehicle, Cal or Cal+iBRD9.
Figure 11B:
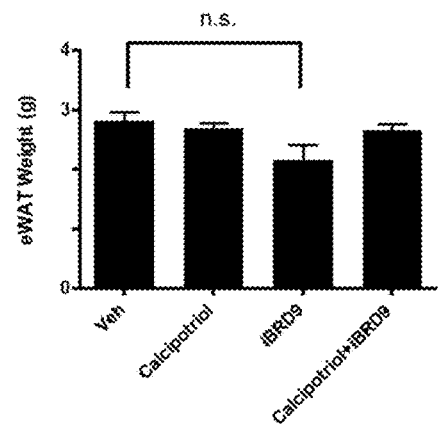
Figure 11C:
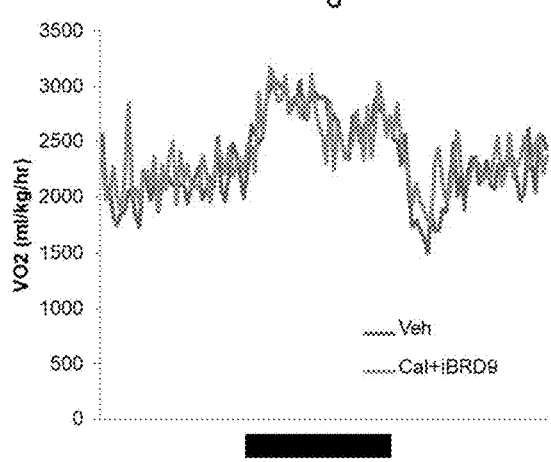
Figure 11D:
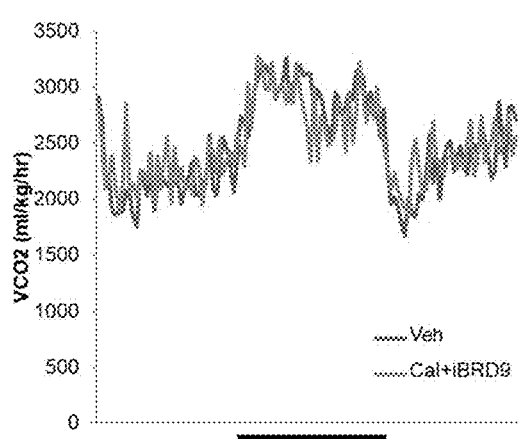
Figure 11E:
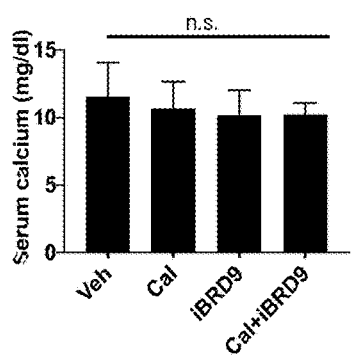
Figure 11F:
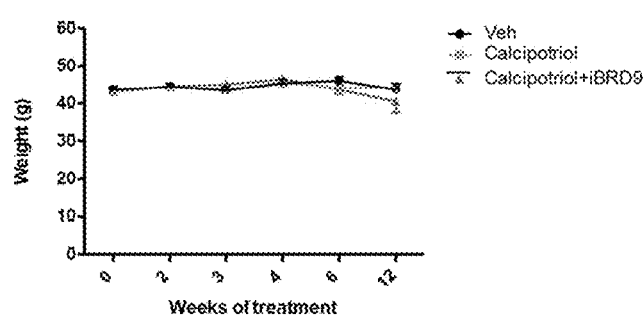

Mice lacking the leptin receptor on a BKS genetic background (C57BLKS-Leprdb, hereafter as db/db (BKS)) develop a more severe diabetic phenotype than db/db (B6) mice. Chronic hyperglycemia in db/db (BKS) progresses to β cell atrophy, hypoinsulinemia and β cell failure, resembling the progression of patients with genetic defects in β cell function. In these genetically predisposed mice, treatment with Cal alone (60 µg/kg i.p. 3 times/week) provided only limited improvements in glucose management (FIG. 10F). In contrast, 3 weeks co-treatment with Cal+iBRD9 reduced the fasting blood glucose levels, and continued treatment maintained these levels for ~10 weeks without any body weight changes (FIGS. 10F, 11F). Consistent with improved glucose management, Cal+iBRD9 treatment partially ameliorated the hallmark hypoinsulinemia associated with the db/db (BKS) model (FIG. 10G).

Figure 10H:
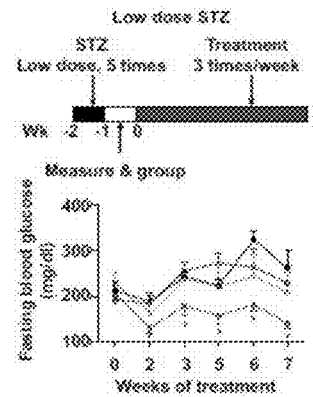
Figure 10I:
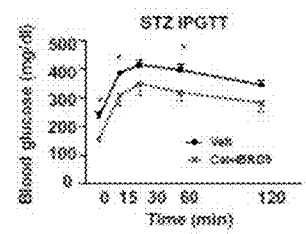
Figure 12A:
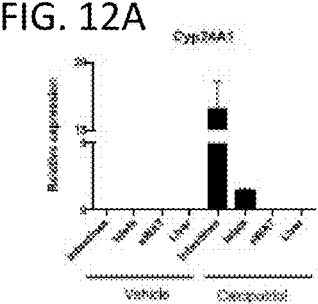
FIGS. 12A-12J. Cal and iBRD9 combination restores glucose metabolism in multiple mouse models. (A) VDR target gene Cyp24A1 expression in multiple tissues, indicating islets are directly targeted by Cal treatment (n=3, error bars show S.E.M., *P<0.05). (B) Islets from db/db (B6) mice treated with Cal show increased expression of Ins2 (n=3, error bars show S.E.M., *P<0.05). (C) Key hepatic gluconeogenesis genes are repressed in Cal-treated db/db (B6) mice, suggesting higher levels of serum insulin suppresses gluconeogenesis from liver. (D) Low-dose STZ treated mice show increased levels of insulin with Cal or iBRD9 treatment (n=8-10, error bars show S.E.M.). (E) Immunofluorescence staining of NKX6-1 (red), a key transcription factor for β cell identity and function, in pancreas sections from vehicle and Cal+iBRD9-treated low-dose STZ treated mice. (Scale bar: 50 mm). (F) Heatmap of qPCR results of multiple inflammatory gene expression in islets from aged h-IAPP mice treated with Cal or Cal+iBRD9. Islets were collected from 15 month old mice and cultured ex vivo in ultra-low attachment plates. Cal or Cal+iBRD9 were treated for 72 hours. (G) Western blotting of ER stress marker p-PERK in INS-1 cells treated with Thapsigargin (0.25 mM) or Tunicamycin (5 mg/ml) overnight. Cal was pre-treated 1 hour. (H) Immunohistochemistry staining of ER stress markers Calnexin and PERK in pancreatic tissue sections in db/db (BKS) mice. (I) qPCR of Nfkbia expression in INS-1 cells exposed to IL1β and Cal and multiple BRD9 inhibitors. (n=3, error bars show S.E.M., *p<0.05, **p<0.01). (J) In vivo pharmacokinetic study of iBRD9 (n=3, error bars show SEM).
Figure 12B:
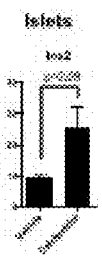
Figure 12C:
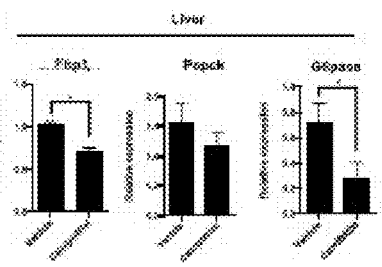
Figure 12D:
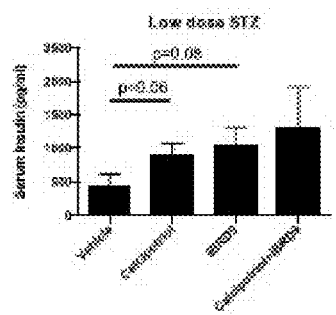

The therapeutic utility of targeting VDR in a β cell damage model, designed to mimic the severe β cell loss observed in the final stages of T2D patients was examined. B6/J mice treated with low-doses of streptozotocin (STZ) progressively lost glucose control. Cal and iBRD9 as single agents provided limited to no benefit in this β cell damage model. Notably, the combination Cal+iBRD9 treatment provided extended improvements in glucose control (FIG. 10H) and increased glucose tolerance and serum insulin levels (FIGS. 10I, 12D).

In combination, in vivo application of VDR ligand and iBRD9 results in enhanced β cell function and insulin secretion in each of the three mouse models representing different stages of T2D progression, demonstrating the therapeutic value of this combinatorial strategy.

Example 8

Targeting the VDR-BRD9 Axis Rescues

β Cell Dysfunction in Mouse and Human Islets

To understand how VDR activation improves glucose homeostasis in each of the three mouse models, the molecular and structural changes induced in islets were compared. The marked induction of Cyp24A1, a classic VDR target gene, confirmed VDR activation in islets as well as in the intestine of the Cal-treated db/db (B6) mice (FIG. 12A). In addition, Ins2 mRNA levels trended upwards in Cal-treated islets, consistent with the increase seen in serum insulin levels (FIGS. 12B, 11D). Transcriptomic analysis revealed the upregulation of multiple key transcription factors including Nkx6-1 and Nr4a1 (FIG. 13A), whose repression correlates with β cell dysfunction (Guo et al., 2013, J. Clin.

Invest. 123, 3305-16; Talchai et al., 2012, Cell 150, 1223). Furthermore, multiple cytokine and chemokine genes were downregulated, further indicating that activation of VDR reduced the pro-inflammatory response in islets (FIG. 13A). Gene ontology of the upregulated genes identified pathways involved in β cell function including OXPHOS, secretion and R cell proliferation (FIG. 13B) enriched in the Cal-treated islets. In addition, reduced expression of gluconeogenesis genes, including Pepck, Fbp1 and G6pase, in the liver of Cal-treated mice, most likely caused by elevated serum insulin (FIG. 12C) was observed. Thus, the benefits of VDR activation in the inflammation-driven db/db (B6) model are multifactorial, including reduced inflammation, improved β cell function and decreased hepatic gluconeogenesis.

Figure 13H:
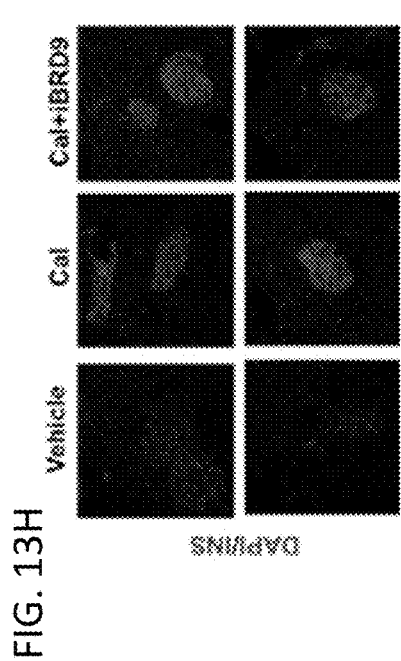

Distinct from diet-induced T2D models, β cell intrinsic defects in db/db (BKS) mice severely compromise β cell proliferation and are considered the major cause for the phenotype severity (Puff et al., 2011, Horm. Metab. Res. 43, 306-311). Notably, 12 weeks of Cal+iBRD9 treatment led to ~70% increase in islet area in the pancreas, as well as a significant increase (~100%) in the size of individual islets in db/db (BKS) mice (FIGS. 13C-13E). Consistent with this observation, the number of proliferating cells measured by Ki67 labeling more than doubled after Cal+iBRD9 treatment (FIGS. 13F and 13G). Intracellular insulin level was also rescued by Cal or Cal+iBRD9 treatment (FIG. 13H), indicating that the β cell dysfunction(Guo et al., 2013, *J. Clin. Invest.* 123, 3305-16) is reversed upon VDR activation.

Figure 12E:
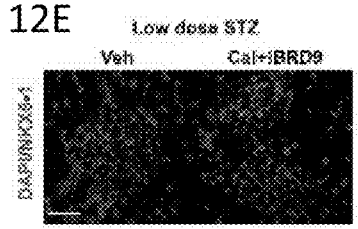

As a model of phase III or end stage diabetes, low-dose STZ treatment induces islet loss and α cell expansion (Li et al., 2000, J. Endocrinol. 165, 93-99). Cal+iBRD9 was protective against progressive β cell death, with increased insulin and decreased glucagon staining seen after 7 weeks of treatment (FIGS. 13I, 13J). These changes were accompanied by an increase in the level of NKX6-1, a marker for β cell function (FIG. 12E), further indicating that the β cell dysfunction caused by multiple layers of stress is ameliorated upon enhanced VDR activation. Therefore, Cal+iBRD9 treatment improves glucose homeostasis in multiple diabetic mouse models through the reversal of β cell dysfunction and increased insulin secretion.

Figure 12F:
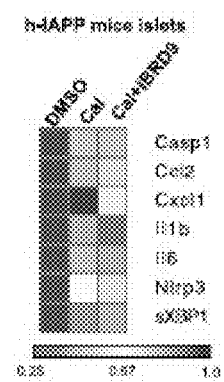
Figure 12G:
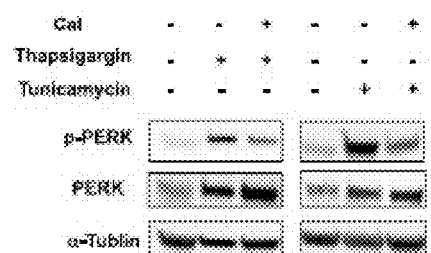
Figure 12H:
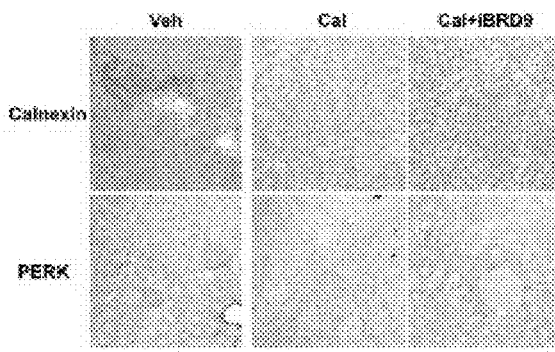

In addition to inflammation, ER stress, and IAPP amyloid deposition, lipo- and glucotoxicity all contribute to islet dysfunction in human T2D patients. To determine whether vitamin D signaling can modulate the damage attributed to additional stressor, islets from aged (15 months) transgenic mice carrying a copy of human islet amyloid polypeptide driven by rat insulin II promoter (Janson et al., 1996) were treated with Cal or Cal+iBRD9 for 72 hr ex vivo. Multiple inflammatory and stress markers were reduced upon Cal or Cal+iBRD9 treatment (FIG. 12F). In addition, thapsigargin or tunicamycin-induced ER stress in INS1 cells was attenuated by Cal treatment (FIG. 12G). ER stress markers Calnexin and PERK were reduced in db/db (BKS) mice treated with Cal or Cal+iBRD9 (FIG. 12H), indicating that VDR activation can reduce ER stress in highly dysfunctional β cells in vivo.

Figure 12I:
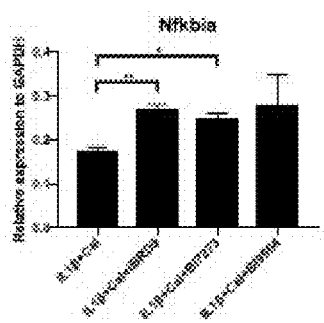
Figure 12J:
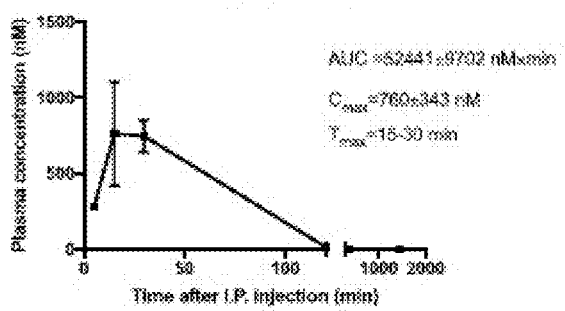

While the significant improvements seen in the diabetic models are consistent with the effects observed in β cell lines upon Cal+iBRD9 treatment, efficacy in related tissues such as macrophages or the intestines, or off target effects cannot be excluded. In support of the specificity of iBRD9, structurally unrelated BRD9 inhibitors (Hohmann et al., 2016, Nat. Chem. Biol., 12:672-9; Martin et al., 2016, J. Med. Chem. 59:4462-75) induced similar anti-inflammatory effects on NF-κB signaling (FIG. 12I). In addition, the maximum plasma iBRD9 concentration (~750 nM) (FIG. 12J) is sufficient to activate BRD9 (IC50=50 nM) while sparing other bromodomain members such as BRD4 (IC50=5 mM). Collectively, these data support that the therapeutic efficacy of iBRD9 in vivo is on-target.

Figure 13K:
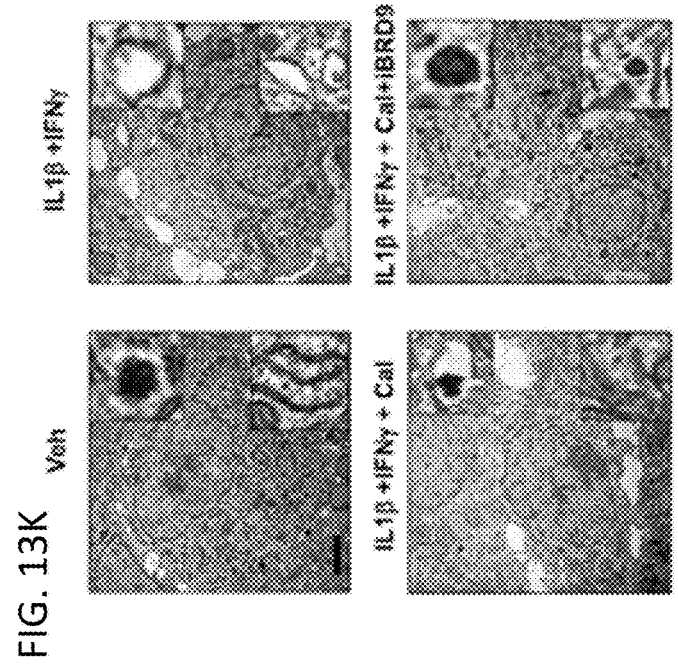
Figure 14A:
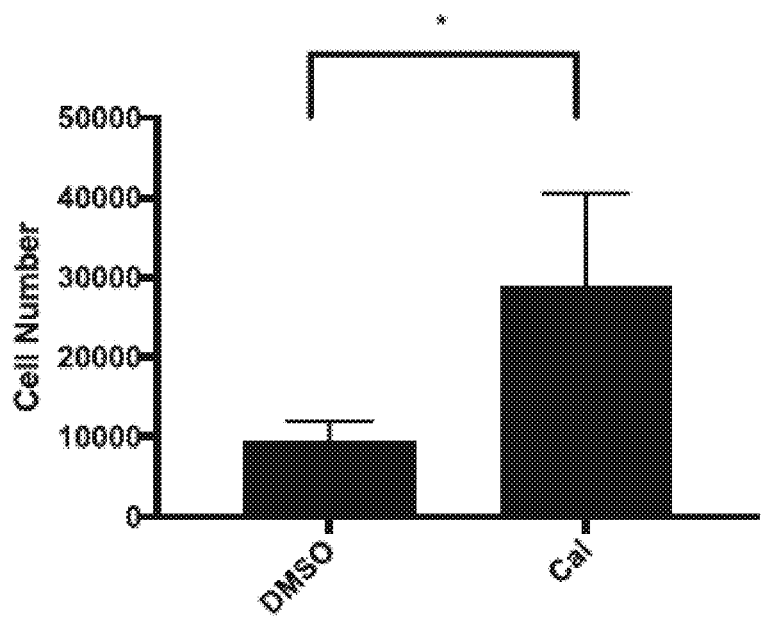
FIGS. 14A-14B. Calcipotriol Treatment Increases Ex Vivo Human Islet Survival and Insulin Secretion. (A) Cell numbers of ex vivo cultured human islets treated with vehicle or calcipotriol for 4 weeks (n=3, error bars show S.E.M., *p<0.05). (B) Insulin secretion assay of ex vivo cultured human islets treated with vehicle or calcipotriol for 1 week. (n=3, error bars show S.E.M., **p<0.01).
Figure 14B:
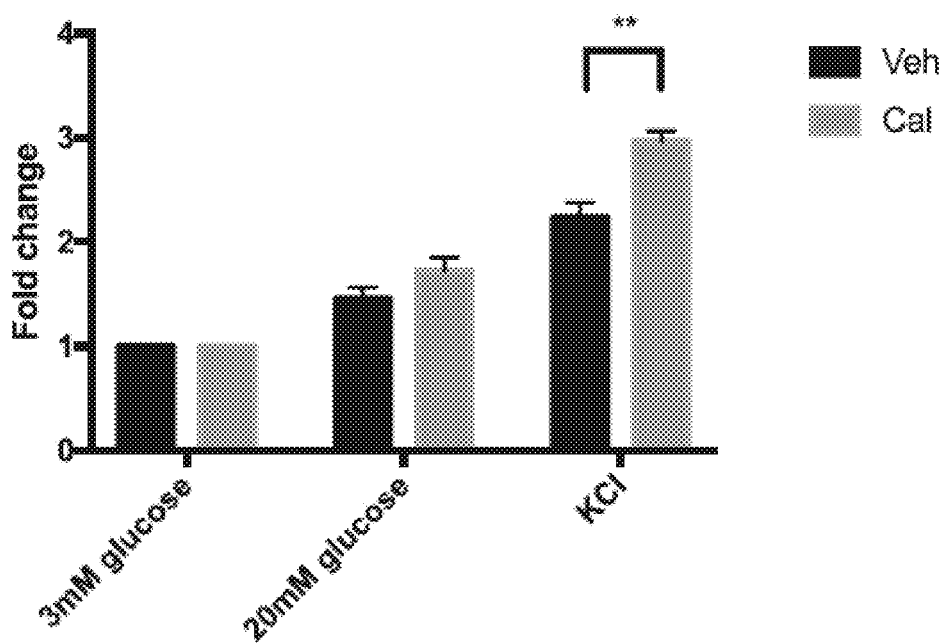

As islet allogenic transplants are a medium-term therapy for select patients, the ability of VDR activation to protect isolated human islets was examined. Healthy human islets were challenged with an inflammatory stress (Arnush et al., 1998, J. Clin. Invest. 102:516-26) (IL1β+interferon γ [IFN γ] for 24 hr) with or without activation of VDR. Transmission electron microscopy confirmed that IL1β and IFNγ caused severe islet damage including loss of dense insulin granules and dilation of the ER (FIG. 13K, upper and lower insets, respectively). Activation of VDR alone or in combination with iBRD9 rescued the damage caused by IL1β and IFN γ, most notably at the level of the insulin granules (FIG. 13K, upper insets, bottom panels) and ER morphology (FIG. 13K, lower insets, bottom panel). Additionally, Cal increased survival and insulin secretion capacity in long term ex vivo human islet cultures (FIGS. 14A and 14B). These findings demonstrate that enhanced vitamin D signaling has significant beneficial effects on islets during cytokine stress.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A method of reducing blood glucose in a mammal, comprising:
   administering a therapeutically effective amount of one or more vitamin D receptor (VDR) agonists to the mammal, wherein the one or more VDR agonists is calcipotriol, 25-hydroxy-$D_3$ (25-OH-$D_3$) (calcidiol); vitamin D3 (cholecalciferol); vitamin D2 (ergocalciferol), 1α,25-dihydroxyvitamin $D_3$ (calcitriol), or a combination thereof, and
   administering a therapeutically effective amount of one or more bromodomain-containing protein 9 (BRD9) antagonists to the mammal, wherein the one or more BRD9) antagonists is I-BRD-9, TP742, BI-7273, BI-9564, dBRD9, GNE-375, LP-99, or a combination thereof,
   thereby reducing blood glucose in the mammal.

2. A method of treating type 2 diabetes in a mammal, comprising:
   administering a therapeutically effective amount of one or more vitamin D receptor (VDR) agonists to the mammal, wherein the one or more VDR agonists is calcipotriol, 25-hydroxy-$D_3$ (25-OH-$D_3$) (calcidiol); vitamin D3 (cholecalciferol): vitamin D2 (ergocalciferol), 1α,25-dihydroxyvitamin $D_3$ (calcitriol), or a combination thereof, and
   administering a therapeutically effective amount of one or more bromodomain-containing protein 9 (BRD9) antagonists to the mammal, wherein the one or more BRD9) antagonists is I-BRD-9, TP742, BI-7273, BI-9564, dBRD9, GNE-375, LP-99, or a combination thereof,
   thereby treating type 2 diabetes in the mammal.

3. A method, comprising:
   administering a therapeutically effective amount of one or more vitamin D receptor (VDR) agonists to a mammal, wherein the one or more VDR agonists is calcipotriol, 25-hydroxy-$D_3$ (25-OH-$D_3$) (calcidiol); vitamin D3 (cholecalciferol); vitamin D2 (ergocalciferol), 1α,25-dihydroxyvitamin $D_3$ (calcitriol), or a combination thereof, and
   administering a therapeutically effective amount of one or more bromodomain-containing protein 9 (BRD9) antagonists to the mammal, wherein the one or more BRD9) antagonists is I-BRD-9, TP742, BI-7273, BI-9564, dBRD9, GNE-375, LP-99, or a combination thereof,
   wherein the method reduces fed and fasting blood glucose, increases insulin sensitivity, increases glucose tolerance, increases insulin secretion, increases beta cell function, increases the size of islets, reduced beta cell death, increases insulin granules, or combinations thereof, in the mammal.

4. The method of claim 1, wherein the therapeutically effective amount of the one or more VDR agonists is at least 0.01 mg/kg, the therapeutically effective amount of the one or more BRD9 antagonists is at least 0.1 mg/kg, or both.

5. The method of claim 1, wherein the administering is subcutaneous, intraperitoneal, intramuscular, intravenous or intrathecal.

6. The method of claim 1, wherein the mammal is a cat or dog.

7. The method of claim 1, wherein the mammal is a human.

8. The method of claim 2, wherein the VDR agonist is calcipotriol and the BRD9 antagonist is I-BRD9.

9. The method of claim 3, wherein the VDR agonist is calcipotriol and the BRD9 antagonist is I-BRD-9.

10. The method of claim 2, wherein the method further comprises administering an additional therapeutic compound.

11. The method of claim 1, wherein the VDR agonist is calcipotriol and the BRD9 antagonists is I-BRD9.

12. The method of claim 1, wherein the one or more VDR agonists and one or more BRD9 antagonists are administered concurrently.

13. The method of claim 1, wherein the one or more VDR agonists and one or more BRD9 antagonists are administered sequentially.

14. The method of claim 1, wherein the one or more VDR agonists, one or more BRD9 antagonists, or both, are part of a nanoparticle.

15. The method of claim 1, wherein the method further comprises administering an additional therapeutic compound.

16. The method of claim 15, wherein the additional therapeutic compound is insulin, an alpha-glucosidase inhibitor, amylin agonist, dipeptidyl-peptidase 4 (DPP-4) inhibitor, meglitinide, sulfonylurea, or a peroxisome proliferator-activated receptor (PPAR)-gamma agonist.

17. The method of claim 16, wherein the PPAR-gamma agonist is a thiazolidinedione (TZD), aleglitazar, farglitazar, muraglitazar, or tesaglitazar.

18. The method of claim 17, wherein the TZD is pioglitazone, rosiglitazone, rivoglitazone, or troglitazone.

* * * * *